United States Patent [19]

Watanabe et al.

[11] Patent Number: 5,353,653
[45] Date of Patent: Oct. 11, 1994

[54] HEAT EXCHANGER ABNORMALITY MONITORING SYSTEM

[75] Inventors: Michio Watanabe, Ayase; Kazuo Nogami, Yokohama; Yuji Muronosono, Kawasaki; Kanemitu Ohashi, Yamato, all of Japan

[73] Assignee: Kabushiki Kaisha Toshiba, Kawasaki, Japan

[21] Appl. No.: 697,777

[22] Filed: May 9, 1991

[30] Foreign Application Priority Data

May 10, 1990 [JP] Japan .................. 2-120682
Feb. 25, 1991 [JP] Japan .................. 3-053428

[51] Int. Cl.⁵ ............... G01M 19/00; G01N 17/00
[52] U.S. Cl. ............................ 73/865.9; 73/86; 165/11.1; 374/39
[58] Field of Search ............ 73/865.9, 86; 374/39, 374/40, 41, 43, 44; 364/507; 432/32; 422/53; 165/11.1, 11.2

[56] References Cited

U.S. PATENT DOCUMENTS

| | | | |
|---|---|---|---|
| 3,312,274 | 4/1967 | Sebald | 165/11.1 X |
| 3,504,323 | 3/1970 | Meany, Jr. | 73/86 X |
| 3,918,300 | 11/1975 | Weisstuch et al. | 73/112 |
| 4,245,501 | 1/1981 | Feller | 165/11.1 X |
| 4,432,232 | 2/1984 | Brantley et al. | 73/865.9 |
| 4,833,622 | 5/1989 | Barto et al. | 73/865.6 X |
| 4,928,751 | 5/1990 | Fischer, Jr. | 374/41 X |
| 5,058,443 | 10/1991 | Riedmaier | 73/865.9 |

FOREIGN PATENT DOCUMENTS

| | | | |
|---|---|---|---|
| 30459 | 6/1981 | European Pat. Off. | 165/11.1 |
| 217303 | 1/1985 | Fed. Rep. of Germany | 165/11.1 |
| 28940 | 2/1982 | Japan | 165/11.1 |
| 928163 | 5/1982 | U.S.S.R. | 165/11.1 |
| 1052824 | 11/1983 | U.S.S.R. | 165/11.1 |
| 1103066 | 7/1984 | U.S.S.R. | 165/11.1 |

*Primary Examiner*—Tom Noland
*Attorney, Agent, or Firm*—Foley & Lardner

[57] ABSTRACT

A system for monitoring abnormalities in a heat exchanger having heat-exchange tubes for heating feed water with extraction steam, an inlet and an outlet for the feed water, and a drain cooling zone, includes a process input, an apparatus for calculating the differential pressure between the feed water pressures at the inlet and outlet, an apparatus for computing the heat exchanging performance of the heat exchanger, and judgement apparatus for monitoring the differential pressure and the heat exchanging performance, thereby judging the presence or absence of scale accretion within the heat exchanger end, whenever scale accretion is present, judging the specific locations of the scale accretion in the inner and outer surfaces of the heat-exchange tubes, fluid flow distribution passageways and devices other than the heat-exchange tubes.

6 Claims, 28 Drawing Sheets

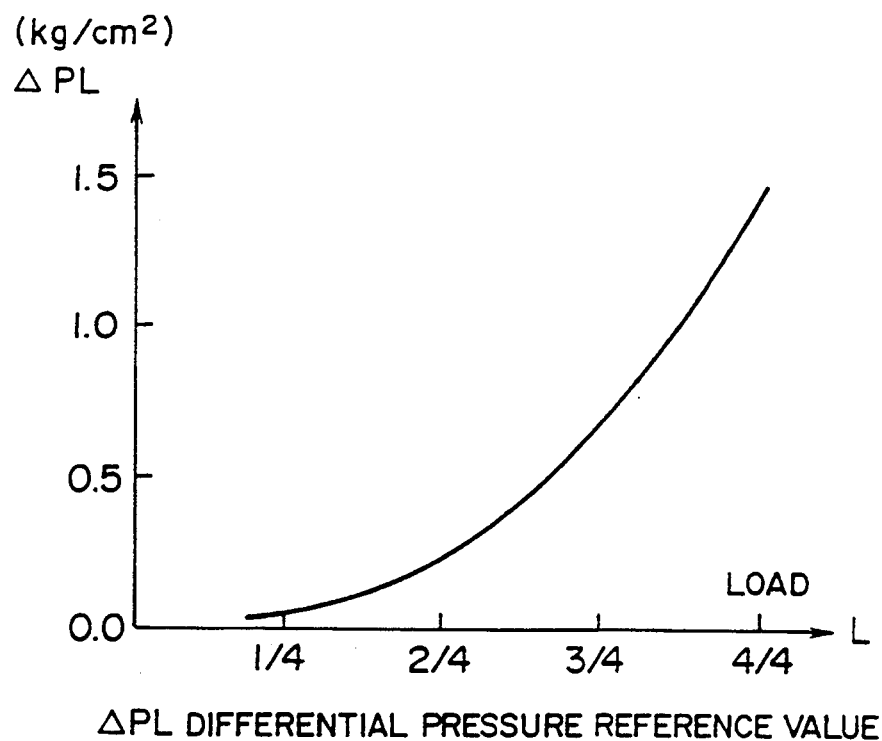
ΔPL DIFFERENTIAL PRESSURE REFERENCE VALUE
F I G. 5
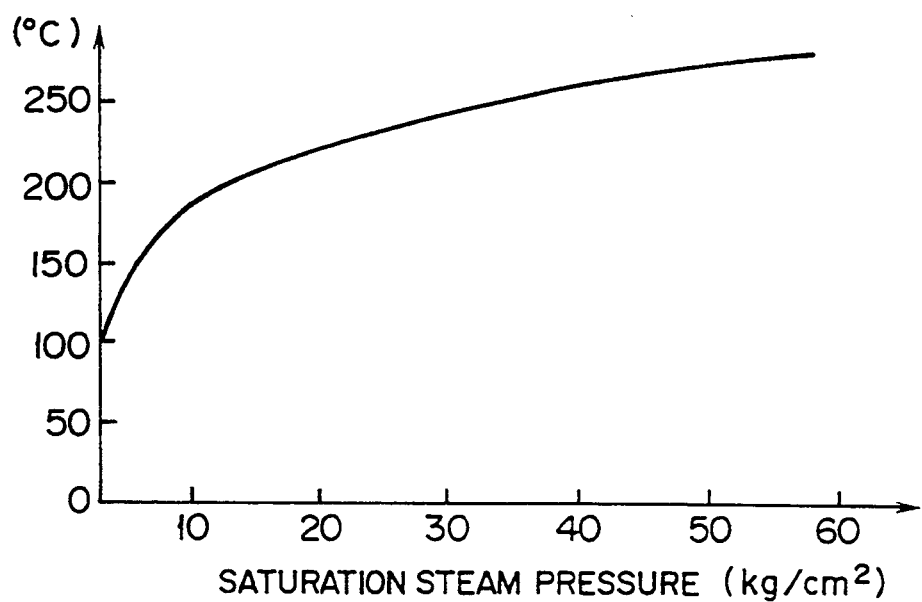
F I G. 6

ΔT1L REFERENCE VALUE

ΔT2L REFERENCE VALUE

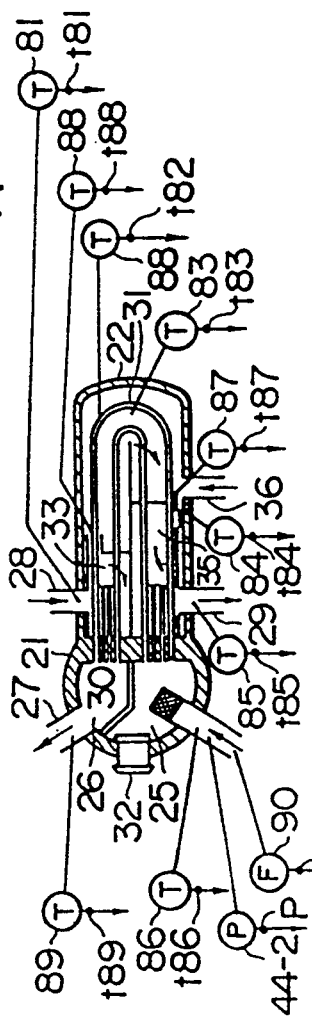
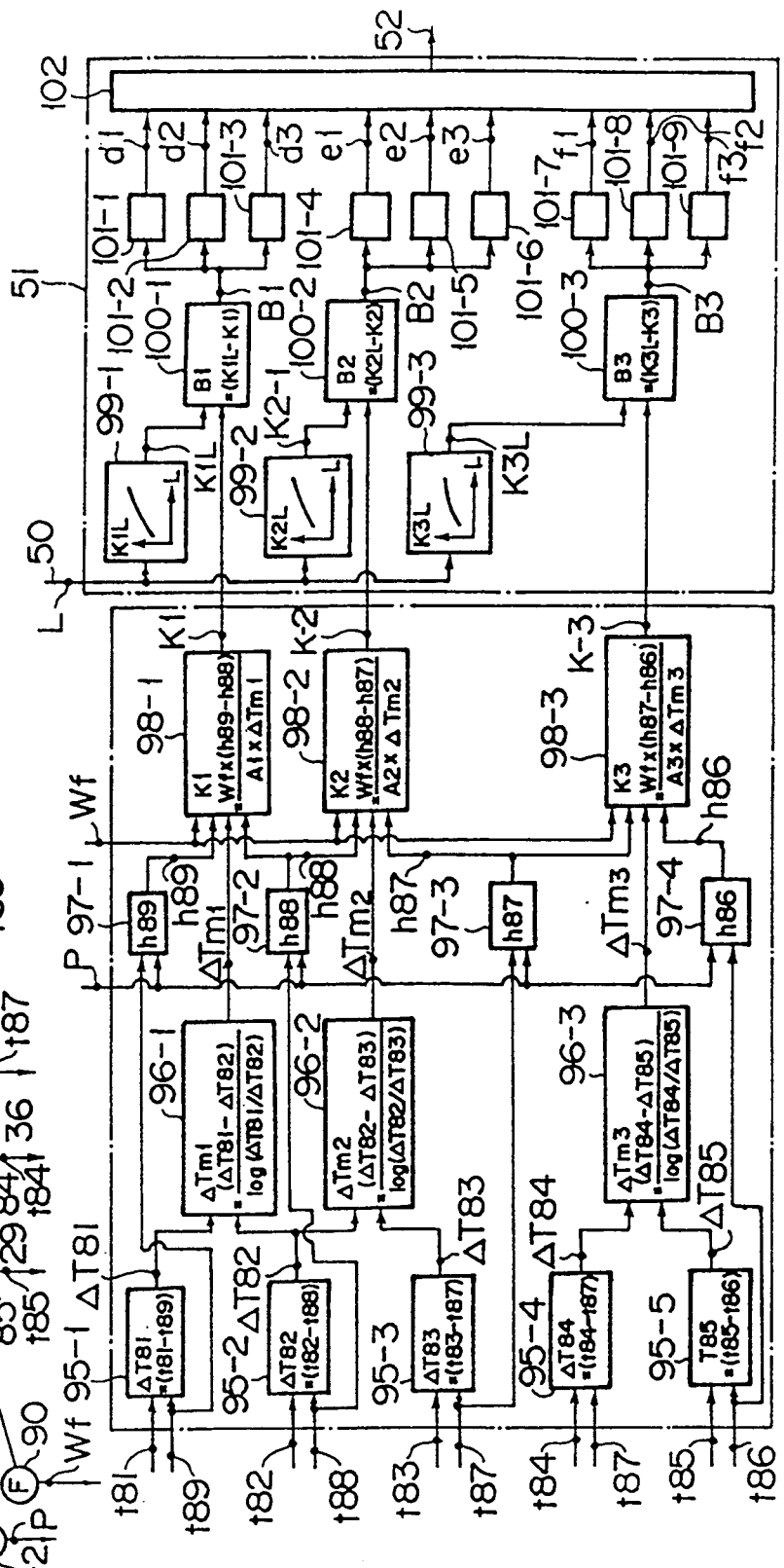
FIG. 9A
FIG. 9B

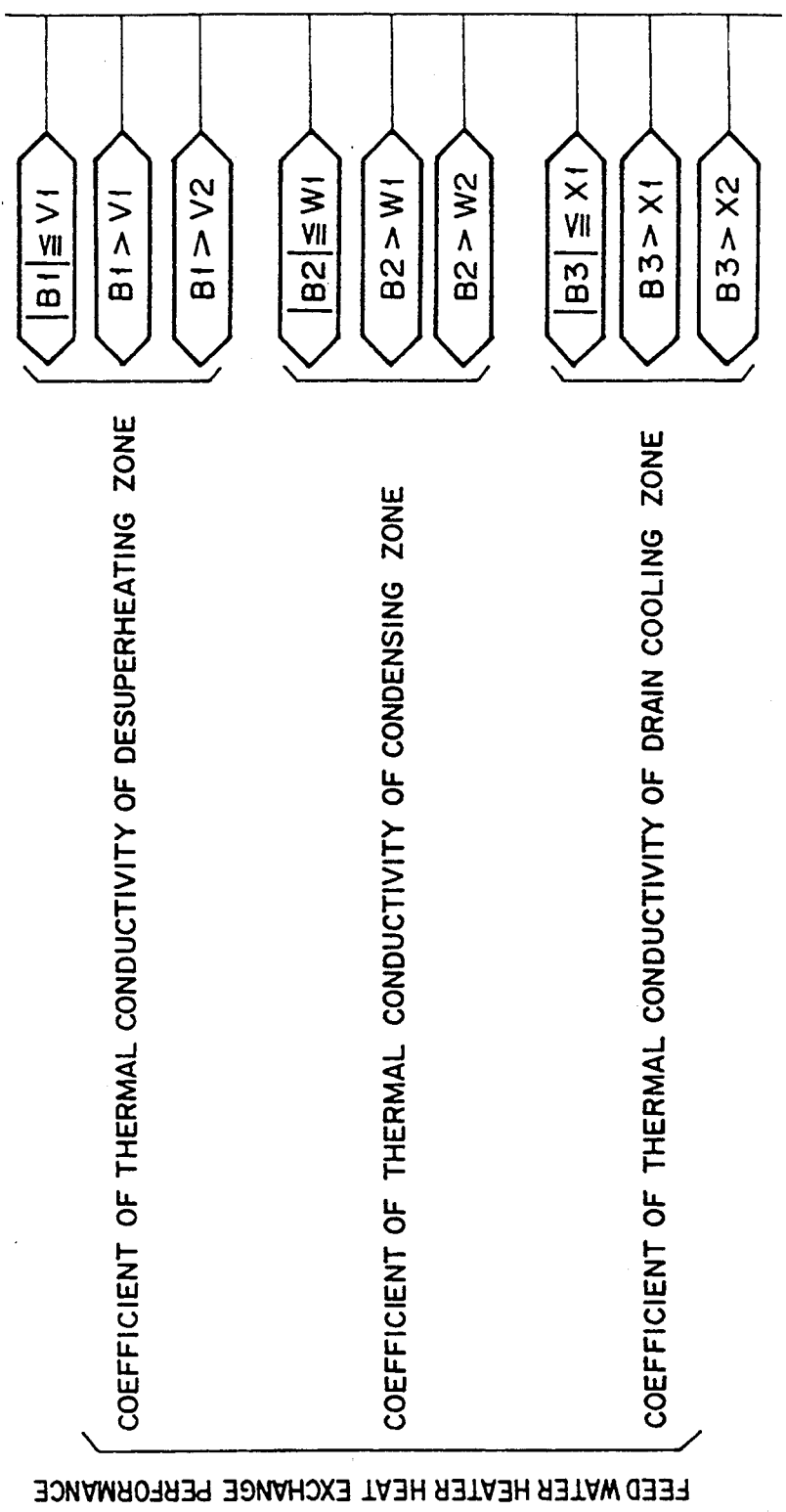

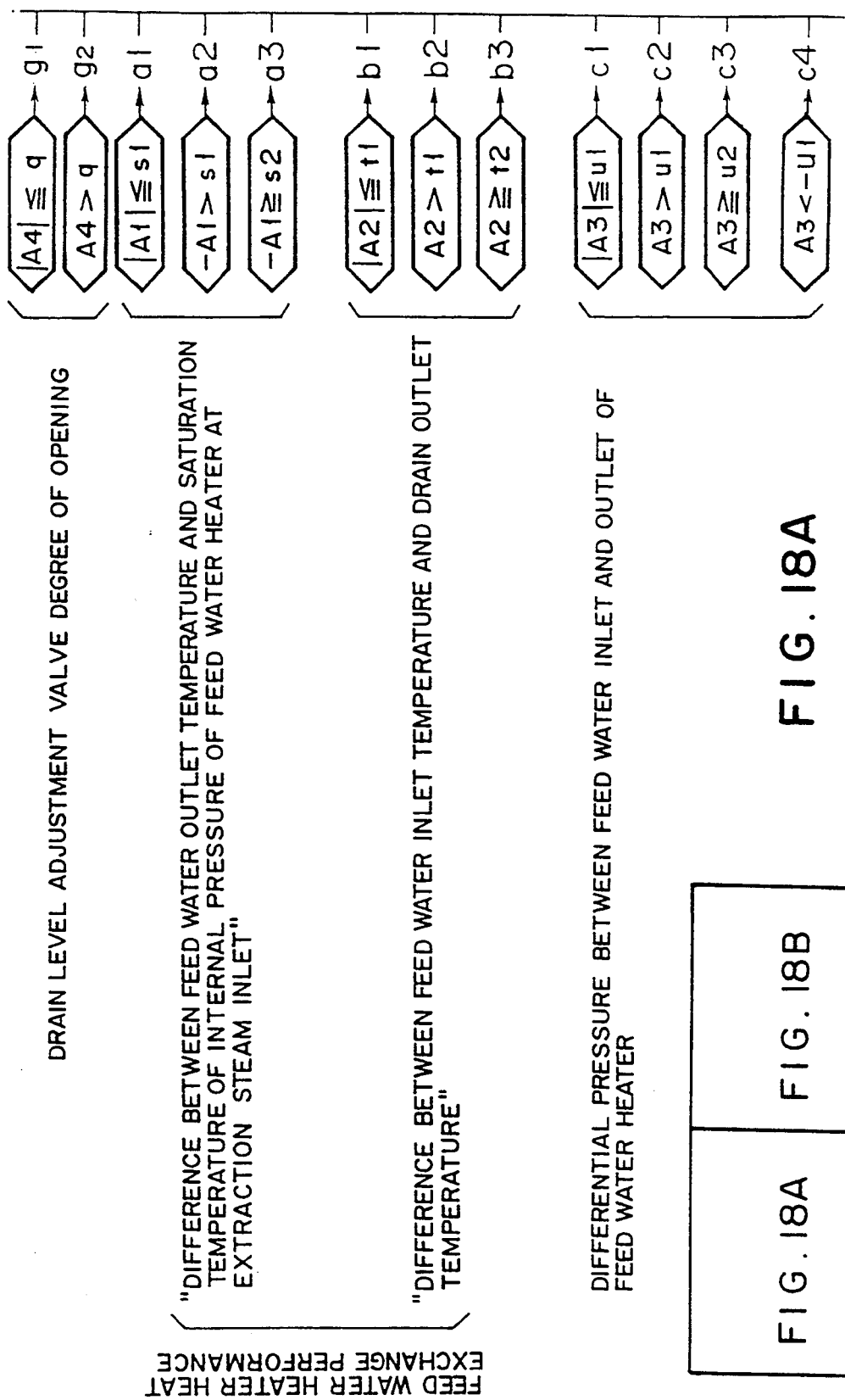

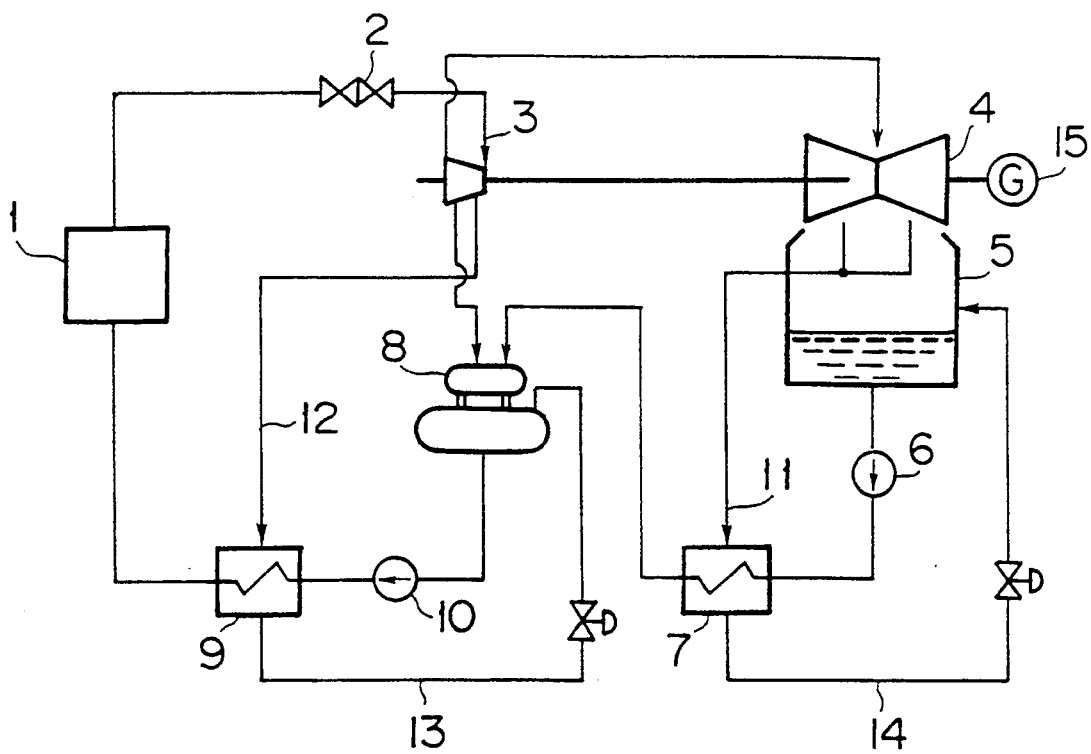
F I G. 31
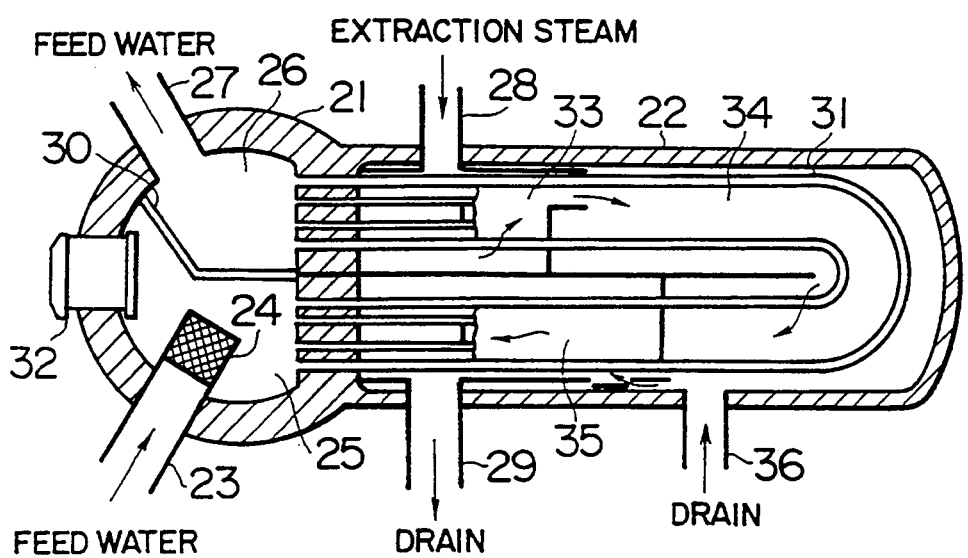
F I G. 32

HEAT EXCHANGER ABNORMALITY MONITORING SYSTEM

BACKGROUND OF THE INVENTION

The present invention relates to a heat exchanger abnormality monitoring system that can monitor the presence of scale accretion to flow distribution devices and the outer and inner surfaces of heat exchange tubes, as well as other abnormalities in accordance with necessity, provided in a heat exchanger for feed water heaters and the like installed in feed water or condensate water systems of power generation plants.

In general, feed water or condensate water systems of power generation plants have heat exchangers, that is feed water heaters installed in order to heat feed water or condensate water by the steam discharged from steam turbines.

The following is a general description of such a feed water heater, with reference to the thermal power generation plant shown in FIG. 31.

The steam created by a boiler 1 is led to a high-pressure turbine via a steam stop valve and an incrementation-reduction valve 2, and after it has fulfilled its function as a drive source, is led to a low-pressure turbine 4 where it functions as a drive source once again, and is cooled by the cold water in a condenser 5 to become condensate. The high-pressure turbine 3 and the low-pressure turbine 4 that are driven by the steam drive load of the generators 15, and the like.

In addition, the condensate stored in the condenser 5 is pressure fed by a circulation pump 6 and is supplied to a deaerator 8 via a feed water heater 7. The condensate (which after this is termed 'feed water') that is supplied to the deaerator 8 is pressure fed by the feed pump 10 and is supplied to the boiler 1 via a feed water heater, and is heated in the boiler once again to become steam.

Moreover, the extracted steam that is led via the steam extraction pipes 11,12 from the intermediate stages of the high-pressure turbine 3 and the low-pressure turbine 4 is led to the feed water heaters 7,9 described above and the condensate and the feed water are heated by the extracted steam with condensate and feed water of a higher temperature being supplied to the boiler 1.

Moreover, after the feed water and the condensate water have been heated, the extracted steam is drained and the drain inside the feed water heater 9 is led to the deaerator 8 via the drain pipe 13, and the drain inside the feed water heater 7 is led to the condenser 5 via the drain pipe 14 and flows into the condensate.

FIG. 32 shows one example of a feed water heater used in a thermal power generation plant having such a configuration. Moreover, the previous description was given in terms of heating the condensate and the feed water but for either of the feed water heaters, the process fluid in the power generation plant is generally water, and this process fluid and the extracted steam for heating only have different pressures and temperatures and so in FIG. 32, the description will be given in terms of the example of a feed water heater 9 for feed water.

The feed water heater 9 is largely configured from the two portions of a water chamber portion 21 and a feed water heater unit 22.

The water chamber portion 21 is divided by a water chamber partition plate 30 into an inlet-side water chamber 25 and an outlet-side water chamber 26. These inlet-side water chamber 25 and outlet-side water chamber 26 are linked by the many heat exchange tubes 31 that are disposed inside the feed water heater unit 22. In order to distribute the flow of feed water to the inlet-side water chamber 25, the feed water inlet portion 23 has mounted to it a flow distribution device 24 provided with small holes for the many feed water supply paths. In addition, the water chamber portion 21 has a manhole 32 mounted to it in order to allow inspection and maintenance of the inside of the water chamber drain cooling zone when the power generation plant is stopped.

In such a feed water heater 9, the feed water that is pressure fed by the feed water pump 10 passes from the feed water inlet portion 23 of the water chamber portion 21 and then through the flow distribution device 24 and flows into the inlet-side water chamber 25. The feed water that flows into the inlet-side water chamber 25 flows into the many heat exchange tubes 31 that are provided inside the feed water heater unit 22 and flows out to the outlet side water chamber 26, through the feed water outlet portion 27 and is fed to the boiler 1.

The vicinity of the feed water heater unit 22 through which the extraction steam passes is known as the desuperheating zone 33, and the vicinity where the drain flows from the feed water heater is known as the drain cooling zone 35, and the other portions are known as the condensing zone 34. However, the extracted steam flows from the extracted steam inlet portion 28 to the desuperheating zone 33 and heat exchange with the feed water that flows inside the heat exchange tubes 31 cools it so that it becomes saturated steam which then condenses in the condensing zone 34 to become high temperature water which is drained.

After this, this drain is further cooled in the drain cooling zone 35 by heat exchange with the feed water that flows inside the heat exchange tubes 31, becomes low-temperature drain and flows from the drain outlet portion 29 of the feed water heater unit 22 and flows into the deaerator 8 via the drain pipe 13. On the other hand, the feed water inside the heat exchange tubes 31 flows from the inlet-side water chamber 25 to the outlet-side water chamber 26 and is gradually superheated along the way.

Moreover, depending upon the power generation plant, there are instances where a plural number of feed water heaters are disposed in series and respectively for feed water and for condensate water but in many cases such as these, the drain that flows from the drain outlet portion 29 of the feed water heater that is closest to the side of the boiler, is supplied to the drain inlet portion 36 provided to the condensing zone in the vicinity of the drain cooling zone of the feed water heater closest to the condenser. In such a feed water heater, the drain that is the result of cooling of the extracted steam that flows to that feed water heater after the vicinity of the drain cooling zone, and the feed water that flows inside the heat exchange tubes by the drain that flows in from the feed water heater on the side of the boiler, are heated.

Also, there are many cases where general carbon steel pipes are used as the flow distribution device 24 and the heat exchange tubes 31 and the like. When such a feed water heater is operated for extended periods of time, the iron component in the feed water accretes to the flow distribution devices and to the inner surfaces of the carbon-steel tubes that are in contact with the feed water, to result in the generation of a scale membrane of ferrous oxide and which is known as magnetite.

This magnetite scale membrane adheres strongly and is formed thinly over the entire inner surface of the steel pipes and is effective in protecting and preventing the corrosion of the steel tubes. However, when this scale membrane accretes thickly on the inner surfaces of the many small holes that are provided to the flow distribution device 24 and the inner surfaces of the steel tubes, that is, in the feed water flow path, the feed water flow path area is reduced and so there is a relatively larger pressure loss for the feed water in the flow distribution device 24 and the steel tubes and the like when compared to that at the same flow rate when the scale membrane is relatively thin. More specifically, there is an increase in the differential pressure of the feed water pressure on the outlet side and the inlet side of the flow distribution device 24 and the differential pressure of the feed water pressure on the outlet side and the inlet side of the steel tubes. When the thickness of this scale membrane becomes excessive, the differential pressure on the outlet of the flow distribution device 24 becomes excessive to give rise to the fear of destruction of the flow distribution device 24, and if the differential pressure of the outlet of the steel tubes, that is, the inlet-side water chamber 25 and the outlet-side water chamber 26 becomes large, there is the danger of the destruction of the water chamber partition plate 30.

In addition, the feed water flow rate to the boiler 1 is determined by the increase or decrease in the turbine load of the power generators and the like but when the feed water flow rate corresponding to the load of the generators is pressure fed to the boiler 1 by the feed water pump 10 and via the feed water heater 9, there is a feed water pressure loss in the steel tubes and the flow distribution devices which is greater when there is a thick scale membrane than when there is a thin scale membrane and the discharge pressure of the same pump must be increased by raising the speed of the feed water pump, to result in the problem of an increase in the pump load.

As has been described above, heat exchange between the drain and the extracted steam and the feed water is performed via the tube walls in the heat exchange tubes 31 but there is the problem that the thicker the accretion of a scale membrane on the inner surfaces of the heat exchange tubes, the lower the heat exchange efficiency between the drain and the extracted steam and the feed water in the feed water heater.

Furthermore, in feed water heaters for which the temperature of the feed water is relatively low, the magnetite scale membrane that is formed is relatively weak and so it is easy to flake and peel off. On the other hand, for feed water heaters that operate with relatively high-temperature feed water at temperatures in the two hundreds (°C.), the magnetite scale membrane is relatively firmly attached. However, even in cases such as these, mechanical shock and the like caused by rapid changes of the flow speed, or turbulence of the feed water flowing inside the feed water heater, or thermal shock caused by differences in the coefficients of thermal expansion and the coefficient of heat transmission between the scale membrane and the flow distribution devices and the steel tubes and resulting from changes in the load and from stopping and starting of the power generation plant can generate local peeling or flaking of the magnetite scale membrane and the scale membrane that is peeled off moves to the downstream side by the flow of the feed water and collects in the feed water flow path portion to cause the problem of the feed water pressure loss increasing even further. Not only this, the local flaking of the scale membrane causes the problem of the generation of channel or hole corrosion in the steel tubes.

In this manner, the magnetite scale membrane is effective while there is the generation of a thin layer of scale across the entire inner surface of the steel tubes but when this thickness is excessive, it is necessary to perform work to remove the scale membrane since various types of problems as described above occur.

This work to remove the scale membrane if it has formed in the flow distribution devices, can be performed by opening the manhole 32 of the water chamber portion 21 while the power generation plant is stopped, and by then removing and performing cleaning work for the flow distribution device 24. This is comparatively simple work but for the scale membrane that has generated in the inner surface of the steel tubes, not only does the manhole 32 of the water chamber portion 21 have to be opened while the power generation plant is stopped, but it is also necessary to remove the water chamber partition plate 30 and to insert a high pressure water flow into the steel tubes and perform cleaning, so that it is necessary to reattach the water chamber partition plate 30 by welding or the like and this of necessity involves much troublesome related work.

It is therefore extremely effective to monitor the degree to which the scale membrane is generating, particularly if the scale membrane is excessive.

However, in the past, there has been no effective apparatus that can monitor the status of generation of the magnetite scale membrane that attaches to the steel tube and the flow distribution devices, while the power generation plant is operating.

Depending on the power generation plant, the differential pressure of the feed water pressure in the feed water outlet portion 27 and the feed water inlet portion 23 of the feed water heater is periodically measured by a differential pressure gauge and when that absolute value has increased to greater than a value greater than the previously measured value, work to remove the scale membrane is performed since the thickness of the scale membrane has increased to become excessive.

However, when there is monitoring using a differential pressure gauge, the measurement is difficult and cannot be considered to be reliable. More specifically, in the case of a specific example of a feed water heater for a power generation plant, the feed water inlet portion pressure of the feed water heater installed between a feed water pump and a boiler is approximately 300 Kgf/cm$^2$ and the feed water outlet portion pressure is approximately 298.5 Kgf/cm$^2$ when there is only a thin (acceptable) scale membrane (while the differential pressure gauge shows approximately 1.5 Kgf/cm$^2$) and is approximately 297 Kgf/cm$^2$ when there is an excessively thick generation of scale membrane. This means that the pressure of the feed water pressure that has to be measured is only in the small range of 0.5 to 1.0%. Also, the respective feed water pressures at the feed water inlet portion 23 and the feed water outlet portion 27 are always fluctuating minutely (in what is commonly termed "pulsations") and despite the fact that the feed water pressure is normally derived as:

feed water inlet portion pressure > feed water outlet portion pressure.

There are also occasions when the differential pressure of the feed water pressure indicated by differential pressure measurement is a negative value shown by:

feed water inlet portion pressure < feed water outlet portion pressure.

Also, depending on the increase or decrease of the load at the power generation plant (in other words, to increase or decrease the feed water rate) even if the thickness of the scale membrane is the same, this differential pressure value changes greatly and so if a comparison of the differential pressure is not performed for when the feed water flow rate is the same value, it is not possible to make a judgment whether the thickness of the scale membrane is excessive or not. Accordingly, the differential pressure had to be measured and compared to the same timing as the load (feed water flow rate) value for when there are differential pressure measurements for when the past scale membrane was thin (acceptable).

In addition, because of the structure of the feed water heater, the water chamber partition plate generally has a lesser strength with respect to differential pressure than does the flow distribution devices and is easily broken even by small differential pressures so that, if possible, the differential pressure should be monitored for each of the flow distribution devices and the steel tubes. But performing this means that the differential pressure of the feed water pressure in the inlet side water chamber and the feed water output portion or the output side water chamber, and the differential pressure of the feed water pressure in the feed water inlet portion and the inlet side water chamber has to be monitored. More specifically, in addition to the feed water outlet portion and the feed water inlet portion, the feed water pressure at the inlet side water chamber also has to be measured. But in general, the structure of the intake side water chamber portion is complex, and so it is not easy to install piping for pressure measurement at this portion. Furthermore, since the internal structure in the inlet side water chamber portion and the outlet side water chamber portion is also complex, there is the tendency for disturbances to occur inside, with pulsations becoming larger, the larger these disturbances are. In addition, the differential pressure of the feed water pressure that has to be measured is also smaller than the differential pressure of the feed water outlet portion pressure and the feed water inlet portion pressure as has been described above, and this means that the measurement results that are obtained have even less reliability than those of the case described above and it is not possible to determine which portions have an excessive thickness of scale membrane generation.

On the other hand, depending upon the power generation plant, the degree of heat exchange between the drain and the extracted steam of the feed water heater is monitored via a steel tube. When this degree of heat exchange drops, it is judged that there is the generation of an excessive thickness of scale membrane inside the steel tubes and work to remove this scale membrane has been performed.

However, when the degree of heat exchange is monitored, the difference between the feed water temperature at the feed water outlet portion and the extracted steam saturation temperature of the feed water heater, and the difference between the feed water temperature of the feed water outlet portion, and the drain temperature of the feed water heater are generally measured, but when the temperature difference between these two, when there is the generation of a thick scale membrane, changes by approximately 3° C. when compared when there is only the generation of a thin scale membrane on the inner surfaces of the tubes. In addition, in a power generation plant, a thermocouple or a temperature measuring resistor is generally used in the temperature detector to measure the temperature of these portions. But the measurement method used in these temperature detectors is such that a measurement error due to the amount of time that has elapsed since installation changes by several degrees C. and so this method has been regarded as unreliable.

Moreover, the description so far has been for only the generation of scale membrane in the feed water side of the feed water heater, but in reality, a small amount of foreign matter included in the extracted steam attaches to the outer surfaces of the steel tubes when the power generation plant has been in operation for an extended period of time and as a result, the heat exchange performance drops (so that the difference between the feed water temperature at the feed water outlet portion and the extracted steam saturation temperature of the feed water heater, and the difference between the feed water temperature of the feed water outlet portion, and the drain temperature of the feed water heater outlet changes by about several degrees when compared to the normal situation).

In this manner, when there is the adhesion of foreign matter to the outer surfaces of the steel tubes, this differential pressure causes the partial destruction of the feed water heater but when this amount becomes excessive, the degree of heat exchange with the feed water heater drops so that it is not desirable to remove the foreign matter.

However, in cases such as these, it is unclear whether the drop in the degree of heat exchange is due to the accretion of scale membrane on the outer surface or the inner surface of the steel tube. So, when opening the manhole of the water chamber portion is performed as part of the work of removing the scale membrane on the inner surface of the steel tubes and the flow distribution devices, there are occasions when it is necessary to remove foreign matter on the extracted steam side but not on the feed water side. In addition, in the same manner as the method of using differential pressure measurements, even if the thickness of the scale membrane is the same, increases and decreases in the load at the power generation plant (that is, increases and decreases the feed water flow) cause the degree of heat exchange to change greatly. So, comparison of the degree of heat exchange must be performed when the load is the same value (feed water flow). Accordingly, it is necessary to measure and compare the degree of heat exchange at the same timing as the load value (feed water flow), at the time of measurement of the degree of heat exchange when there was a thin scale membrane in the past.

In addition, for as long as there is no generation of scale membrane on the outer or inner surfaces of the steel tube, this method has the disadvantage that there is no change in the degree of heat exchange no matter what the degree of excessive thickness of scale is with respect to the flow distribution devices. It is also not possible to determine the position where there is an excessive thickness of scale membrane.

Therefore, there are many cases where such measurement is not performed and where the power generation plant is operated for a predetermined period and then removal of the scale membrane is periodically performed.

However, in these cases, the manhole of the water chamber portion is opened and the flow distribution devices are removed, and the water chamber partition is removed and high-pressure water or the like is introduced into the steel tubes and cleaning is performed so that in some cases there is the inconvenience of finally knowing that there is no generation of an excessive thickness of scale membrane.

However, the major parts where there is scale accretion in and around the feed water heater are the inner and outer surfaces of the heat exchange tubes, the flow distribution devices and the drain level adjustment valve of the feed water heater.

The drain level adjustment valve of the feed water heater is installed in the drain pipe connected to the feed water heater drain outlet portion for the purpose of controlling the drain water level of the drain cooling zone of the feed water heater to a constant value, with the drain level of the drain cooling zone being detected, with control of this water level being performed to a predetermined value by opening and close control performed by the receiving of output signals of the drain water level adjustment gauge of the feed water heater, and the drain flow rate that flows from the feed water heater being controlled so that as a result, the water level of the drain that collects in the drain cooling zone inside the feed water heater is controlled at a constant level.

There are occasions where there is the accretion of a scale membrane to this drain level adjustment valve and the following problems occur when this accretion is excessive.

(1) When there is scale membrane accretion in the drain flow path portion and the drain flow path area is reduced, then even if the degree of opening of the drain water level adjustment valve is the same, then there is a reduced drain flow when compared to no scale accretion on the drain.

(2) When there is scale membrane accretion the drain flow path portion, there is a change in the flow characteristics of the drain water level adjustment valve, and control deteriorates.

(3) When there is an accretion of scale to an excessive thickness and the clearance of each of the portions of the drain water level adjustment valve is reduced, then the motion of this adjustment valve deteriorates and sticks on occasions.

When there is formation of a scale membrane having excessive thickness on the drain water level adjustment valve, it is desirable that this be detected as early as possible. If necessary, the drain water level adjustment valve is disassembled, and the accreted scale membrane removed.

However, with conventional technology, it has not been possible to detect the accretion of a scale membrane to the drain adjustment valve, while the power generation plant is still operating.

Therefore, when it is not possible to complete the scale removal work during the period of the periodic inspection or when there must be additional scale removal work for the drain water level adjustment valve once it is known that there is an excessive thickness of scale membrane accreted after the disassembly of the drain water level adjustment valve when there is the periodic inspection when the power generation plant is not operating, the removal of the scale is performed at the next periodic inspection. Until then, the plant is operated with the scale membrane present. There are many occasions when such operation of the plant cannot be avoided and this results in changes in the periodic inspection processes, and the expenses involved.

The problems that can occur in feed water apparatus are not only an excessive thickness of scale membrane attached to each of the portions of the feed water heater as has been described above, but also leaks in the tubes for heat exchange, problems of destruction of the water chamber partition plate that partitions the outlet side water chamber and the inlet side water chamber for the feed water, and problems of extracted steam being taken into the drain cooling zone or the short path of the drain due to plate destruction around the drain cooling zone of the feed water heater.

The problem of the generation of a leak in the tubes for heat exchange of the feed water heater is, more specifically, the generation of pinholes in one portion of the tubes of the heat exchanger or the problems of high pressure feed water from the connections between the heat exchanger tubes and the materials configuring the feed water heater, leaking to inside the low-pressure feed water heater unit, that is, the side of the drain or the extracted steam for heating. In cases such as these, the leak amount may be only small when the leak is first discovered but since the water is high pressure, the leak place enlarges in a relatively short time. Moreover, this leaked feed water becomes the same as the drain and is extracted from the feed water heater drain outlet portion via the drain water level adjustment valve but along with an increase in the leaking feed water flow, there is an increase in the drain amount that must be extracted from the feed water heater and so there is no alternative but to increase the degree of opening of the drain water level adjustment valve. In this case, when there is an increase in the leak feed water amount to a degree which is greater than of the drain amount that can be extracted when the drain water level adjustment valve is fully open, the drain from that feed water heater cannot be extracted and so the drain inside the feed water heater becomes full. Ultimately, the drain flows from the extracted steam inlet into either the high-pressure turbine or the low-pressure turbine via the extracted steam tubes.

Conditions such as this are generally known as 'water induction' and when water induction generates in the low-pressure turbine or the high-pressure turbine that is driven by high-temperature steam, the materials of the high-pressure or the low pressure turbine that is at high temperature are quickly cooled by the relatively low-temperature drain and so there is the generation of cracking due to thermal stress and the consequent danger of a large-scale failure.

Accordingly, leaks in the heat exchange tubes must be detected at as early a stage as possible and the operation of the feed water heater stopped quickly and repairs performed to the connections between the heat exchange tubes and the materials of the water chamber, or the inlet portion and the outlet portions of heat exchange tubes in which there are pinholes or blocked passages and repairs must be performed so that there is no further leakage of feed water and then the feed water heater can be operated once again.

However, the detection of whether or not there is a leak in the turbines of the heat exchanger is conventionally performed by a judgement on the basis of an inspector listening by ear for the sound of a leak when there is the leak of feed water at high pressure. But feed water heaters normally have the sound of feed water flowing in and flowing out, and the sound of the flowing of extracted steam for heating. Also, these sounds change in quality along with changes in the load of the power generation plant. In addition to these, there are also cases where noise from many types of power generation plant equipment around the feed water heaters is also transmitted and it is difficult and requires much experience to distinguish these sounds from the specific sound that leaking water makes.

Therefore, instead of making a judgement on the basis of listening by a trained ear, an acoustic sensor such as an AE (acoustic emission) sensor or a acceleration type of acoustic sensor is used to detect the sound that is transmitted to the feed water heater, and this detected sound has signal processing such as frequency analysis of the detected sound performed for it so that only the sounds that are thought to be the sound of leaking feed water are extracted and detected from the sounds transmitted inside the feed water heater.

However, the nature of the sound of leaking feed water changes according to whether it is a leak from a hole or the type of opening, and according to whether it is a leak in the connectors between the water chamber, a leak in the superheating zone or a leak in the condenser drain cooling zone. Also, transmitted sounds other than the sounds of leaks, such as the sound of the flowing in of feed water or extracted steam, also change in complex ways, depending upon the load conditions of the power generation plant. Even if an apparatus such as has been described above is used, it is still difficult to reliably detect the appropriate sounds. In addition, it is still not possible to determine the places where the leaks are occurring.

In addition, there is no method available where it is possible to detect, while the power generation plant is operating, the short path of the drain or the inlet of extracted steam to the drain cooling zone due to the destruction of the water chamber partition plate of the feed water or destruction of the drain cooling zone enclosing plate.

Therefore, when there is an abnormal value indicated for the temperature of any of the portions when a monitor for the monitoring of the drain outlet temperature, the outlet/inlet feed water temperature of the feed water heater is exhibited, the trouble spot has been detected by the inspection of each portion by trial and error. In addition, there is the method of judgment trouble by the monitoring of the heat exchange performance of the feed water heater but when there is only monitoring of the heat exchange performance such as when for example, there is the destruction of the water chamber partition plate, it is not possible to discriminate between when there is the accretion of scale on the inner surface of the heat exchange tubes.

Still furthermore, there are also occasions when, depending upon the power generation plant, the discharge side of the feed water pump 10 branches into two or three branches (a plural number) and there are two or three (a plural number) feed water heaters installed in parallel, those output sides are again recombined in a pipe system that has a pressure feed to the boiler 1. With piping systems such as these, if the structures, performances and the like of the feed water heaters installed in parallel are exactly the same and if the flow path resistances are also exactly the same when there is the flow of fluid in the piping system, then the feed water amount that flows to the feed water heaters installed in parallel becomes exactly the same value ($\frac{1}{2}$ or $\frac{1}{3}$ of the total feed water flow). Accordingly, the extracted steam amounts and the drain amounts that flow out to each of the feed water heaters also become exactly the same value.

However, when there is the accretion of scale membrane in amounts that differ completely for the flow distribution devices or the heat exchange tubes, with respect to the feed water heaters that are installed in parallel, differences occur in the flow path resistances with respect to the feed water for the respective feed water heaters and the feed water flows flowing into the respective feed water heaters are no longer the same. When this occurs, for example, if the heat exchange performances of the feed water heaters is the same, there are differences in the feed water outlet temperatures and the drain outlet temperatures and so it becomes difficult to determine the presence of abnormalities in the feed water heaters, the presence of scale accretion to the drain water level adjustment valve, or the flow distribution devices, or the inner or outer surface of the tubes for the heat exchanger.

SUMMARY OF THE INVENTION

It is an object of the present invention to provide an abnormality monitoring apparatus for a heat exchanger that, for any arbitrary power generation plant load, can simultaneously monitor the degree of opening of a drain water level adjustment valve in accordance with necessity, and that can simultaneously monitor both the differential pressure of the feed water outlet portion pressure, the feed water inlet portion pressure and the heat exchange performance of the feed water heater, and can determine the inlet of extracted steam to the drain cooling zone or the short path of the drain due to the destruction of the drain cooling portion enclosuring plate of the heat exchanger or destruction of the water chamber partition plate, the presence of leaks in the heat exchanger tubes, and the presence of scale accretion on the drain water level adjustment valves.

In order to achieve the objectives described above, the heat exchanger abnormality monitoring apparatus of the invention in a first aspect thereof is provided with various types of process measuring units, a differential pressure calculation unit, a performance calculation unit and a judgment portion. The monitoring of both the heat exchange performance of the heat exchanger and the differential pressure of the feed water pressure at the outlet and inlet of the heat exchanger enables the determination of whether scale accretion is on the inner surface or the outer surface of the heat exchange tubes, or in the feed water flow path or some place other than the tubes for the heat exchanger.

The heat exchanger abnormally monitoring apparatus of the invention in a second aspect thereof is that as described above is the first in which the simultaneous monitoring of the degree of opening of the drain water level adjustment valve enables the judgment of the presence of extracted steam to the drain cooling zone of the short path due to the destruction of the heat exchanger drain cooling zone enclosuring plate or the destruction of the water chamber partition plate.

Moreover, the implementation of these inventions is described below.

The heat exchanger abnormality monitoring apparatus has the feed water inlet pressure measuring unit and the feed water outlet pressure measuring unit installed at a place where the pulsation of the feed water outlet and the feed water inlet of the heat exchanger is as small as possible.

The heat exchanger abnormality monitoring apparatus has the feed water heater of the heat exchanger as the object, and should monitor both the "difference between the feed water outlet temperature and the saturated temperature inside the feed water heater at the extracted steam outlet" and the "difference between the feed water inlet temperature and the drain outlet temperature".

The heat exchanger abnormality monitoring apparatus has a means of monitoring the heat exchange performance that calculates the ease (such as the ratio of thermal conductivity) via the heat exchange tubes for each of the respective portions, using the values obtained for the temperature of the drain and the extracted steam, and the feed water that flows into, at least, portions of the superheating zone, the condensing zone, the drain cooling zone, and uses these results to monitor heat exchange performance.

The heat exchanger abnormality monitoring apparatus does not measure the pressure and temperature of the feed water inside the heat exchange tubes at the condensing zone outlet and the drain cooling zone, but instead uses the measured valves for other process values to calculate the feed water temperature and uses this to monitor the heat exchange performance.

The heat exchanger abnormality monitoring apparatus uses a value when there is the normal accretion of scale membrane to each of the portions of a heat exchanger as the reference value to monitor the heat exchange performance of the heat exchanger and the differential pressure of the feed water pressure between the inlet and outlet of the heat exchanger, and then compares these values to the measured values, so that abnormalities can be determined when there are relative changes in the two.

By obtaining reference values for each load (or each feed water flow) of the power generation plant and by storing a relationship equation for them, the heat exchanger abnormality monitoring apparatus obtains reference values corresponding to the loads (or each of the feed water flow amounts) from those values when there is a change in the load, and uses relative changes in these to make a determination.

The heat exchanger abnormality monitoring apparatus monitors the degree of opening of the drain water level adjustment valve or a corresponding quantity to also enable judgment of operating abnormalities of the drain water level adjustment valve and sticking of the drain water level adjustment valve.

The heat exchanger abnormality monitoring apparatus monitors the imbalance of the inlet feed water flow to the respective feed water heaters from the conditions of change of the differential pressure obtained by monitoring the differential pressures between pairs of outlet sides of the orifice plate or flow nozzles, and feed water inlet valves installed respectively on the feed water inlet sides.

According to the heat exchanger scale accretion monitoring apparatus of the present invention and having the configuration as described above, it is possible to accurately detect the accretion of a scale membrane to the steel tubes, the flow distribution devices or the drain water level adjustment valve, the position of accretion and also various other types of abnormalities.

As has been described above, using the present invention, it is possible to judge whether the location of the accretion of scale membrane is to the inner surfaces of heat exchanger tubes, or to the flow distribution devices and the feed water flow path or some place other than this, or whether it is to the external surface of the heat exchanger tubes by simply measuring the differential pressure of the pressure at the feed water outlet portion and the feed water inlet portion where there is little pulsation, for the differential pressure of the feed water flow path portion of a heat exchanger of a feed water heater or the like. Still furthermore, in the case of a feed water heater, it is possible to judge whether the accretion of scale membrane to the heat exchanger tubes is to the desuperheating zone or the drain cooling portion, and also to judge the amount of accretion of scale membrane.

In addition, it is also possible to judge the presence of a relative change of the reference values corresponding to a change in the load (FIG. flow) of the power generation plant.

In addition, according to the present invention, when there is a place that is easily destroyed by a comparatively small differential pressure and the generation of the scale membrane to the inner surface of the heat exchanger tubes, this can be judged by "slight abnormality" for both the feed water inlet and outlet differential pressure and the heat exchange performance, and when there are places where there are no troubles due to differential pressure or the accretion of scale membrane to the outer surfaces of the heat exchanger tubes, it is possible to judge "abnormality" of the heat exchanger performance, and when there is a place that is difficult to be destroyed by relatively large differential pressure of the accretion of scale membrane to the flow distribution devices and the like, it is possible to judge this an "abnormality" in the differential pressure of the feed water inlet and outlet, so it is possible to obtain results of high reliability.

Accordingly, there is also the effect of being able to perform the cleaning work to remove the scale membrane at appropriate times. In addition, the scale membrane removal work can be performed when appropriate and so trouble such as the destruction of the heat exchange tubes and the flow distribution devices due to differential pressure can be prevented and the drop of the heat exchange performance of the heat exchangers can also be prevented. Still furthermore, it is possible to prevent trouble such as the rise of the load of the feed water pump due to the accretion of an excessive thickness of scale membrane with respect to the feed water flow path.

In the second invention, in addition to the effects described above, it is also possible to judge the presence of accretion of excessive scale membrane to each of the portions of the feed water heater, the presence of scale accretion to the drain level adjustment valve, sticking and other misoperation of the drain level adjustment valve suitable and without disassembly of each portion. Accordingly, the drain level adjustment valve can be inspected and maintained at suitable intervals.

In addition, when there is an occurrence of a leak in the heat exchanger tubes, this can be detected at an early stage and the judgment of the place of the leak performed. Furthermore, it is also possible to quickly detect when there is a short path due to the destruction of the enclosure of the drain cooling zone and the destruction of the water chamber partition plate or the intake of extraction steam to the drain cooling zone. In addition, the present invention can be suitably applied in cases when there are a plural number of heat exchangers disposed in parallel.

BRIEF DESCRIPTION OF THE DRAWINGS

FIG. 5 is a graph showing the relationship between the differential pressure of the feed water inlet and outlet portions, and the load of the power generation plant when there is the normal accretion of scale membrane;

FIG. 6 is a graph showing the relationship between the temperature and pressure of the saturation steam;

FIG. 9 (A) and (B) are configuration block diagrams for a second embodiment of the present invention;

FIG. 31 is a system diagram showing the relationship between the feed water heater and a thermal power generation plant; and FIG. 32 is a diagram showing the structure of a feed water heater in FIG. 31.

DETAILED DESCRIPTION OF THE PREFERRED EMBODIMENT OF THE INVENTION

Now, the present invention will be described in a greater detail hereunder with reference to the accompanying drawing.

Figure 1:
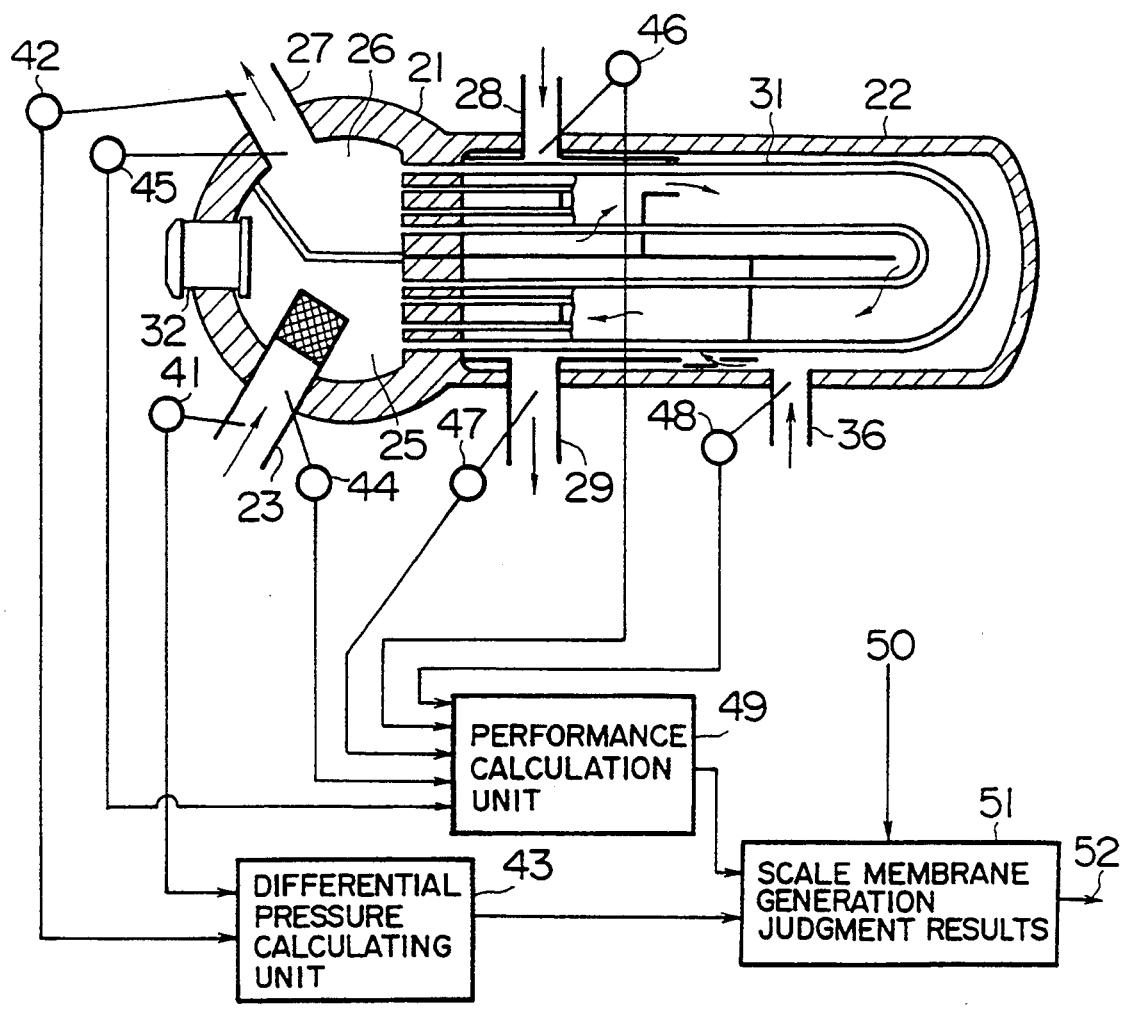
FIG. 1 is a block diagram of a first embodiment of a heat exchanger abnormality monitoring apparatus of the present invention.

First, in the embodiment of the first invention as shown in FIG. 1, feed water inlet pressure measuring portions 41 are respectively mounted at the feed water inlet portion 23 and the feed water outlet pressure measuring portions 42 are respectively mounted to the feed water outlet portion 27 in order to monitor the differential pressure between the feed water inlet and outlet of the feed water heater, and the output signals of the feed water inlet pressure measuring portion 41 and feed water outlet pressure measuring portions 42 are input to the differential pressure calculating portion 43.

Moreover, since there are disturbances in the flow of feed water in the vicinity of the inlet-side water chamber 25 and the outlet-side water chamber 26, the pressure of the feed water outlet pressure measuring portions 42 and the feed water inlet pressure measuring portion 41 becomes larger the closer outlet side water chamber and the inlet side water chamber become.

Therefore, the feed water inlet pressure measuring portion 41 and the feed water outlet pressure measuring portions 42 must be positioned sufficiently apart from the inlet-side water chamber 25 and the outlet-side water chamber 26, in order to measure small pulsations.

On the other hand, in order to monitor the heat exchange performance of the feed water heater, the feed water inlet process measurement portion 44 is mounted to the feed water inlet portion 23, the feed water outlet process measuring portion 45 is mounted to the feed water outlet portion 27, the extraction steam inlet process measurement portion 46 is mounted to the extracted steam inlet portion 28, the drain outlet process measurement portion 47 is mounted to the drain outlet portion 29 and the drain inlet process measurement portion 48 is mounted to the drain inlet portion 36. The output signals of these process measurement portions 44 through 48 are input to the performance calculation portion 49 and the output signals of the performance calculation portion 49 are input to the judgment portion 51. To the judgment portion 51 are input the output signals of the differential pressure calculating portion 43 and the load signals 50 of the power generation plant, and the judgment portion 51 outputs the scale membrane generation judgment results 52.

In this embodiment of the present invention, the pressure of the feed water at the feed water outlet portion 27 and the feed water inlet portion 23 that flows to the feed water heater or from the feed water heater is measured by the feed water outlet pressure measuring portions 42 and the feed water inlet pressure measuring portion 41 at a place where there is little pulsation, and the respective output signals are input to the differential pressure calculating portion 43 where the differential pressure value of the feed water at the feed water inlet portion and the feed water outlet portion is measured in a state where there is little vibration and those results are input to the judgment portion 51.

In general, the heat exchange performance of the heat exchanger (the feed water heater in this embodiment), is evaluated using the amount of heat that enters the feed water heater and the amount of heat that leaves the feed water heater.

Here, the amount of heat of the feed water that enters the feed water heater is the total of the amount of heat of the feed water that leaves the feed water heater, the amount of heat of the extracted steam from the extracted inlet portion and the amount of heat of the drain that enters from the drain inlet portion, and the associated quantities in order to calculate the total amount of heat of the feed water that enters are obtained using the feed water inlet process measurement portion 44, and the associated quantities in order to calculate the amount of heat of the drain that enters are obtained using the drain inlet process measurement portion 48. In addition, the amount of heat of the feed water that leaves the feed water heater, is the total of the amount of heat of the feed water that leaves the feed water outlet portion and the amount of heat of the drain that leaves the drain outlet portion, and the associated quantities, in order to calculate the amount of heat of the feed water that leaves, are obtained using the feed water outlet process measurement portion. The associated quantities, in order to calculate the amount of heat of the drain that leaves, are measured using the drain outlet process measurement portion 47.

The output signals of these process measurement portions 44 through 48 are input to the performance calculation portion 49, where calculations are performed in order to evaluate the heat exchange performance of the feed water heaters, and these results are input to the judgment portion 51.

In addition to the results of the heat exchange performance evaluation calculation and the results of feed water differential pressure calculation, the load signals of the power generation plant are also input to the judgment portion 51 where compensation according to the value for the load at that time is added to the results of heat exchange performance evaluation calculation and the results of feed water differential pressure calculation. Then, both values at the same time are used for the judgment logic shown in FIG. 2 to judge an excessive thickness of scale membrane at what portion of the feed water heater, and to output those results from the judgment portion 51.

Figure 2:
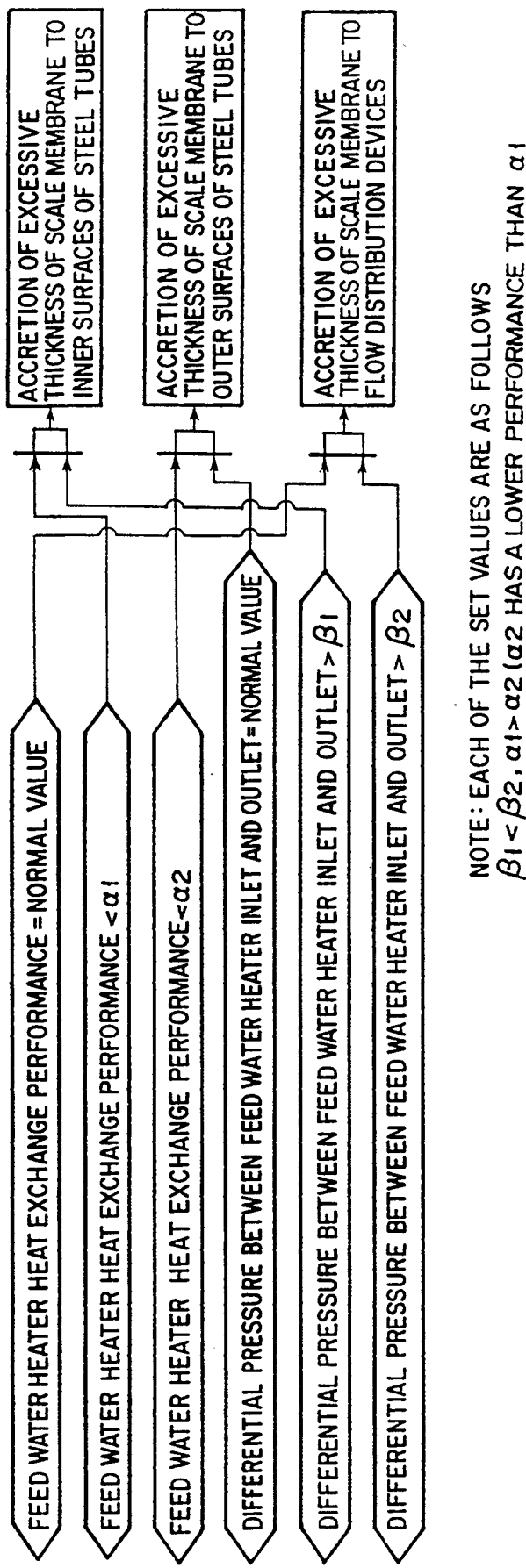
FIG. 2 is a judgment logic diagram for judging the presence of accretion of scale membrane and the portion of such, in a first embodiment of the present invention.

The following is a description of the configuration of the judgment logic, with reference to FIG. 2.

When there is an excessive thickness of scale membrane on the inner surface of a steel tube, there is the danger of destruction of the water chamber partition plate by a relatively small differential pressure. In cases such as these, the difference in the pressures between the outlet side water chamber and the inlet side water chamber increase simultaneously. So, the differential pressure between the feed water inlet and outlet also increase and the heat exchange performance drops.

In addition, when there is an excessive thickness of scale membrane accreted on the outer surface of the steel tubes, there is no danger of destruction of parts of the feed water heater since there is no increase in the differential pressure between the feed water inlet and outlet but there is a decrease in the heat exchange efficiency. In cases such as these, a judgement can be made first when there is a fairly reliable confirmation of the heat exchange performance. Also, when there is the generation of an excessive thickness of scale membrane on only the flow distribution devices, there is an increase in the differential pressure before and after the flow distribution devices. So, there is an increase in the feed water inlet and outlet differential pressure but there is no drop in the heat exchange efficiency.

Moreover, the mechanical strength of the flow distribution devices is relatively large when compared to that of the water chamber partition, and there is destruction until the differential pressure becomes as great. Accordingly, this can be reliably judged for the first time when the differential pressure is sufficiently great and when there is no destruction of the flow distribution devices.

The judgment logic operates in consideration of the conditions described above.

The following is a more specific description of the configuration and operation of a first embodiment of the invention described above, with reference to FIG. 3 through FIG. 8.

Figure 3:
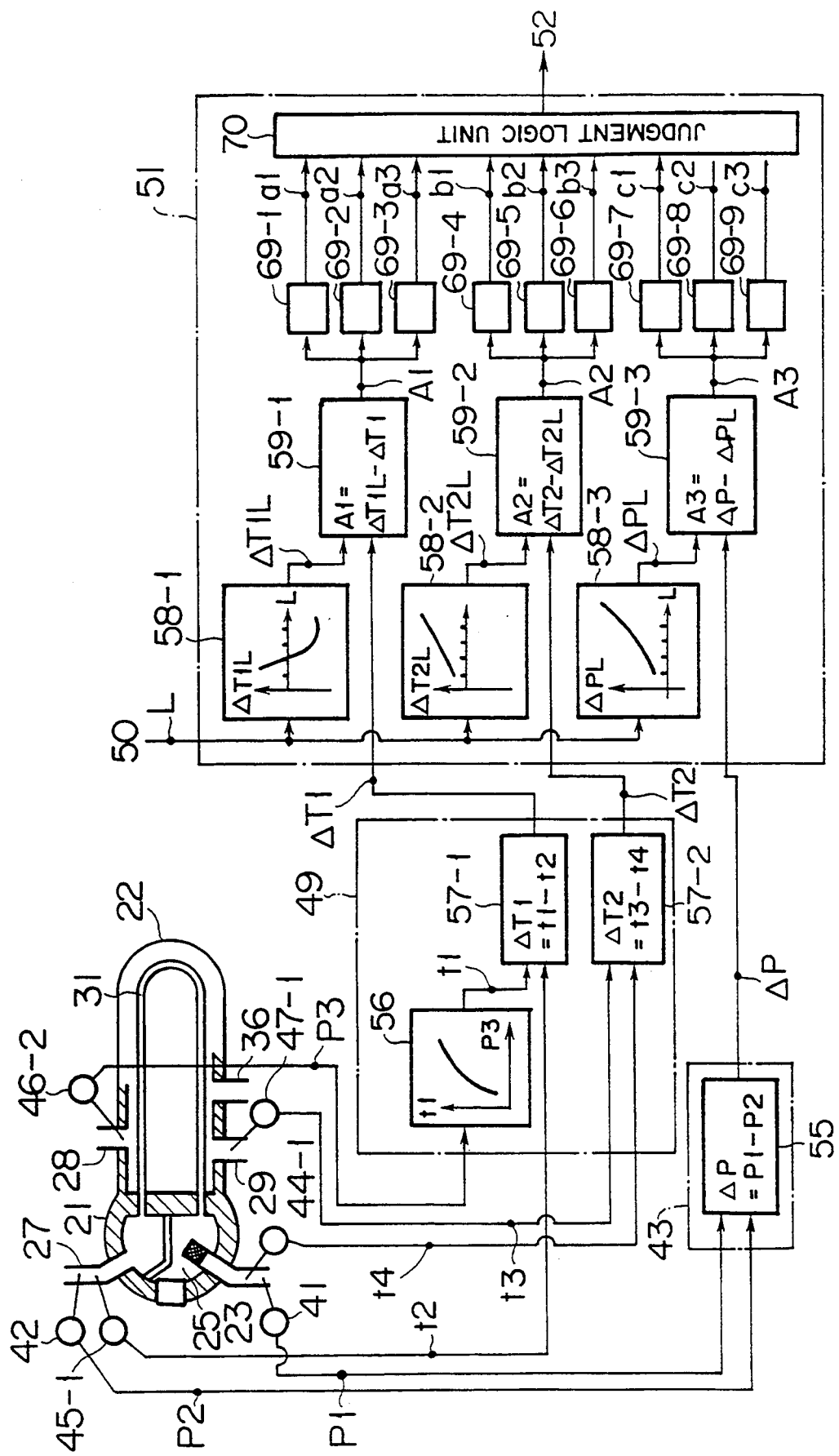
FIG. 3 is a block diagram showing a more detailed configuration for the first embodiment of the present invention.

FIG. 3 is a detailed figure of the configuration block shown in FIG. 1, and the output signals P1 of the feed water inlet pressure measuring portion 41 and the output signals P2 of the feed water outlet pressure measuring portions 42 are input to the differential pressure calculating portion 43 by the subtractor 55. Output signals $\Delta P$ are input to the subtractor 59-3 of the judgment portion 51. The feed water inlet temperature detector portion 44-1, that is, the feed water inlet process measurement portion 44, uses a drain outlet temperature detector portion 47-1 as the drain outlet process measurement portion 47. The output signals t4,t3 are input to the subtractor 57-2, and the output signals ΔT2 are calculated. This ΔT2 is input to the subtractor 59-2 of the judgment portion 51. The extracted steam inlet feed water heater internal pressure detector portion 46-2 is used as the extraction steam inlet process measurement portion 46, and output signals P3 are input to the saturation temperature (t1) calculation portion 56 of the performance calculation portion 49. Output signals t1 are input to the subtractor portion 57-1.

A feed water outlet temperature detector portion 45-1 is used as the feed water outlet process measuring portion 45. Output signals t2 are input to the subtractor portion 57-1. The output signals ΔT1 of this subtractor portion 57-1 are input to the subtractor 59-1 of the judgment portion 51. The load signals 50 (L) of the power generation plant are input to the ΔT1L reference calculation portion 58-1, the ΔT2 reference calculation portion 58-2 and the differential pressure reference calculation portion 58-3 of the judgment portion 51, and these output signals ΔT1L, ΔT2L and ΔPL are respectively input to the subtractors 59-1, 59-2 and 59-3.

In addition, the output signals A1 of the subtractor 59-1 are input to the alarm setting portions 69-1, 69-2 and 69-3. As a result, the ON-OFF output signals a1, a2 and a3 are input to the judgment logic portion 70. In addition, the output signals A3 of the subtractor portion 59-3 are input to the alarm setting portions 69-7, 69-8 and 69-9, and as a result, the ON-OFF output signals c1, c2 and c3 are input to the judgment logic portion 70.

Figures 4, 4A:
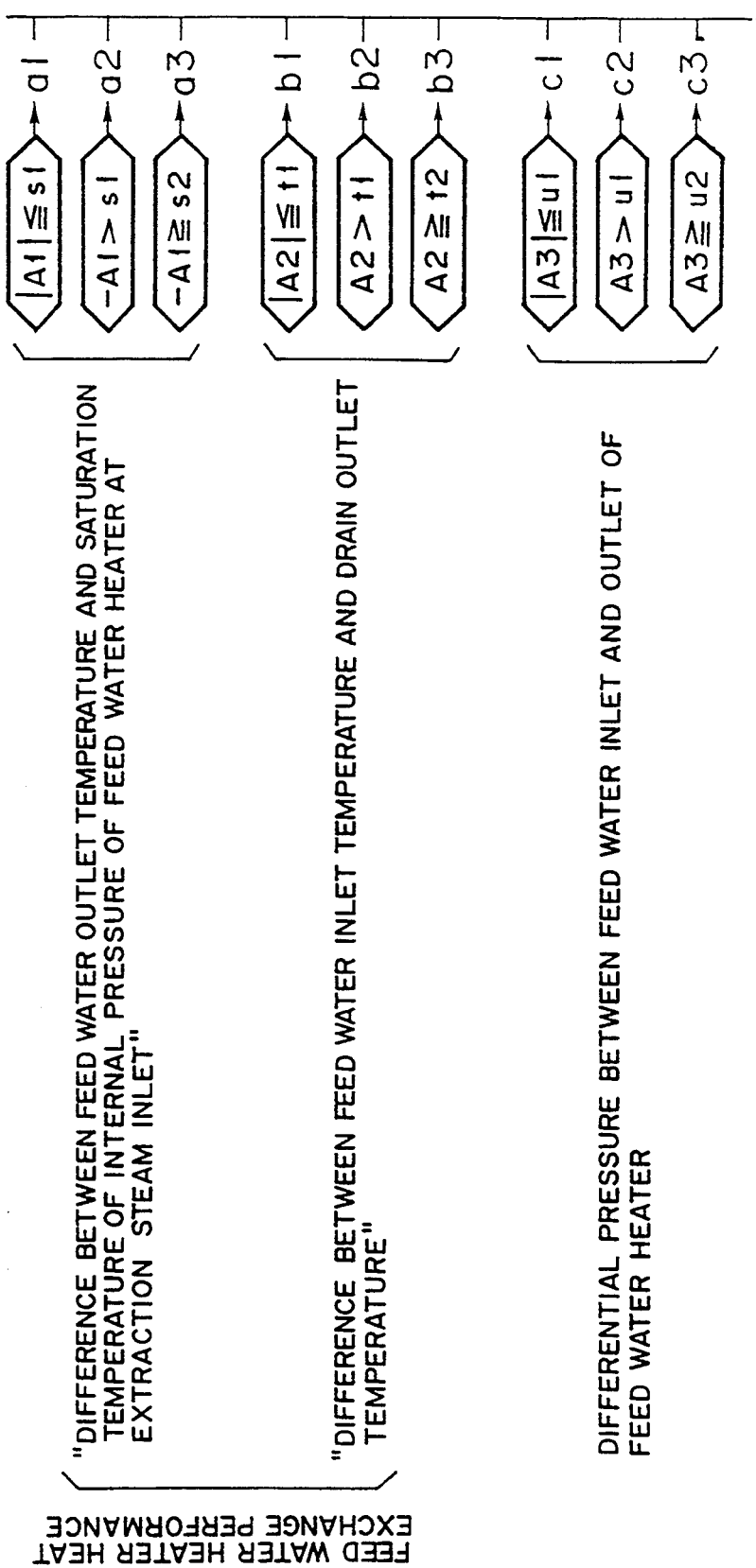
FIG. 4 is a judgment logic diagram for judging the presence of accretion of scale membrane and the portion of such, in a first embodiment of the present invention.
Figure 4B:
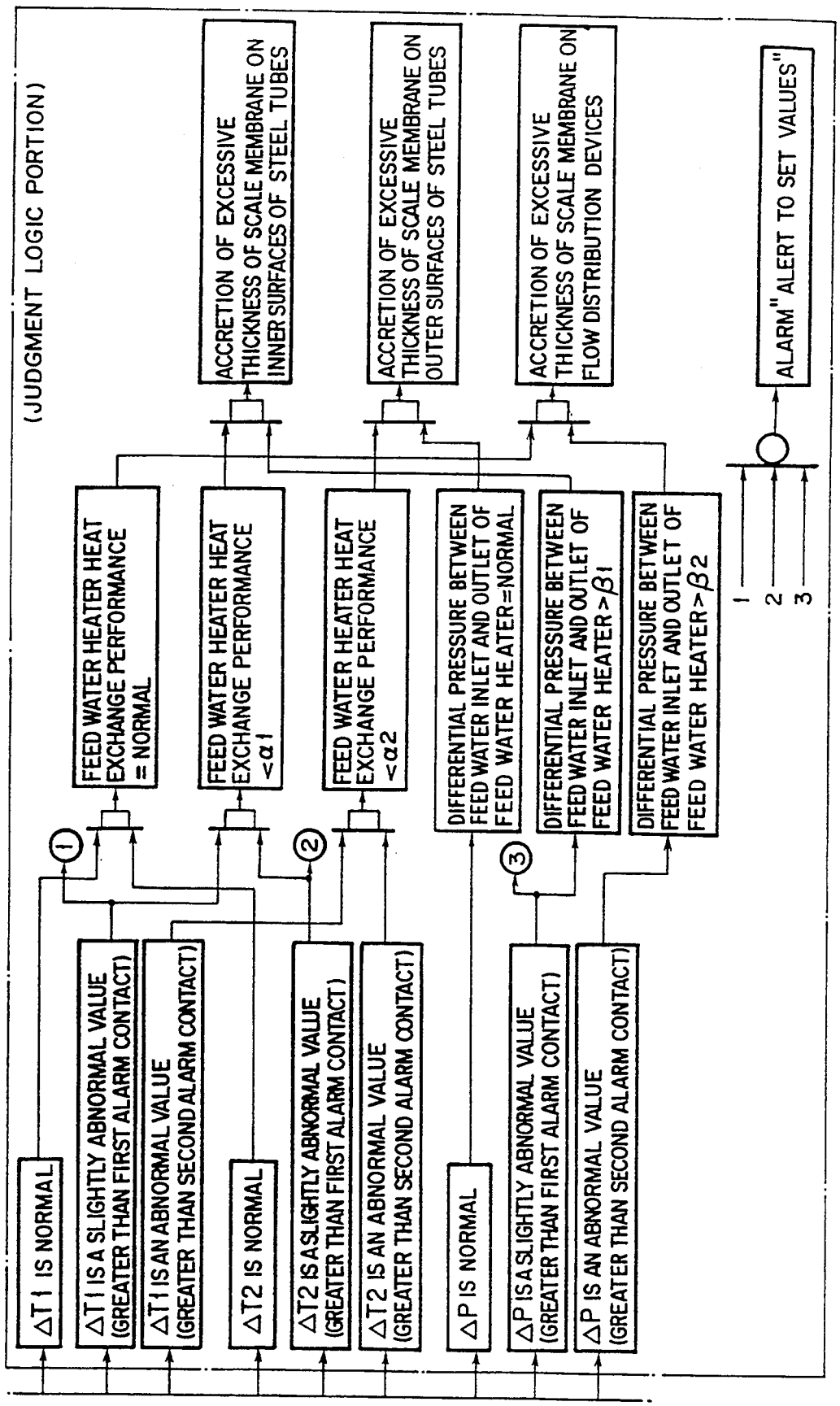

In the judgment logic portion 70, the judgment logic such as that shown in FIG. 4 judges for what part there is the generation of an excessive thickness of scale membrane and those scale membrane generation judgment results 52 are output as output signals of the judgment portion 51.

The following is a description of the operation of the embodiment described above.

The pressure in the feed water outlet portion and the feed water inlet portion for the feed water flowing in and out of the feed water heater is measured by the feed water inlet pressure measuring portion 41 and the feed water outlet pressure measuring portions 42 installed at places where there is little pulsation. The respective output signals P1 and P2 are input to the subtractor 55 configuring the differential pressure calculating portion 43, and the calculation ΔP=(P1-P2) is performed. The output signals ΔP that are the result are input to the subtractor 59-3. On the other hand, the load signals 50 (L) of the power generation plant at that time is input to the differential pressure reference calculation portion 58-3.

Magnetite scale membrane also accretes thinly (in a normal status) around all of the inner surfaces of the steel tubes and the flow distribution devices. Even if there is no increase or decrease in the amount of formation, the increase and decrease in the load of the power generation plant, that is, in the feed water flow flowing to the feed water heater, there is an increase and decrease in the differential pressure of the feed water inlet portion and the feed water outlet portion. As one example of this, FIG. 5 shows the case when there is a feed water heater on the side in the closest vicinity to the boiled of a power generation plant of the 600 MW class. Here, the relationship between the load L of the power generation plant and the differential pressure ΔPL of the pressure of the feed water inlet and outlet portion of the feed water heater, for the case when there is the formation in the normal status of a magnetite scale membrane for each feed water heater, is known beforehand. So, this relationship equation is stored in the differential pressure reference value calculation portion 58-3, and the input to this to the load signals 50 (L), as has been described, enables the value for the load, that is, the differential pressure reference value ΔPL for the feed water flow at that time, to be obtained. This differential pressure reference value ΔPL is also input to the subtractor 59-3 where $$A3 = (\Delta P - \Delta PL)$$

is calculated, that is, the difference between the differential pressure value (reference value) that is the normal value, and the measured value for the differential pressure between the feed water inlet portion and outlet portion for a certain load at a certain time is calculated, and the output signals A3 are input to the alarm setting portion 69-7, 69-8 and 69-9.

On the other hand, one method of monitoring the heat exchange performance of the feed water heater is monitoring both the "difference between the feed water inlet temperature and the saturation temperature of the feed water heater internal pressure at the extraction steam inlet" and the "difference between the drain outlet temperature and the feed water inlet temperature" and determining a heat exchange performance as dropping when this changes to a degree greater than a rated value. Moreover, in the case of this method, it is not necessary to have a drain inlet process measurement portion 48.

This method is used in this embodiment. More specifically, the "difference between the drain outlet temperature and the feed water inlet temperature" is determined by inputting the output signals t3 from the drain outlet temperature detector portion 47-1 and the output signals t4 from the feed water inlet temperature detector portion 44-1 to the subtractor portion 57-2 that configures the performance calculation portion 49 and which performs the calculation $$\Delta T2 = t3 - t4$$

These output signals ΔT2 are input to the subtractor portion n59-2 that configures the judgment portion 51.

In addition, the "difference between the feed water inlet temperature and the saturation temperature of the feed water heater internal pressure at the extraction steam inlet" has the output signals P3 of the extracted steam inlet feed water heater internal pressure detector portion 46-2 input to the saturation temperature (t1) calculation portion 56 that configures the performance calculation portion 49.

There are many cases where water is used as the process liquid in a power generation plant, but in some cases, the relationship between the saturation steam temperature and the saturated steam pressure is as shown in FIG. 6. This relationship equation is stored beforehand in the saturation temperature (t1) calculation portion 56 so that the input of the output signals P3 enables calculation of the saturation temperature t1 with respect to the output signals P3. These output signals t1 are input to the subtractor portion 57-1.

On the other hand, the output signals t2 from the feed water outlet temperature detector portion 45-1 are also input to the subtractor portion 57-1, where the calculation $$\Delta T = t1-t2$$

is performed and the output signals ΔT1 are input to the subtractor portion 59-2 that configures the judgment portion 51. Also, the load signals 50 for the power generation plant at this time are also input to the ΔT1L reference calculation portion 58-1 and the ΔT2L reference value calculation portion 58-2.

Figure 7:
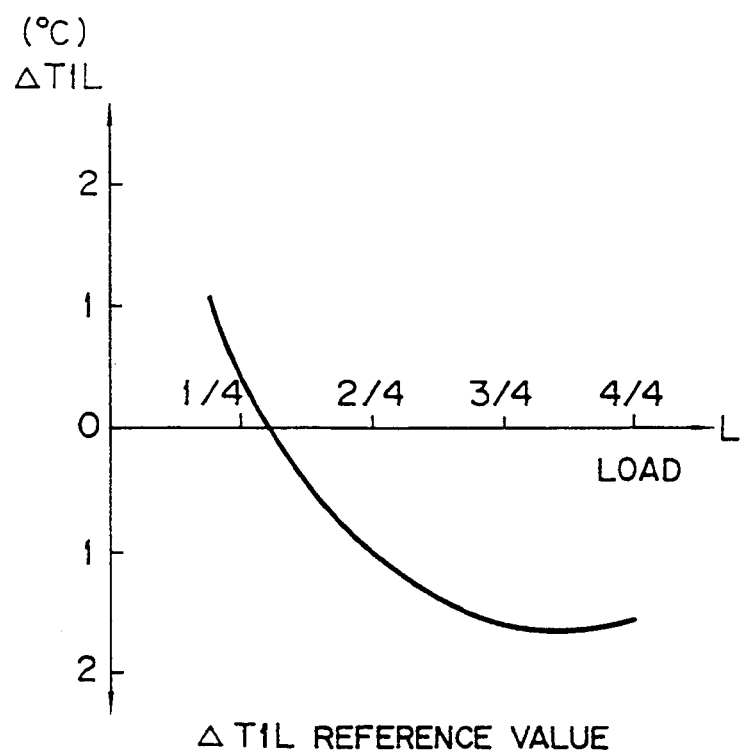
FIG. 7 is a graph showing the relationship between the load of a power generation plant in the state where there is a normal accretion of scale membrane, a "difference between the feed water outlet temperature and the saturation temperature of the internal pressure of the feed water heater at the extraction steam inlet" and a "difference between the feed water inlet temperature and the drain outlet temperature"
Figure 8:
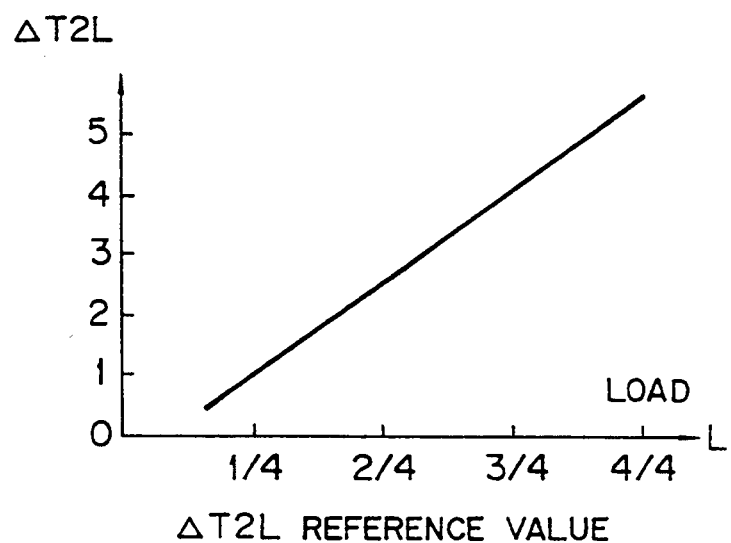
FIG. 8 is a graph showing the relationship between the load of a power generation plant in the status where there is a normal accretion of scale membrane, the "difference between the feed water outlet temperature and the saturation temperature of the internal pressure of the feed water heater at the extraction steam inlet" and the "difference between the feed water inlet temperature and the drain outlet temperature"

For the case where there is an accretion of a thin magnetite scale membrane for the entire surface of the inner surface of the steel tubes, the "difference between the feed water inlet temperature and the saturation temperature of the feed water heater internal pressure at the extraction steam inlet" (which is termed ΔT1L) and the "difference between the drain outlet temperature and the feed water inlet temperature" (which is termed ΔT2L) changes according to the increase and decrease in the feed water flow that flows to the feed water heater, that is, the increase and decrease of the load of the power generation plant. FIG. 7 and FIG. 8 shows this for the case of a feed water heater on the side in the vicinity closest to the boiler of a power generation plant of the 600 MW class.

In this manner, the relationship between the ΔT1L, ΔT2L of the feed water heater and the load of the power generation plant for the case when there is the formation of the magnetite scale membrane in a normal status is known beforehand and so this relationship equation is stored beforehand in the ΔT2L reference value calculation portion 58-2 and the ΔT1L reference calculation portion 58-1 and the input of the load signals 50 (L) enable the ΔT1L and ΔT2L for that load to be obtained.

This ΔT1L is input to the subtractor 59-1 and the ΔT2L is input to the subtractor portion 59-2 and in the respective subtractors, the calculations $$A1 = \Delta T1L - \Delta T1$$

$$A2 = \Delta T2 - \Delta T2L$$

are performed.

These values A1 and A2 are the differences between the (reference) values that should be when there is a normal situation, and the actually measured values for the "difference between the feed water inlet temperature and the saturation temperature of the feed water heater internal pressure at the extraction steam inlet" and the "difference between the drain outlet temperature and the feed water inlet temperature" at a certain time and a certain load status, and these output signals A1 and A2 are respectively input to the alarm setting portions 69-1, 69-2, 69-3, 69-4, 69-5 and 69-6.

The magnitude of each of the input signals A1, A2 and A3 are monitored by each of the alarm setting portions 69-9 through 69-12. As shown in the judgment logic of FIG. 4, if any of the input signals is above each of the set values, then one of the contact signals a1 through a3, b1 through b3, c1 through c3 is output to the judgment logic portion 70. In the judgment logic portion 70, the judgment logic of FIG. 4 is used so that a judgement is performed for not only the accretion of an excessive thickness of scale membrane to the feed water heater, but also for the positions of accretion of the scale membrane, and those results are output.

According to the present embodiment, as has been described above, it is possible to perform measurements of the output pressure of the feed water outlet portion and input portion for respective places where is little pulsation and so it is possible to monitor both differential pressures at a high reliability. However, the differential pressure influences the water chamber partition plate 30, which is easily destroyed even by a smaller differential pressure is generated by the formation of a scale membrane on the inner surface of the steel tubes but the formation of scale membrane to the inner surface of the steel tubes is determined by an AND condition for both "differential pressure of the feed water inlet and outlet of the feed water heater is a slightly abnormal value" and "heat exchange performance of feed water heater is a slightly abnormal value" and hence there is a high reliability.

In addition, the differential pressure that exerts an influence to the flow distribution devices 24 that are not destroyed by relatively large differential pressures, is the result of the formation of a scale membrane in the flow distribution devices but this generation is judged by "differential pressure between the feed water inlet and outlet of the feed water heater is an abnormal value" (that is, this detection uses a value u2 that is larger than the set value u1 for the differential pressure monitoring when it is judged that there is the accretion of a scale membrane to the inner surface of the steel tubes) and so the differential pressure monitoring has a high reliability.

On the other hand, when there is scale accretion to the steel tube outer surface, there is no generation of trouble such as the destruction of parts of the feed water heater by the differential pressure in particular but there is a drop in the heat exchange performance of the feed water heater and so it is better that scale removal be performed at as early a stage as possible. This scale accretion to the outer surfaces of the steel tubes in this manner is judged by whether "heat exchange performance of feed water heater is an abnormal value" that is, this detection uses the values s2, t2 that are larger than the set values s1, t1 for heat exchange performance monitoring when it is judged that there is the formation of a scale membrane to the inner surface of the steel tubes), and hence there is a high reliability of heat exchange performance.

In the manner described above, it is possible to effectively monitor at high reliability, whether or not there is the accretion of an excessive thickness of scale membrane to each of the portions of a feed water heater.

Still furthermore, with only differential pressure monitoring of the feed water inlet and outlet, it is not possible to determine whether the scale accretion is to the flow distribution devices or the inner surfaces of the steel tubes. In order to do this, monitoring both the differential pressure of the feed water outlet and the outlet side water chamber and the inlet side water chamber, and the differential pressure of the inlet side water chamber and the feed water inlet cannot provide a measurement for the pressure of the inlet side water chamber for which the pulsation is extremely large, therefore resulting in monitoring results of extremely low reliability. In addition, when there is monitoring of only the heat exchange performance of the feed water heater, it is not possible to determine whether the scale membrane accretion is on the steel tube inner surface or the outer surface, and it is not possible to monitor the accretion of scale membrane to only the flow distribution devices. However, if the present invention is used, then it is possible to determine whether the scale membrane accretion is to the inner surface or the outer surface of the steel tubes, without performing measurement of the pressure of the inlet side water chamber. Also, it is possible to perform the monitoring described above for any arbitrary load of the power generation plant and so there is a great effect.

The following is a description of a second embodiment of the present invention.

With the first embodiment, there is monitoring of the "difference between the feed water inlet temperature and the saturation temperature of the feed water heater internal pressure at the extraction steam inlet" and the "difference between the drain outlet temperature and the feed water inlet temperature". In this embodiment, there is monitoring on the basis of the ratio of heat conductivity of the steel tubes. FIG. 9 (A) and (B) show the block diagram for this case.

In this second embodiment, the feed water and the extraction steam that flows in the feed water heater have their temperatures measured in each of the portions desuperheating zone, condensing zone and drain cooling portion of the feed water heater shell. These results are used to calculate the ratio of heat conductivity of the steel tubes in each of the portions, with those results being used to monitor heat exchange performance.

Figure 10:
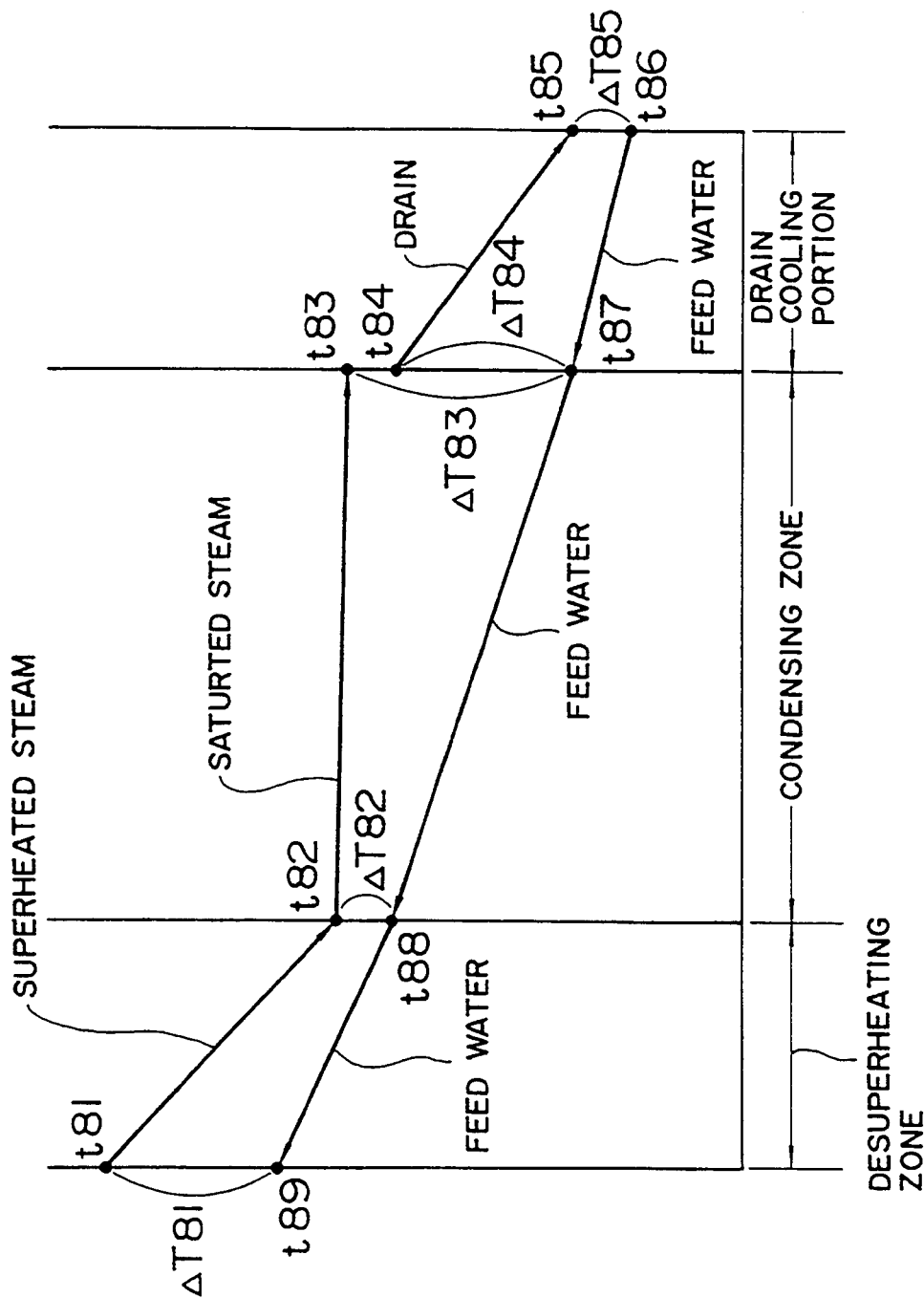
FIG. 10 is a graph showing the relationship between the temperature at each portion of the drain and the extraction steam, and the feed water of the feed water heater when there is the accretion of a thin scale membrane on the inner surfaces of the heat exchanger tubes.

FIG. 10 shows an outline of the relationship with the temperature in each of the portions of the feed water heater shell or for the drain and the extraction steam. The temperature t84 and t85 of the drain and the extraction steam in the feed water heater shell becomes higher for thicker accretion of scale to the outer surface or inner surface of the steel tubes. On the other hand, the temperature t87, t88 and t89 of the feed water inside the steel tubes becomes lower.

To describe the operation of each of the portions of FIG. 9, with reference to FIG. 10, the extracted steam inlet temperature t81 to the feed water heater is obtained by the temperature detector portion 81 which is the extracted steam inlet process measurement portion. The feed water temperature t89 is obtained by the temperature detector portion 89 which is the feed water outlet process measurement portion. The drain outlet temperature t85 from the feed water heater is obtained from the temperature detector portion 85, which is the drain outlet process measurement portion. Also, the feed water inlet temperature t86 to the feed water heater is obtained by the temperature detection portion 86 as the feed water inlet process measurement portion.

In addition, the feed water inlet flow Wf to the feed water heater is obtained by the flow detector portion 90, and the feed water pressure P is obtained by the detector portion 44-2 for the feed water inlet pressure 11.

Furthermore, the desuperheating zone outlet temperature t82 is obtained from the temperature detection portion 82, and the temperature detector portion 83 gives the saturated steam temperature t83 (equivalent to the saturation temperature of the internal pressure of the feed water heater at the extraction steam inlet) in the condensing zone. In addition, the drain cooling portion inlet drain temperature t4 is obtained by the temperature detection portion 84, the feed water temperature t87 inside the steel tubes in the drain cooling portion outlet is obtained from the temperature detection portion 87 and the feed water temperature t88 inside the steel tubes in the condensing zone is obtained by the temperature detection portion 88.

Each of the values t81 through t89 described earlier and obtained in this manner are input to the performance calculation portion 49. In this case, the temperature signals t81 and t89 are input to the calculation portion 95-1 that comprises the performance calculation portion and the calculation results $\Delta T81$ are output. To the subtractor portion 95-2 are input the temperature signals t82 and t88 and the subtraction results $\Delta T82$ are output. To the subtractor portion 95-3 are input the temperature signals t83 and t87, and the subtraction results $\Delta T83$ are output. To the subtractor portion 95-4 are input the temperature signals t84 and t87, and the subtraction results $\Delta T84$ are output. To the subtractor portion 95-4 are input the temperature signals t85 and t86, and the subtraction results $\Delta T85$ are output.

Of the outputs described above, $\Delta T81$ and $\Delta T82$ are input to the logarithmic mean temperature difference calculation portion 96-1 in the desuperheating zone, and the calculation results $\Delta Tm1$ are output. $\Delta T82$ and $\Delta T83$ are input to the logarithmic mean temperature difference calculation portion 96-2 in the condensing zone and those calculation results $\Delta Tm2$ are output. $\Delta T84$ and $\Delta T85$ are input to the logarithmic mean temperature difference calculation portion 96-3 and those calculation results $\Delta Tm3$ are output.

On the other hand, the feed water pressure P and the temperature signals t89 described above, are input to the enthalpy calculation portion 97-1 of the feed water outlet that configures the performance calculation portion 49 and the calculation results h89 are output. In the same manner, the feed water pressure P and the temperature signals t88 described above, are input to the enthalpy calculation portion 97-2 for the condensing zone outlet feed water portion and the calculation results h88 are output. The feed water pressure P and the temperature signals t87 are input to the enthalpy calculation portion 97-3 for the drain cooling zone outlet feed water and those calculation results h87 are output. In addition, the feed water pressure P and the temperature signals t86 are input to the enthalpy calculation portion of the feed water inlet and those calculation results h86 are output.

The previously described feed water inlet flow Wf and the calculation results h89, h88 and $\Delta Tm1$ are input to the coefficient of thermal conductivity calculation portion 98-1 in the desuperheating zone, and the calculation results K1 are output. In addition, the feed water inlet flow Wf and the calculation results h88, h87 and $\Delta Tm2$ are input to the coefficient of heat conductivity calculation portion 98-2 in the condensing zone, and the calculation results K2 are output. In addition, Wf, h87, h86 and $\Delta Tm3$ are input to the coefficient of heat conductivity calculation portion 98-3 in the drain cooling portion, and the calculation results K3 are output.

These calculation results K1, K2 and L3 are respectively input to the subtractor portions 100-1, 100-2 and 100-3 that configure the judgment portion 51.

On the other hand, the load signals 50 (L) for the power generation plant are input to the K1L reference value calculation portion 99-1, the K2L reference value calculation portion 99-2 and the K3L reference value calculation portion 99-3 of the judgment portion 51, and the output signals K1L, K2L and K3L are input to the subtractor portions 100-1, 100-2 and 100-3 described before. These calculation results B1, B2 and B3 are respectively input to the alarm setting portions 101-1 through 101-9, and as the result are obtained the ON-OFF output signals d1, d2, d3, e1, e2, e3, f1, f2 and f3.

Figure 11B:
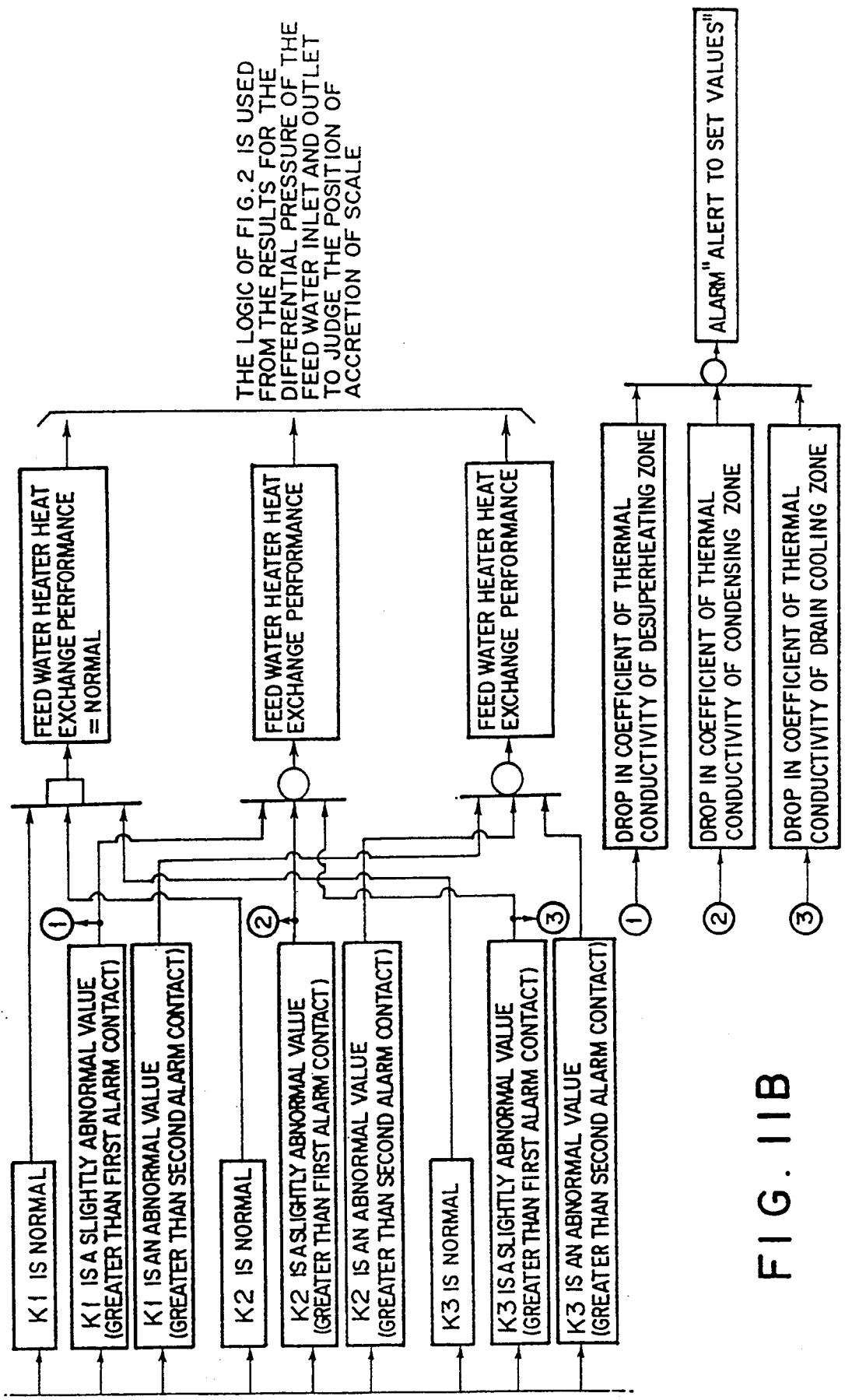
FIG. 11 is a judgment logic diagram used in the embodiment of FIG. 9.

These ON-OFF signals are input to the judgment logic portion 102 where the judgment logic of FIG. 11 makes a judgment for where there is an excessive thickness of scale membrane accretion, and those judgment results 52 are output as the output signals of the judgment portion 51.

The following is a description of this operation.

First, with respect to the heater, each of the temperature detector portions 81 through 89 measured the actual temperatures t81 through t89 corresponding to each of the points in FIG. 10. These measurement results are used to calculate $\Delta T81 = t81-t89$ by the subtractor 95-1,
$\Delta T82 = t82-t88$ by the subtractor 95-2,
$\Delta T83 = t83-t87$ by the subtractor 95-3,
$\Delta T84 = t84-t87$ by the subtractor 95-4, and
$\Delta T85 = t85-t86$ by the subtractor 95-5, respectively.

Following this, these results are used to calculate the logarithmic mean temperature in the desuperheating zone $$\Delta Tm1 = (\Delta T81 - \Delta T82) \approx \log(\Delta T81/\Delta T82)$$

by logarithmic mean temperature difference calculation portion 96-1, the logarithmic mean temperature in the condenser zone $$\Delta Tm2 = (\Delta T82 - LT83) \approx \log(\Delta T82/\Delta T83)$$

by logarithmic mean temperature difference calculation portion 96-2, and the logarithmic mean temperature in the drain cooling zone $$\Delta Tm3 = (\Delta T84 - \Delta T85) \approx \log(\Delta T84/\Delta T85)$$

by logarithmic mean temperature difference calculation portion 96-3, respectively.

Figure 12:
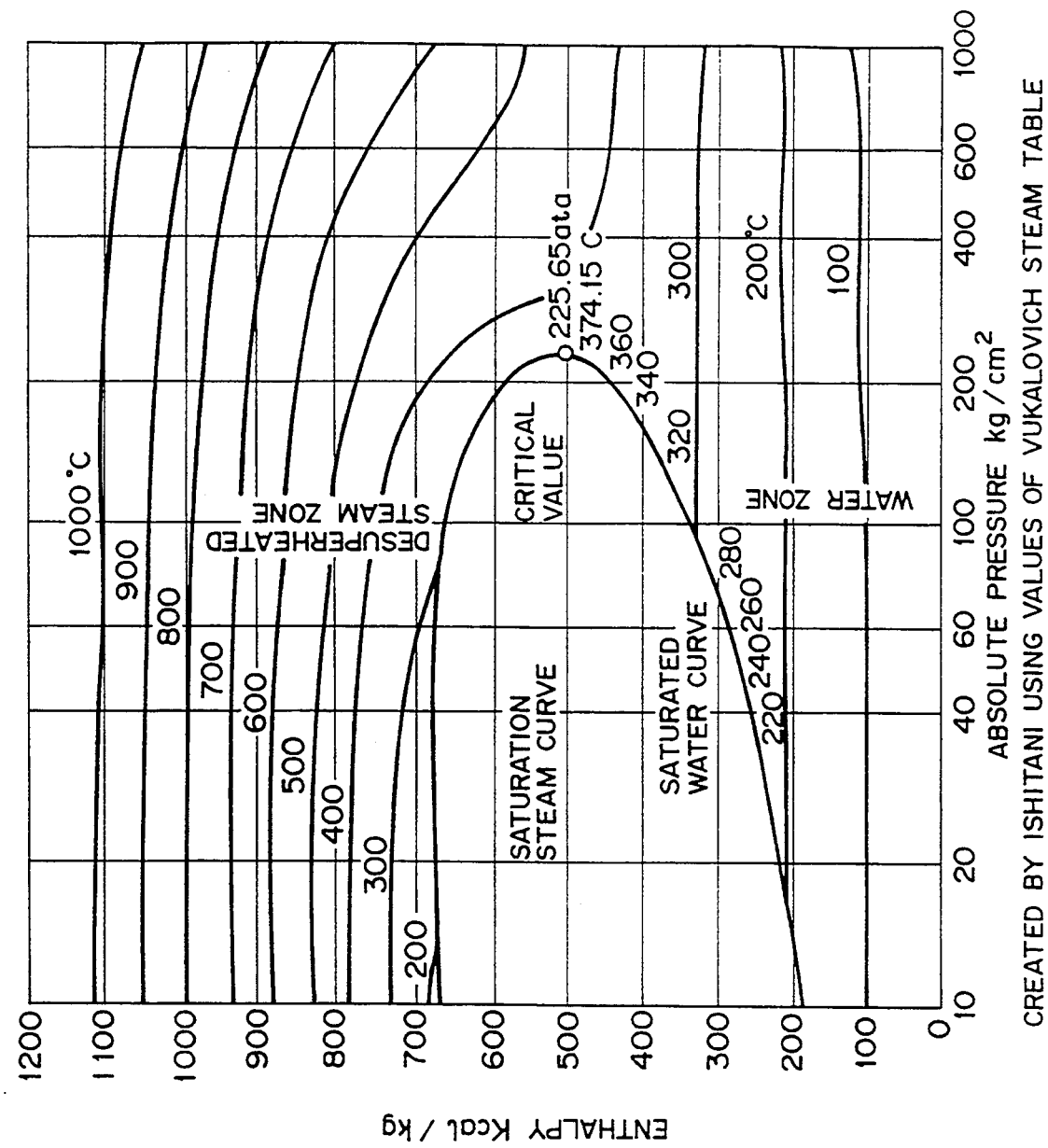
FIG. 12 is a graph showing the relationship between the pressure and temperature, and the enthalpy of the steam or the water, as used in the embodiment of FIG. 9.

On the other hand, each of the enthalpy calculation portions 97-1 through 97-4 calculates each of the entropies h89 through h86 for the feed water inlet and the drain cooling zone outlet feed water, the condenser outlet feed water and the feed water outlet. In this case, FIG. 12 shows the relationship between the water and the steam enthalpy, and their pressure and temperature. This relationship equation is stored in each of the enthalpy calculation portions 97-1 through 97-4 and the feed water pressure and t89 are input to the enthalpy calculation portion 97-1 and the enthalpy h88 at the feed water outlet is calculated. In the same manner, P and t87 are input to 97-2 and the enthalpy h88 at the condenser zone outlet feed water is calculated, and P and t87 are input to enthalpy calculation portion 97-3 and the enthalpy h87 at the drain cooling zone outlet feed water is calculated. In addition, P and t86 are input to 97-4 and the enthalpy h86 at the feed water inlet is calculated.

Here, the heat exchange amount Q (KCal/h) of the heat exchanger (the feed water heater in this example) are generally given by the following equation.

$$Q = Wf \times (h\ out - h\ in) \quad (1)$$

Here,
Wf: feed water inlet flow (Kg/h)
h out: outlet side feed water enthalpy (KCal/kg) and
h in: inlet side feed water enthalpy (KCal/kg).

On the other hand, in the feed water heater, the extracted steam or drain has the heat moving via the walls of the tubes of the heat exchanger towards the feed water but the amount of heat exchange Q(KCal/h) for each of these portions can be calculated by the following equation.

$$Q = A \times K \times \Delta Tm \quad (2)$$

Here,
$\Delta Tm$: logarithmic mean temperature difference (°C.) for each portion
K: coefficient of thermal conductivity at each portion (Kcal/m$^2$·h·°C.)
A: area of thermal transmission at each portion (m$^2$)

Accordingly, from equations (1) and (2), $$K = Wf \times (h_{out} - h_{in})/(A \times \Delta Tm) \quad (3)$$

Here, A is the area of thermal transmission at each portion, and does not change for the operating time of the power generation plant and can be thought of as being constant for each portion.

On the other hand, the coefficient of thermal conductivity K (Kcal/m$^2$·h·°C.) is determined by the following equation.

$$1/K = 1/h_o + (\delta/\lambda) \times A_o/A_m + (1/h_i) \times A_o/A_i + r_o + r_i \times A_o/A_i$$

Here,
ho: outer border coefficient of thermal conductivity of heat exchanger tubes (Kcal/m$^2$·h·°C.)
hi: inner border coefficient of thermal conductivity of heat exchanger tubes (Kcal/m$^2$·h·°C.)
λ: coefficient of thermal conductivity of heat exchanger tubes (Kcal/m$^2$·h·°C.)
δ: wall thickness of heat exchanger tubes (m)
$r_o$: resistance/temperature of outer surface of heat exchanger tubes (m$^2$·h·°C./Kcal)
$r_i$: resistance/temperature of inner surface of heat exchanger tubes (m$^2$·h·°C./Kcal)
$A_o$: outer surface area of heat exchanger tubes (m$^2$)
$A_i$: inner surface area of heat exchanger tubes (m$^2$)
$A_m$: mean of outer and inner surface area of heat exchanger tubes (m$^2$)

More specifically, ro and ri, that is, the resistance/temperature increases for the thickness of the scale membrane that accretes on the outer surface and the inner surface of the tubes of the heat exchanger and, as a result, the coefficient of thermal conductivity K decreases. The heat exchange performance at a portion of the heat exchanger drops to the lower coefficient of thermal conductivity K.

Accordingly, if the value for the coefficient of thermal conductivity of each portion of the feed water heater is monitored, then it is possible not only to judge the heat exchange performance, but also the thickness of the scale membrane that accretes to the outer surface or the inner surface of the tubes of the heat exchanger.

Here, the coefficient of thermal conductivity at each portion of the feed water heat exchanger is determined in accordance with equation (3), and so as has been described earlier, the feed water inlet flow Wf, h89, h88, and $\Delta Tm1$ are input to the coefficient of thermal conductivity calculation portion 98-1, and the calculation for $$K1 = \{Wf \times (h89 - h88)\}/(A1 \times \Delta Tm1) \text{ is performed}$$

Here,

A1: area of thermal transmission of desuperheating zone (constant), and the coefficient of thermal conductivity K1 in the desuperheating portion is obtained. In addition, Wf, h88, h87 and ΔTm2 are input, as has been described above, to the coefficient of thermal conductivity calculation portion 98-2 and if the calculation $$K2 = \{Wf \times (h88 - h87)\} / (A2 \times \Delta Tm2)$$

Here,

A2: area of thermal transmission of condensing zone (constant)

is performed, then it is possible to obtain the coefficient of thermal conductivity K2 for the condenser portion. In the same manner, the input of Wf and h87, h86 and ΔTm3 to the coefficient of thermal conductivity calculation portion 98-3 and if the calculation $$K3 = \{Wf \times (h87 - h86)\} / (A3 \times \Delta Tm3)$$

Here,

A3: area of thermal transmission of drain cooling zone (constant)

is performed, then it is possible to obtain the coefficient of thermal conductivity K3 for the drain cooling zone.

However, even in cases where there is the thin accretion of a magnetite scale membrane over the entire inner surface of the steel tubes, then even in cases where there is no increase or decrease in the amount of scale, then, increases and decreases in the load of the power generation plant, that is, increases and decreases in the feed water flow into the feed water heater, cause an increase in the respective coefficients of thermal conductivity K1, K2 and K3 of the desuperheating zone, the condensing zone and the drain cooling zone. In the normal status, the values for K1, K2 and K3 can be measured with respect to each of the loads when there is a change in the load of the power generation plant, and respectively stored in the K1L reference value calculation portion 99-1, the K2L reference value calculation portion 99-2 and the K3L reference value calculation portion 99-3 that configure the judgment portion 51. Here, the input of the load signals 50 (L) for the power generation plant to the K1L reference value calculation portion 99-1, the K2L reference value calculation portion 99-2 and the K3L reference value calculation portion 99-3 outputs the reference values K1L, K2L and K3L for the K1, K2 and K3 with respect to that load.

In the subtractor portions 100-1, 100-2 and 100-3, the K1, K2 and K3 that are the calculation results of K1L, L2L and K3L described above, and 98-1, 98-2 and 98-3, and the calculations for $$B1 = (K1L - K1)$$

$$B2 = (K2L - K2)$$

$$B3 = (K3L - K3)$$

are performed in each of the calculation portions. B1, B2 and B3 are the differences between the reference values (K1L, K2L, K3L) for the respective coefficients of thermal conductivity and the measured values (K1, K2, K3) for the respective coefficients of thermal conductivity at the desuperheating zone, the condensing zone and the drain cooling zone for the case when there is an even and thin accretion of scale membrane to the entire inner surface of the steel tubes and for an arbitrary load.

Of these calculation results, B1 are input to the alarm setting portions 101-1, 101-2 and 101-3, B2 are input to 101-4, 101-5 and 101-6 and B3 are input to 101-7, 101-8 and 101-9. By this, the ON-OFF output signals d1, d2, d3, e1, e2, e3, f1, f2 and f3 are obtained from the respective alarm setting portions, and these are used to judge the drop of heat exchange performance of the feed water heater. This and both the monitoring results for the differential pressure of the feed water inlet and outlet of the feed water heater obtained by a separately described method are used so that the judgment logic shown in FIG. 2 can give judgement results in the same manner as done in FIG. 3 and FIG. 4.

Accordingly, the same effect as the embodiments shown in FIG. 3 and FIG. 4 are obtained. In addition, with this embodiment, the coefficient of thermal conductivity is monitored and obtained for the steel tube desuperheating zone, the condensing zone and the drain cooling zone and so those portions where there is an excessive generation of scale membrane can be judged for up to the steel tube desuperheating zone, the condensing zone and the drain cooling zone. In addition, the increase in the thickness of accretion of scale membrane causes the ro and the ri of the previously described equation (4) to increase and accordingly, is a relationship equation where the coefficient of thermal conductivity K decreases so that monitoring the amount of increase in the coefficient of thermal conductivity enables an approximately value for the thickness (amount) of the scale membrane to be known.

Moreover, the saturation steam temperature t83 in the condenser portion is measured using the temperature detector portion 83. Instead of this, however, a pressure detector can be used to measure the saturation steam pressure in the condenser portion, and these results can be used to determine the saturation steam temperature t83.

In addition, in this embodiment, the feed water flow on the side of the feed water inlet was measured but this can also be measured on the side of the feed water outlet. In addition, calculating the enthalpy for each of the points of the feed water involves measuring the feed water inlet pressure by the feed water inlet pressure detector portion 44-2, but the feed water outlet pressure can be measured to determine the enthalpy. Also, the enthalpy of water and the relationship between the pressure and the temperature is as shown in FIG. 12 with the enthalpy of water having practically no relationship to the pressure, and having roughly the same value for that temperature, thus making it unnecessary to measure the pressure. Moreover, in order to calculate the enthalpy more accurately, the feed water inlet pressure and the feed water outlet pressure can be measured, and both of these values used to compensate the pressure for each portion of feed water and then using the pressures after compensation to calculate the enthalpy.

The following is a description of a third embodiment of the present invention.

In the second embodiment described above, as shown in FIG. 9, in order to calculate the coefficient of thermal conductivity of the steel tubes in each of the portions of the feed water heater, the feed water flowing in the feed water heater and the extraction steam and the drain have to have their temperature measured at each portion of the feed water heater shell. But there are also cases where it is difficult to measure the feed water temperature inside the tubes of the heat exchanger because of the structure of some feed water heaters. In cases such as these, the embodiment shown in FIG. 13 (A) and (B) can be used when the amount of heat (loss) radiated to the outside from the feed water heater shell is small enough that it can either be ignored when compared with the amount of heat exchange between the extraction steam and the drain, and the feed water, or otherwise is approximately constant.

Figure 14:
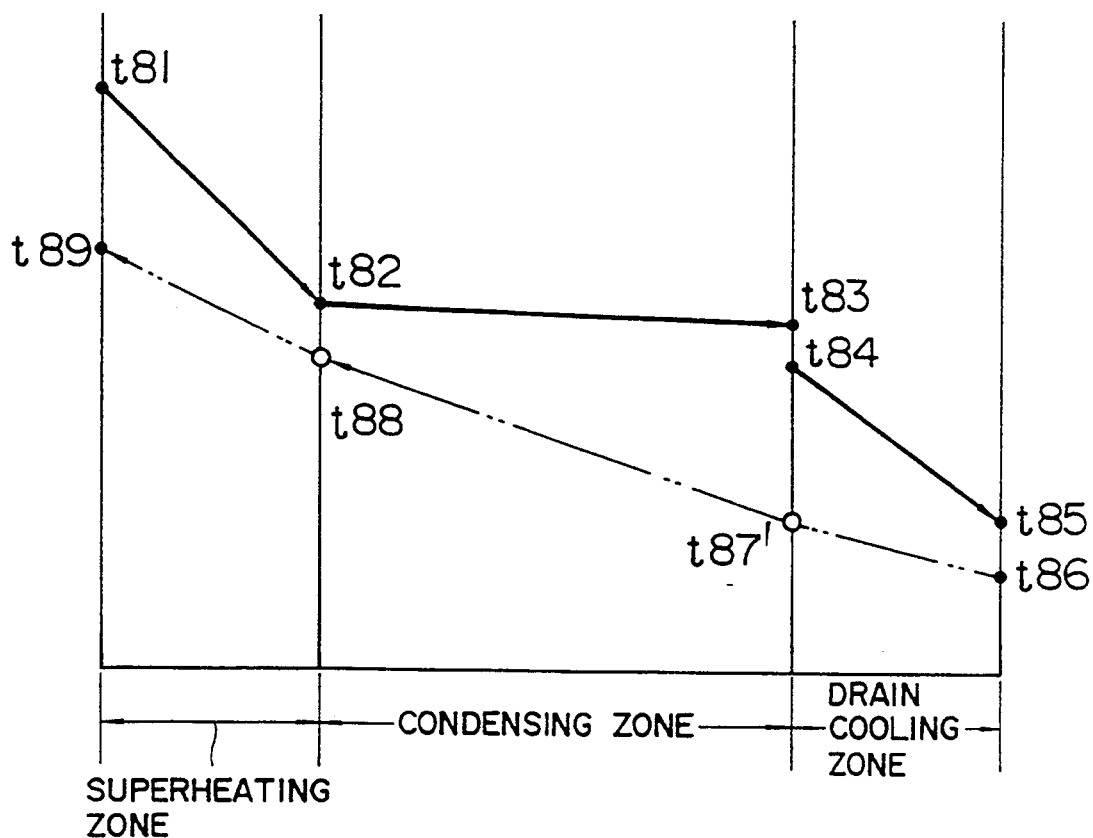
FIG. 14 is a graph showing the curve for the temperature of each portion of the drain and the extraction steam and the water inside a feed water heater for the case when there is the accretion of a thin scale membrane inside the heat exchanger tubes for the embodiment of FIG. 13.

Moreover, in these cases, the temperature curve for each portion of the feed water and the drain and the extraction steam of the feed water heater is the same as that for FIG. 10, that is, there is no direct measurement of the t88′ and t87′ in FIG. 14 using temperature detection portions. Instead, these are determined by calculation from other process measurement values from around the feed water heater, so that FIG. 14, that is, FIG. 10 is completed and the results used to judge the presence of accretion of a scale membrane using the apparatus of the second embodiment, that is, the apparatus of FIG. 9 through FIG. 11.

The following is a description of the configuration and the operation of this embodiment. Moreover, in FIGS. 13 (A) and (B), those portions of the configuration that correspond to similar portions of FIG. 9 through FIG. 11 are indicated with corresponding numerals and the corresponding descriptions of them have been omitted.

First, the process measurement points are all portions other than the temperature detection portions 88 and 87 shown in FIG. 9, and furthermore, the pressure detection portion 111 and the flow detection portion 110 are added as extraction steam inlet process measurement portions 46 so that the extraction steam pressure P111 and the extraction steam inlet flow WS are obtained. In addition, the drain inlet process measurement portion 48 uses the additional flow detection portion 114 to give the drain outlet flow Wd. This pressure detection portion 112 at the same place as the temperature detection portion 82 are added to give the desuperheating zone steam outlet pressure P112. Furthermore, the pressure detection portion 113 is added at the same place as the temperature detection portion 84, to give the drain cooling zone inlet drain pressure P113.

In general, the portion of the heat (loss) to the outside from the feed water heater shell is small to the extent that it can be ignored when compared to the amount of heat exchange between the extraction steam, the drain and the feed water. So, the "heat amount discharged by the extraction steam and the drain" and the "heat amount obtained by the feed water" are equal for each of the parts of the feed water heater shell.

The following equation is therefore established for the desuperheating portion.

$$Ws(h81\text{-}h82) = Wf(h89\text{-}h88') \tag{5}$$

Here,
Wf: feed water inlet flow (Kg/h)
Ws: extraction steam inlet flow (Kg/h)
h81: extraction steam enthalpy of extraction steam inlet (Kcal/kg)
h82: steam enthalpy of desuperheating zone steam outlet (Kcal/kg)
h89: enthalpy of feed water outlet (Kcal/kg)
h88′: enthalpy of condenser zone outlet feed water (Kcal/kg)

From equation (5)

$$h88' = h89 - (Ws/Wf) \times (h81\text{-}h82) \tag{5'}$$

and so the condenser zone outlet feed water temperature t88′ is determined using FIG. 12.

In addition, the following equation is established for the drain cooling portion.

$$Wd(h84\text{-}h85) = Wf(h87'\text{-}h86) \tag{6}$$

Here,
h84: drain outlet flow (Kg/h)
h85: drain outlet drain enthalpy (Kcal/kg)
h87′: drain cooling zone outlet feed water enthalpy (Kcal/kg)
h86: feed water inlet enthalpy (Kcal/kg)

From equation (6), $$h87' = h86 + (Wd/Wf) \times (h84\text{-}h85) \tag{6'}$$

and so the drain cooling zone outlet feed water temperature t87′ is determined using FIG. 12.

Here, the previously described calculation results are input to each of the enthalpy calculation portions 121-1 through 121-6 that configure the t87′ and t88′ temperature calculation portions 120. The relationship equation of FIG. 12 is stored in each of the enthalpy calculation portions, and each the enthalpies h81, h82, h84, h85, h86 and h89 are calculated with respect to each of the pressures and temperatures of the liquid or steam, and the results output.

To the h88′ calculation portion 122-1 are input to h81, h82 and h89 and also the Ws and Wf described above, and the calculation of equation (5′) is performed. In addition, to the h87′ calculation portion 122-2 are input to h84, h85 and h86, and also the Wd and Wf described above, and the calculation of equation (6′) is performed to calculate h87′ and the result is output to the t87′ temperature calculation portion 123-2. The t88′ and t87′ temperature calculation portions store the relationship equation of FIG. 12 and to them are input h88′ and h87′ and also P so that the condensing zone outlet feed water temperature t88′ and the drain cooling portion outlet feed water temperature t87′ are determined as the result of calculation.

In this manner, if the calculated t88′ and t87′ and the previously described measurement results are input to the performance calculation portion 49 of FIG. 9, then results the same as those of the second embodiment can be obtained.

Moreover, instead of direct measurement of the saturation steam pressure in the condensing zone, the temperature detector portion 83 can measure the steam pressure in the condensing zone, and the saturation steam pressure can be calculated from that value. In addition, in this embodiment, the drain outlet flow Wd and the extraction steam inlet flow Ws were measured by these two process values need not be measured as, for example, the relationship drain outlet flow (wd)=extraction steam inlet flow (Ws)+drain flow from drain inlet can be used and measurements made for two of these process variables and the drain outlet flow calculated from these.

In addition, flow detector portions were used to measure these flows, but the drain level of the feed water heater at the drain outlet portion is maintained at a constant level by a drain level adjustment valve, and there is a drain level adjustment valve 116 at the drain inlet portion in order to hold the drain level of the feed water heater on the side of one boiler, at a constant level. While the power generation plant is operating stably at a constant load, the respective drain level adjustment valve 116, 117 are opened to a constant degree and so the drain flow flowing through the respective drain adjustment valves can be known. Here, the inflowing drain and the outflowing drain of the feed water heater can be determined from the degree of opening of the drain level adjustment valve, and then used.

Figure 13A:
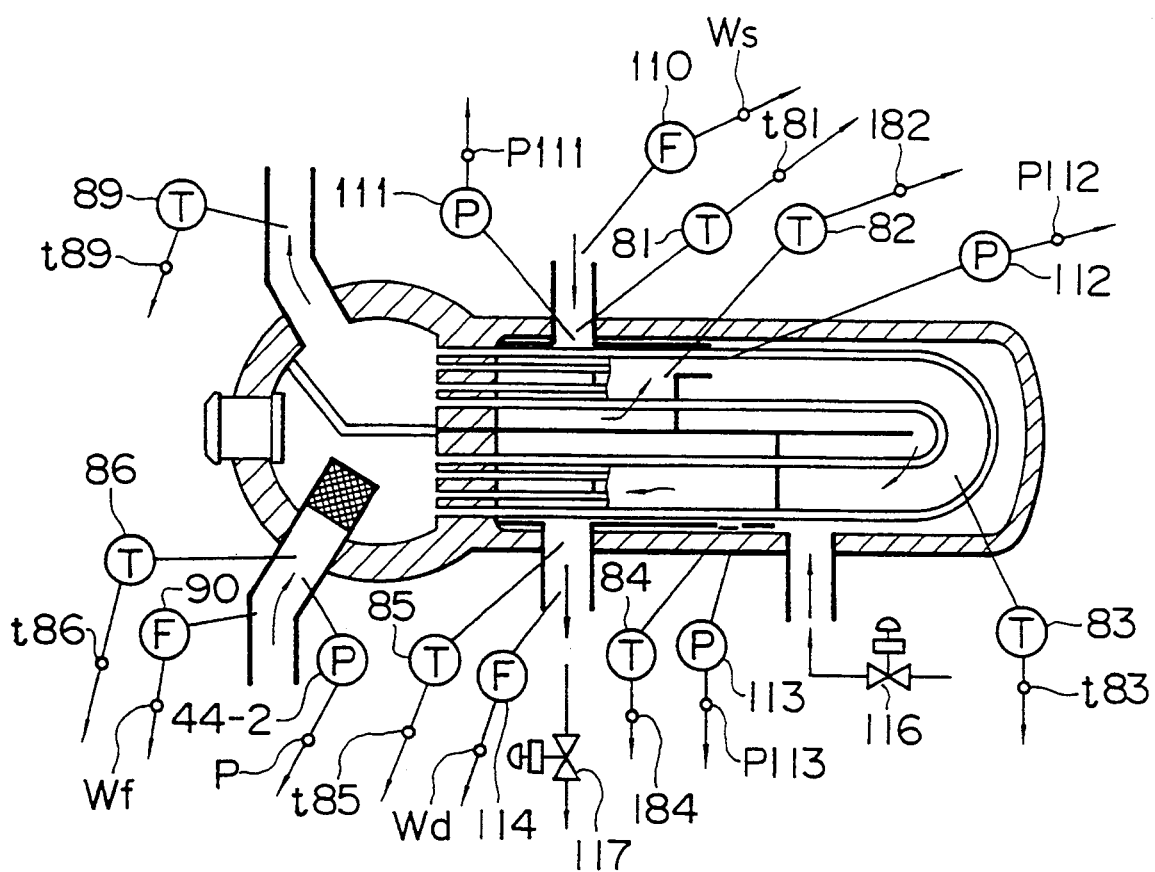
FIG. 13 (A) and (B) are configuration block diagrams for a third embodiment of the present invention.
Figure 13B:
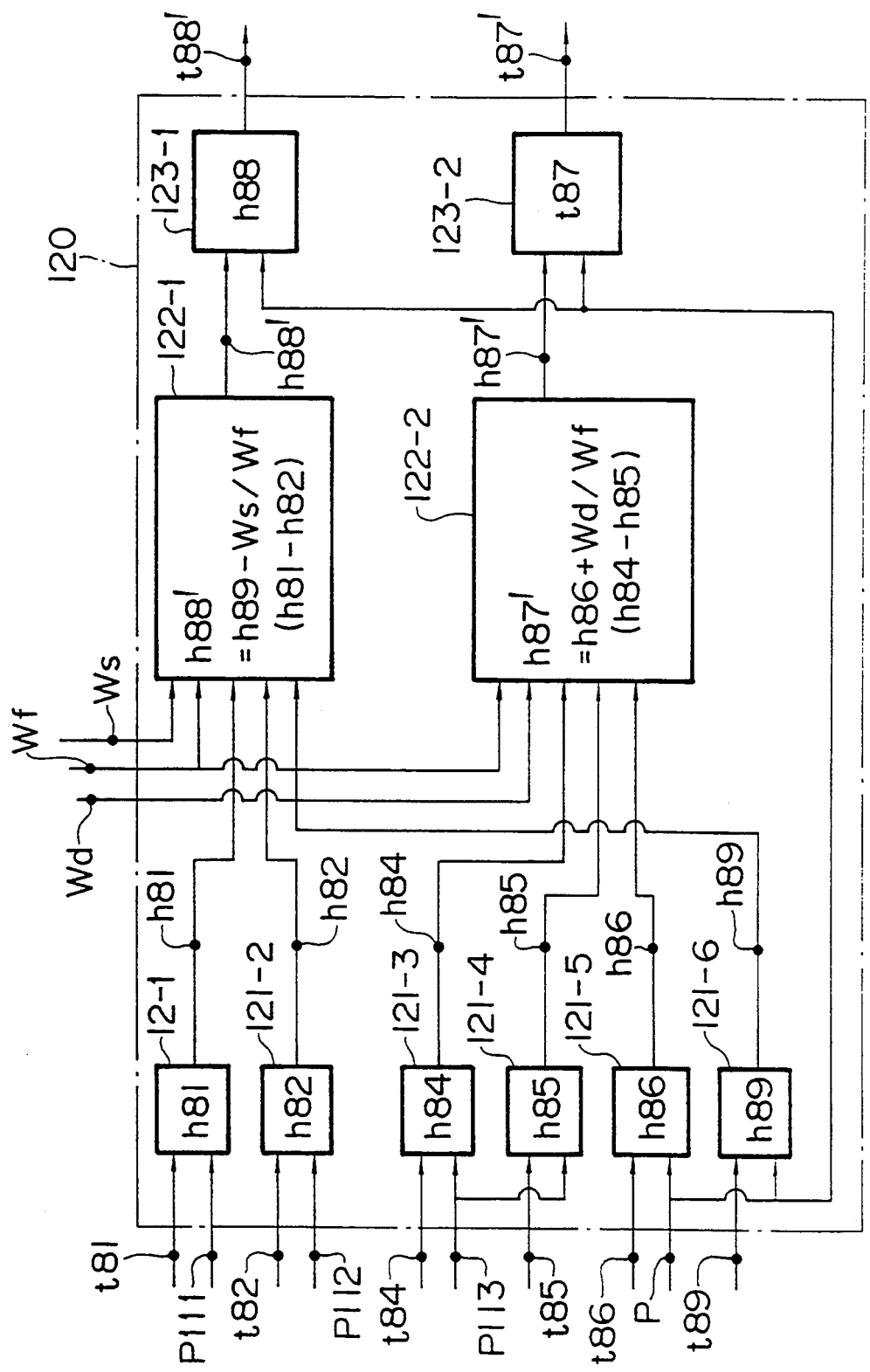

Moreover, in the cases shown in FIGS. 13 (A) and (B), the t87', t88' temperature calculation results from the t87', t88' temperature calculation portions 120 were input to the performance calculation portion 49 shown in FIG. 9 but the enthalpies h89, h86, h88, h87 at each of the points of the feed water used in FIG. 9 can use the results of the enthalpy calculation portion 121-6,121-5 and the h88' calculation portion 122-1 and the h87' calculation portion 122-2, of FIG. 13. Furthermore, the feed water heater has a large number of tubes for heat exchange. With the method described for the second embodiment, the temperature detectors 87,88 for the measurement of the feed water temperature of the feed water flowing in the steel tubes were mounted to the steel tubes so that the mean temperature could be measured. But, according to the method of this embodiment, the temperature and pressure of the extraction steam or the drain as the result of performing heat exchange with the feed water that flows in all the steel tubes is measured and this is used to calculate the feed water temperatures t87', t88' of the feed water that flows in the steel tubes and so this value is the mean temperature of the feed water that is distributed in all of the steel tubes and so it is possible to obtain the mean temperature without performing tests such as in the previous embodiment. In addition, it is not necessary to perform the difficult measurement for the feed water temperature inside the steel tubes.

In addition, according to the second embodiment, when there is no generation of a scale membrane in only the steel tubes to which the temperature detectors 87, 88 are mounted, the feed water that flows through them has normal heat exchange performed with the extraction steam or the drain and so t87,t88 have no change from the temperature at normal operation and it cannot be determined whether the portions for which there is the accretion of a scale membrane are the superheating zone or the drain cooling zone but according to the present embodiment, t87' and t88' are mean temperatures and so there is no generation of trouble such as this, and thus the effect is further improved.

Moreover, even in cases where there is trouble such as that in the second embodiment, if there is the accretion of a scale membrane on other steel tubes, the heat exchange performance will drop overall and so the feed water outlet temperature t89 drops from a normal value. On the other hand, the temperature of the extraction steam and the drain, for example, t83, t84, t85 and the like, rise to above normal values. So there is a drop in the heat exchange performance at all locations. Accordingly, there is the effect of being able to detect the accretion of a scale membrane.

In addition, with the second embodiment, tests sp that the temperature detectors for the measurement of the feed water temperature that flows inside the steel tubes can be mounted to the steel tubes in a place where it is possible to measure a temperature close to the mean, are not necessary for the reason described above.

More specifically, in the case of the present embodiment and also in the case of the first and second embodiments described above, the values calculated from actual measurements, and the $\Delta T1L$ and $\Delta T2L$ reference values, the differential pressure reference valves, K1L, K2L and K3L and the like are compared so that there is monitoring for the presence of relative change and so even in the case where any of the embodiments are used, in the status where there is the accretion of a thin membrane of magnetite scale for across the entire surface of the inner surfaces of the flow distribution devices and the steel tubes. If the process measurement values that must be measured for each load of the power generation plant are then measured, and $\Delta T1$, $\Delta T2$, the differential pressure, and K1, K2 and K3 are calculated, and stored in each of the reference value calculation portions for the $\Delta T1L$, $\Delta T2$, the differential pressure and K1L, K2L and K3L as the reference values, then there is no generation of the problems described above. For example, when the temperature detectors 87,88 are mounted to the steel tubes having a relatively high or low temperature when compared to other steel tubes, then in this case, only the t87, t88 of FIG. 10 become either higher or lower values but t81, t85, t86, t89 and the like are normal values and so the coefficient of thermal conductivity K1 of the superheating zone when the temperature is higher, is calculated as being lower than it is, and the coefficient of thermal conductivity for the other portions is calculated as being higher than its actual value. Conversely, when the temperature is lower, it is calculated as higher than it actually is, and the coefficient of thermal conductivity for the other portions is calculated as being lower that it actually is, by that amount. These values are stored in the reference value calculation portion as reference values so that there is no problem with monitoring of the presence of relative changes. In addition, for example, depending on the feed water heater, there are instances when holes occur in the steel tubes during operation and when there are leaks of feed water to the side of the feed water heater shell. In cases such as these, it is necessary to stop the operation of the power generation plant and to plug the inlet and outlet of the steel tubes having the holes so that the feed water does not flow. However, when this is done, the differential pressure between the feed water inlet and outlet holes increases by that portion even if there is only the normal accretion of a scale membrane, and the heat exchange performance drops by that portion.

However, if the rate value in the status where the holes are plugged is newly stored, it is possible to have the great effect of accurate monitoring even when there is this plugging.

On the other hand, in cases where the feed water flow to the feed water heater is a constant value irrespective of the load of the power generation plant, or even if it is not and monitoring is performed for the presence of scale membrane at the point when the load of the power generation plant has reached a predetermined value, then each of the reference value calculation portions for $\Delta T1L$, $\Delta T2L$, the differential pressure or K1L, K2L and K3L can have constant valves stored irrespective of the load (or the feed water flow).

The following is a description of other embodiments.

In the embodiments previously described, the extracted steam inlet feed water heater internal pressure detector portion 46-2 is used as the extraction steam inlet process measurement portion 46 and those measurement results are used to calculate the saturation temperature at that pressure, and this is used to calculate the heat exchange performance but in this embodiment, a temperature detector is used instead of this to measure the saturation temperature of the extraction steam. These measurement results are used to calculate the heat exchange performance.

In addition, this and the other embodiments can both measure the extraction steam pressure in the high-pressure turbine or the low-pressure turbine instead of the extracted steam inlet feed water heater internal pressure detector portion 46-2. This value can be used to calculate the pressure loss (calculated value or empirical value) of the extracted steam inside the extracted steam inlet feed water heater.

In addition, signals for the process status values that have a constant relationship with the main steam flow to the power generation plant or the feed water flow to the boiler, or the extracted steam pressure from the turbine and the load of the power generation plant can be used instead of the load signals 50 for the power generation plant and the same effect obtained.

In addition, the description for these embodiments was given for the case of when the tubes for heat exchange are steel tubes but there is still scale accretion even if they are Monel tubes and so the same effect can still be obtained even if the heat exchange tubes are not steel. Also, the description was given for the case where there was scale membrane accretion to the flow distribution devices as places other than the tubes for heat exchange but in cases where there is scale accretion to places other than the flow distribution devices and there is a reduced feed water flow path area because of the scale membrane. Then, these embodiments are effective in judging whether the portions where there is an excessive thickness of scale membrane accretion are the heat exchange tubes or at some other place.

In addition, the above description for the embodiments was given for a scale accretion monitoring apparatus monitored the feed water heater but the present invention is not limited to this. The same effect can be obtained for heat exchangers that use a method whereby water is pressure fed inside non-heat recovery boilers, recirculators or heat exchange tubes, and heat exchange is performed.

The following is a description of modifications of the second embodiment of the present invention, with reference to FIG. 15 through FIG. 30.

Figure 15:
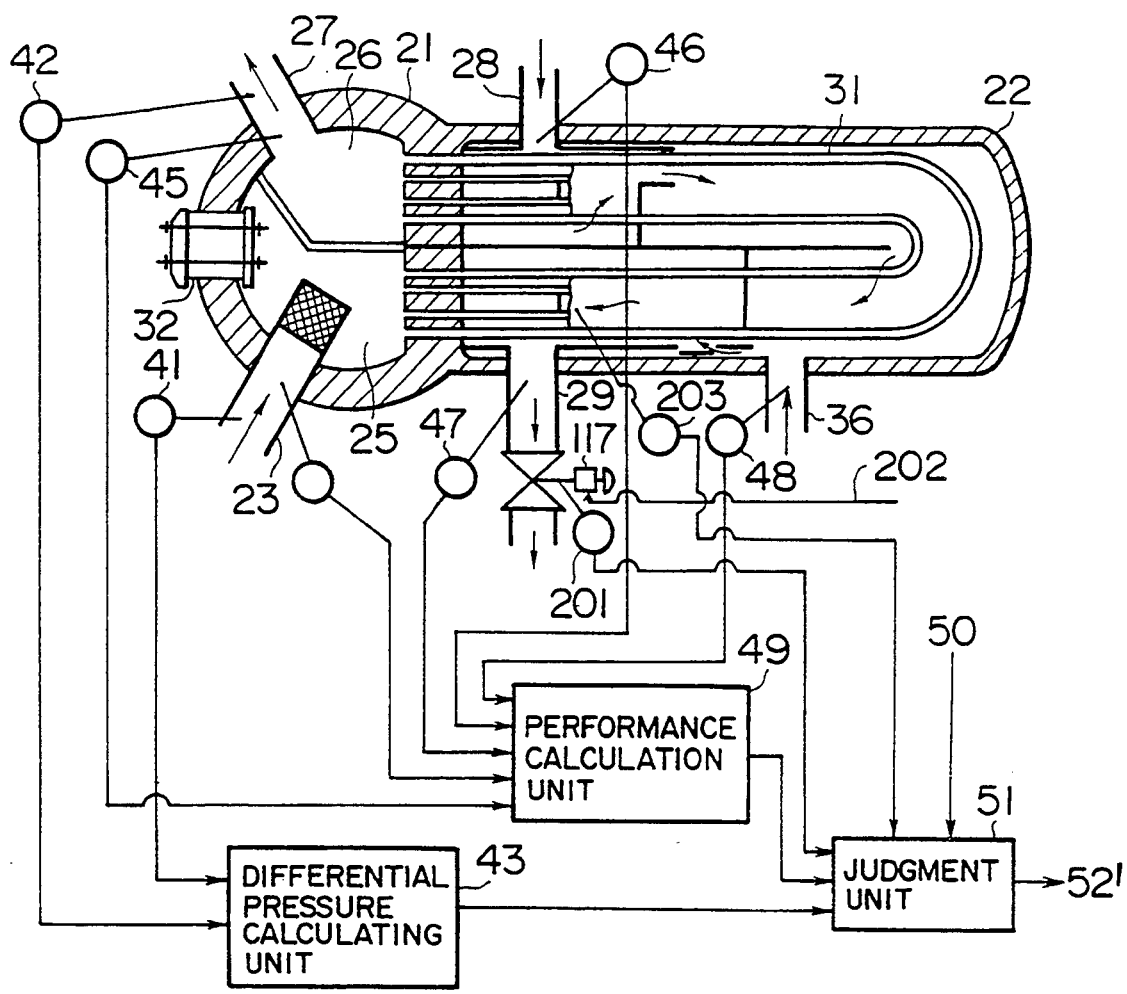
FIG. 15 is a block diagram showing an embodiment of the second invention.

In FIG. 15, there is a drain level adjustment valve 117 mounted to the drain outlet portion 29. This drain level adjustment valve 117 has a drain level adjustment valve degree of opening gauge 201 mounted to it in order to monitor the degree of opening. Those output signals are input to the judgment portion 51. The load signals 50 (L) from the power generation plant are also input to the judgment portion 51 and the abnormal judgment results 52' for the other feed water heaters and the presence of scale accretion in each of the portions of the feed water heater are output from the judgment portion 51. The other portions of the configuration are the same as for FIG. 1.

In an abnormality monitoring apparatus for a heat exchanger and having the configuration as described above, the pressure in the feed water outlet portion and the feed water inlet portion that flows into and out of the feed water heater is measured by the feed water inlet pressure measuring portion 41 and the feed water outlet pressure measuring portions 42 for the status where there is small pulsation and in the same manner as shown in FIG. 1. The respective output signals are input to the differential pressure calculating portion 43 where the differential pressure value of the feed water at the feed water outlet portion and the feed water inlet portion are calculated and the results input to the judgment portion 51. The heat exchange performance of the feed water heater can be evaluated using the amount of heat that enters the feed water heater, and the amount of heat that leaves it.

The amount of heat that enters the feed water heater is the total value of the amount of heat held by the drain that enters from the drain inlet portion, the amount of heat of the extraction steam that enters from the extraction inlet portion, and the amount of heat that is held by the feed water that enters from the feed water inlet portion, and the amounts that are necessary to calculate these amounts of heat are measured using the feed water inlet process measurement portion 44, the extraction steam inlet process measurement portion 46 and the drain inlet process measurement portion 48. On the other hand, the amount of heat that leaves the feed water heater is the total value of the amount of heat that is held by the drain that leaves from the drain outlet portion and the amount of heat that is held by the feed water that leaves from the feed water outlet portion. The associated amounts used to calculate this amount of heat are measured by the feed water outlet process measuring portion 45 and the drain outlet process measurement portion 47.

These output signals are input to the performance calculation portion 49. The calculations for the evaluation of the heat exchange performance of the feed water heater are performed, and these results are input to the judgment portion 51.

To the drain level adjustment valve 117 of the feed water heater are input the output signals from the drain level meter 203 that detects the level of the feed water heater drain cooling zone. This drain level is provided with a drain level adjustment meter (not indicated in the figure) that outputs level adjustment signals for the control of the drain level to the objective value. The drain level adjustment valve opens and closes in accordance with these level adjustment signals 202 output from the drain level meter 203. The drain flow from the drain outlet portion of the feed water heater is controlled, and the drain level of the drain cooling zone inside the feed water heater is controlled to the objective (constant) level. Accordingly, when the load for the power generation plant is the same, each of the portions of the feed water heater and the drain level adjustment valve are the same, and when the drain level is the objective value (constant value), the degree of opening of the drain level adjustment valve is a constant value in accordance with the load of the power generation plant.

The degree of opening of the drain level adjustment valve 117 is measured by the drain level adjustment valve degree of opening gauge 201 and those measurement results are input to the judgment portion 51. In addition, the output signals of the drain level meter 203 are input to the judgment portion 51.

Figure 16:
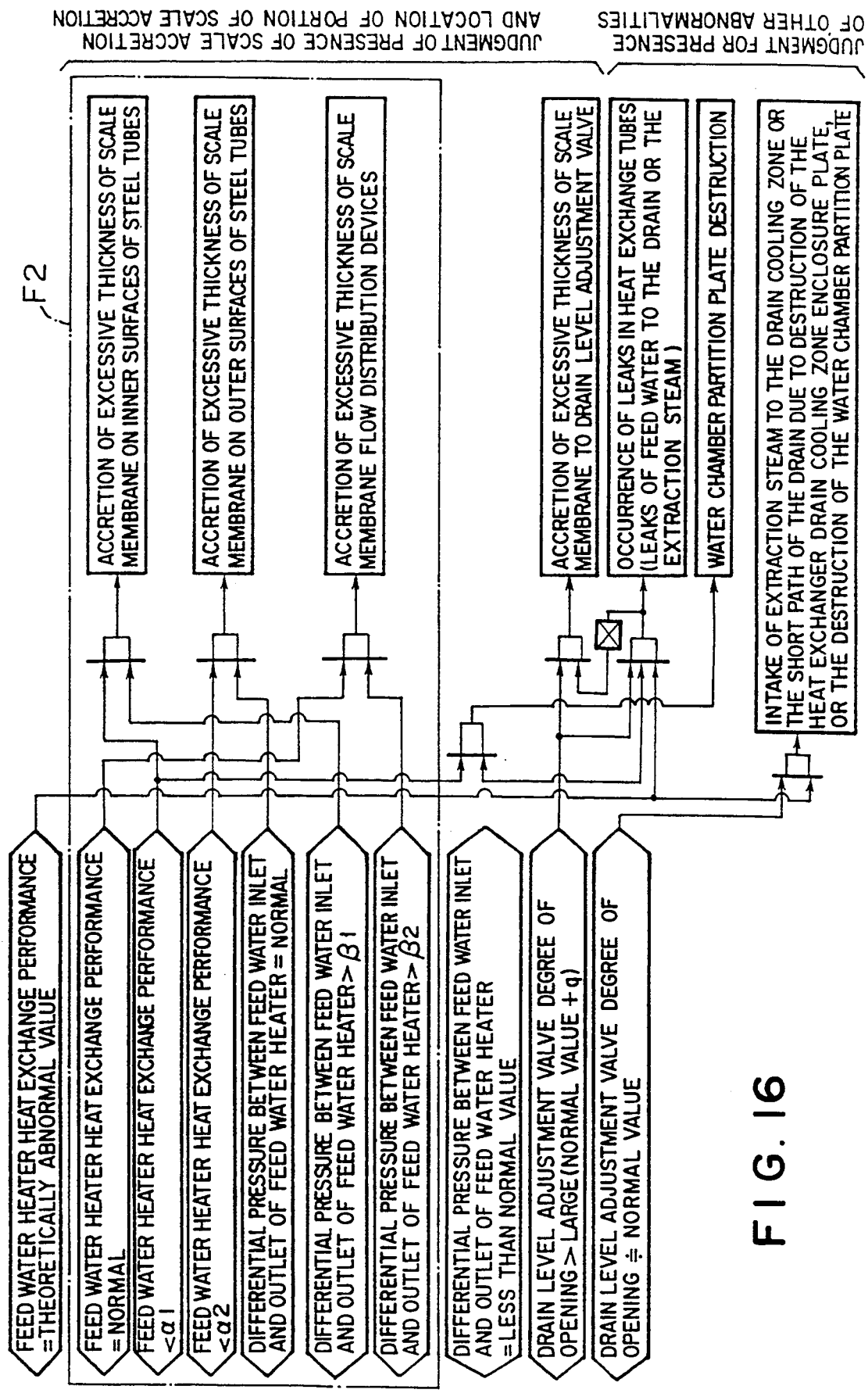
FIG. 16 is a judgment logic diagram for the embodiment shown in FIG. 15.

In addition to the calculation results and the measurement results described above, the load signals 50 of the power generation plant are also input to the judgment portion 51 where compensation according to values for the drain level and the load at that time is applied to the feed water differential pressure values, the heat exchange performance evaluation calculation results and the drain level adjustment valve degree of opening value and then these values at the same time are used so that the judgment logic in FIG. 16 judges the generation of an excessive thickness of scale membrane in what portion of the feed water heater, or the generation of other abnormalities in the feed water heater, and outputs those results 52' from the judgment portion 51.

The following is a description of the outline of the judgment logic of FIG. 16. Moreover, in FIG. 16, the configuration inside the double-dotted frame F2 is the same as corresponding portions in FIG. 2, and the description of them will be omitted.

As has already been described, the action of the drain level adjustment meter performs open and close control of the drain level adjustment valve so that the drain level of the drain cooling zone is a constant valve. So, if the load of the power generation plant is held at a substantially constant value, each of the process quantities for the drain, the extraction steam and the feed water that flow into or out of the feed water heater are also substantially constant values that correspond to the load of the power generation plant at that time. In this case, the drain amount that flows from the feed water heater is also held at a substantially constant value and so the degree of opening of the drain level adjustment valve must show a degree of opening that corresponds to the load at that time. However, when there is the accretion of an excessive thickness of scale membrane inside the drain level adjustment valve, the flow path area along which the drain can flow inside the drain level adjustment valve is reduced and so the degree of opening of the drain level adjustment valve must be increased in order for a drain amount to flow in accordance with the load of the power generation plant at that time. More specifically, even if the power generation plant has the same load, the degree of opening of the drain level adjustment valve must be made greater if there is accretion of scale membrane for the same load, so as to compensate for the degree that there is the accretion of scale membrane to the drain level adjustment valve.

Accordingly, the degree of opening of the drain level adjustment valve for each of the loads of the power generation plant is monitored and in cases where this degree of opening exceeds a set value that is greater than where there is not the accretion of a scale membrane for that load, it is possible to judge the accretion of an excessive scale membrane to the drain level adjustment valve.

However, even if there is the accretion of an excessive thickness of scale membrane to the drain level adjustment valve, then even if there are holes in the heat exchange tubes of the feed water heater or leaks of the feed water flowing in the tubes to inside the feed water heater shell 22, that is, to the side of the extraction steam or the drain, there is an increase in the drain flow by the amount of the leaking feed water. Since the drain level of the drain cooling zone is constant, the degree of opening of the drain level adjustment valve is increased to greater than normal. Accordingly, if only the degree of opening of the drain level adjustment valve is monitored and a judgment made, then it is not possible to discriminate whether the increase of the degree of opening of the drain level adjustment valve is due to the accretion of scale membrane or due to the leaking of feed water flowing inside the tubes.

With respect to this, in cases where there is no "generation of leaks in the tubes for the heat exchanger" and when the "degree of opening of the drain level adjustment valve $>$ normal value $+$ q (where q is a surplus value, and is a small, positive value)", it is possible to judge the "excessive thickness of accretion of scale membrane to the drain level adjustment valve." In addition, when the differential pressure between the feed water outlet and inlet of the feed water heater falls below a rated value for within the conditions shown on the right side of FIG. 16, is only for the case when there is destruction of the water chamber partition plate and the case where there is a leak inside the tubes for heat exchange. Although there is no change in the value measured for the differential pressure between the feed water inlet and outlet, even if there is the generation of leaks in the heat exchange tubes, there is an increase in the inlet feed water flow. As has already been described, the difference A3 between $\Delta PL$ compensated by the load signals (inlet feed water flow) has the opposite sign.

When there is a leak in the feed water due to holes in the heat exchange tubes or the like, there is not only an increase in the degree of opening of the drain level adjustment valve, but there is also the flow of one portion of the feed water to the side of the drain and so the heat exchange performance of the feed water heater shows an abnormal value that is not theoretically possible for as long as there is no destruction of the feed water heater. Accordingly, when "feed water heater heat exchange performance $=$ theoretically abnormal value," when there is "drain level adjustment valve degree of opening $>$ normal value $+$ q" and the "differential pressure between feed water heater feed water inlet and outlet $=$ less than a normal value", it is judged that "there is a leak in the heat exchange tubes (with feed water flowing to the side of the extraction steam or drain)."

When there is the destruction of the water chamber partition plate 30 of the feed water heater, one portion of the feed water inside the inlet-side water chamber 25 does not pass the heat exchange tubes 31 and flows directly to the outlet-side water chamber 26. Accordingly, there is no heat exchange between this feed water and the extraction steam and the drain and the heat exchange performance of the feed water heater drops. In addition, in this case, the differential pressure between the feed water heater inlet and outlet is the reverse of that for the case when there is scale accretion to the heat exchange tubes 31, i that it becomes lower than the normal value. It is therefore judged that there is "destruction of the water chamber partition plate" when there is "feed water heater heat exchange performance $<$ a3" and "differential pressure between feed water heater inlet and outlet $=$ less than a normal value."

In addition, when there is the destruction of the enclosure plate of the drain cooling zone 35 inside the feed water heater shell 22, and one portion of the drain does not flow along the rated flow path, and passes through the destroyed portion (which is known as the short path of the drain due to destruction of the plate enclosing the cooling zone) or when the extraction steam, that is, the heated steam is drawn into the drain cooling zone, the heat exchange performance of the feed water heater shows a theoretically abnormal value in the same manner as the case where "there is a leak inside the heat exchange tubes." However, this case differs from when "there is a leak inside the heat exchange tubes" in that the degree of opening of the drain level adjustment valve is a substantially normal value. Thus, in cases where the "degree of opening of the drain level adjustment valve is a substantially normal value", and "feed water heater heat exchange performance=theoretically abnormal value,"it is judged that there is "the inlet of extraction steam to the drain cooling zone or that there is the short path of the drain due to destruction of the plate enclosing the drain cooling zone of the feed water heater."

The judgment block of FIG. 16 shows the configuration of various types of logic circuits so that the functions described above are provided.

Figure 17:
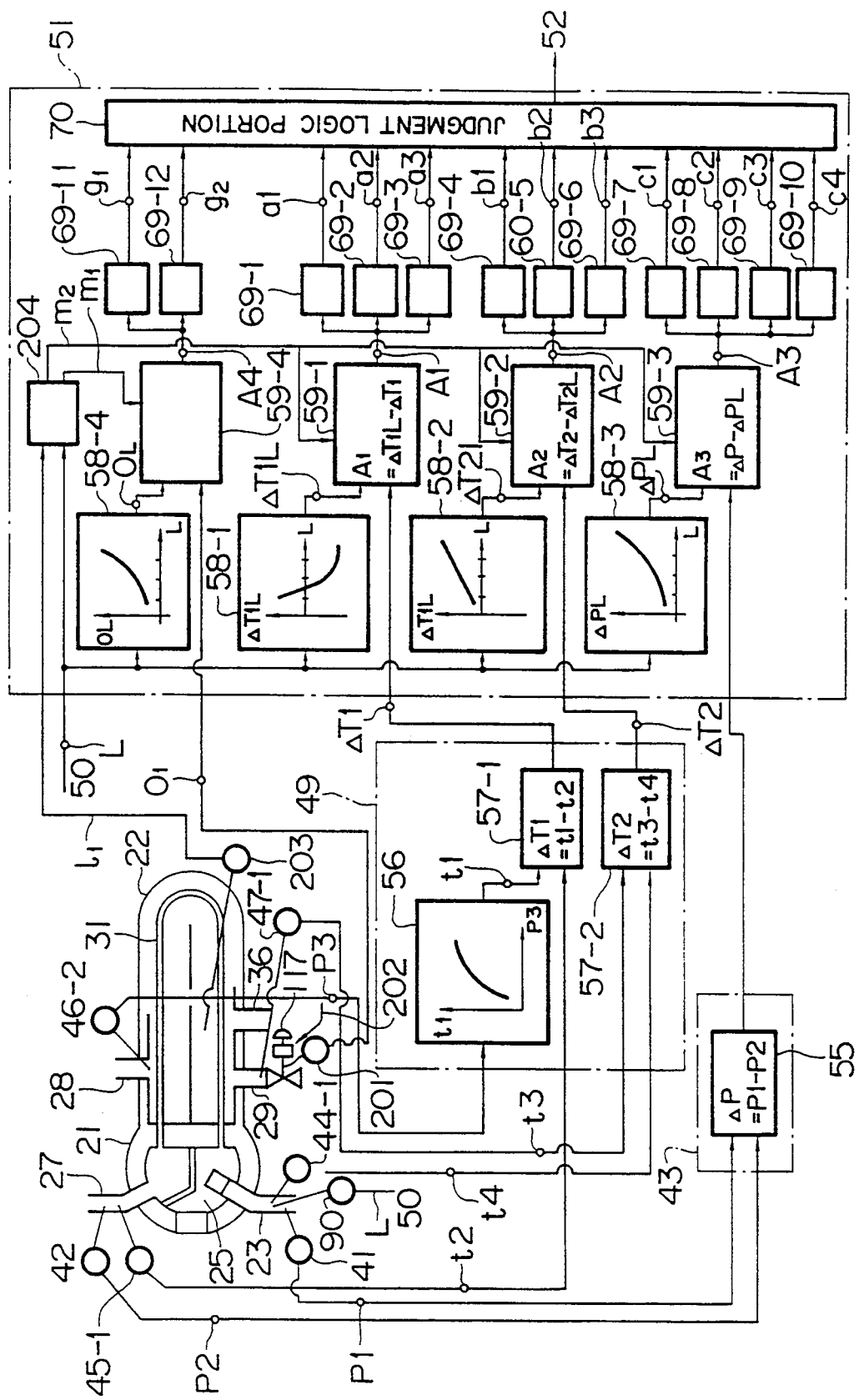
FIG. 17 is a more detailed configuration block diagram of an embodiment of the second invention.
Figure 18B:
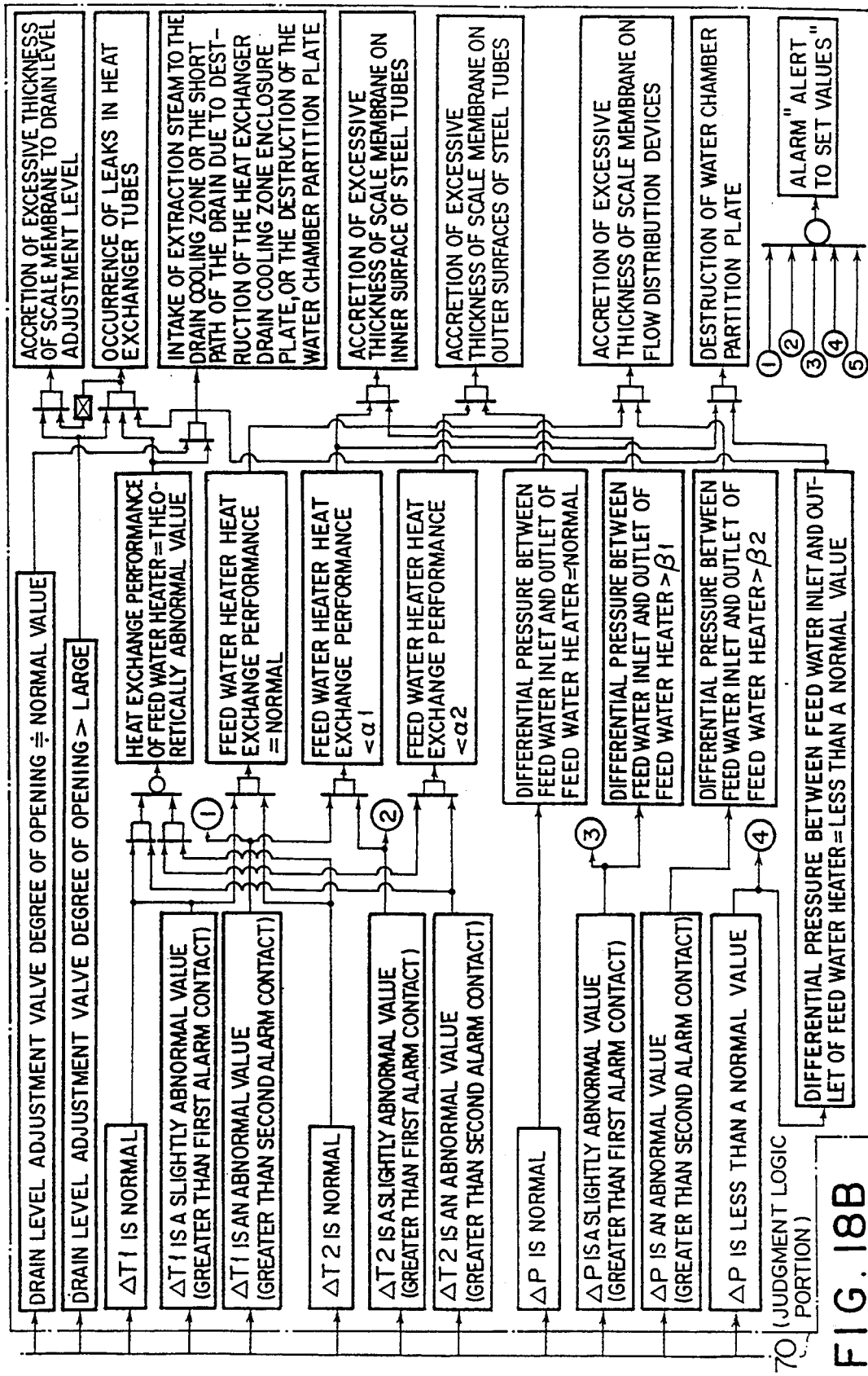
FIG. 18 is a more detailed configuration block diagram of the embodiment of FIG. 17.
Figure 19:
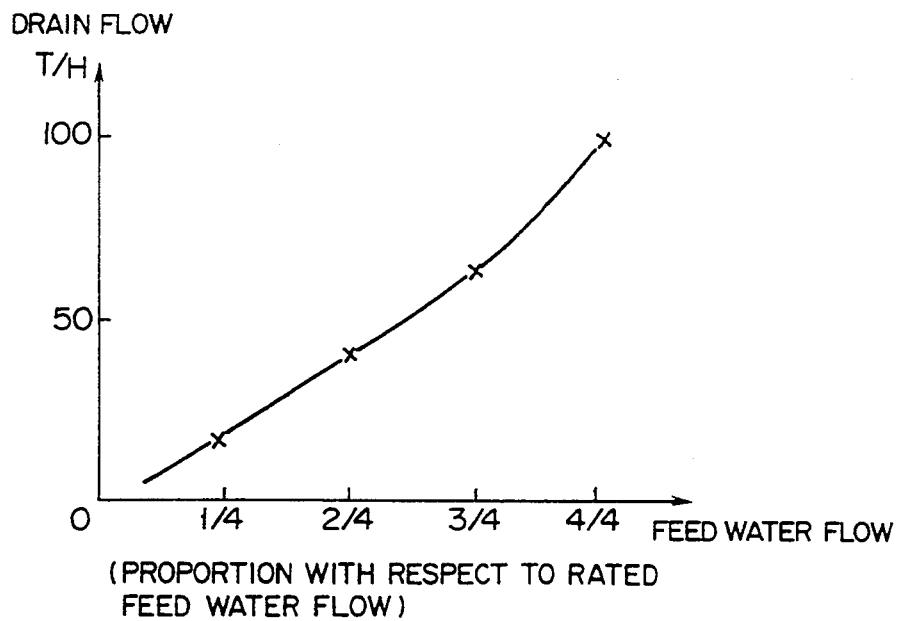
FIG. 19 is a graph showing the relationship between the drain flow and the feed water flow of a feed water heater.

The following is a detailed description of the configurations and functions of the present embodiment, with reference to FIG. 17 through FIG. 19. In this Figure, those portions that are the same as corresponding portions of FIG. 1 through FIG. 14 are indicated with the same numerals, and the corresponding description of them is omitted.

FIG. 17 is a block diagram showing a more detailed configuration of FIG. 15. In the same figure, the output signals P2 of the feed water inlet pressure measuring portion 41 and the feed water outlet pressure measuring portions 42 are input to the differential pressure calculating portion 43 configured from the subtractor 55. The feed water inlet temperature detector portion 44-1 is used as the feed water inlet process measurement portion and the drain outlet temperature detector portion 47-1 is used as the drain outlet process measurement portion, and these output signals t4 and t13 are input to the subtractor portion 57-2 of the performance calculation portion 49 and calculated. These output signals $\Delta T2$ are input to the subtractor portion 59-2 of the judgment portion 51. In addition, the extracted steam inlet feed water heater internal pressure detector portion 46-2 is used as the extraction steam inlet process measurement portion and those output signals P3 are input to the saturation temperature (t1) calculation portion 56 of the performance calculation portion 49. Those output signals t1 are input to the subtractor portion 57-1. On the other hand, the feed water outlet temperature detector portion 45-1 is used as the feed water outlet process measurement portion and those output signals t2 are also input to the subtractor portion 57-1. The output signals $\Delta T1$ of the subtractor portion 57-1 are input to the subtractor 59-1 of the judgment portion 51.

On the other hand, the degree of opening of the drain level adjustment valve mounted to the drain level adjustment valve 117 is measured using the drain level adjustment valve degree of opening gauge 201 and that output signal 01 (drain level adjustment valve degree of opening signals) are input to the subtractor portion 59-4 of the judgment portion 51.

Either the power generation plant load or the main extraction steam flow or the feed water flow that has a substantially proportional relationship to the load can be used as the load signals 50 (L) from the power generation plant but in the present embodiment, in the case where there are two (or three) feed water heaters disposed in parallel, or when the feed water is supplied to feed water heaters arranged in parallel is flowing at the same flow rates, it is possible to accurately judge the presence of abnormalities in the feed water heaters and the presence of scale accretion and so the output signals from the flow detector 90 for inlet feed water flow measurement for the feed water heater is used.

Load signals 50 are input to the OL (drain level adjustment valve degree of opening) rated value calculation portion 58-4 and the differential pressure rated value calculation portion 58-3, the $\Delta T2L$ rated value calculation portion 58-2, and the $\Delta T1L$ rated value calculation portion 58-1 of the judgment portion 51. In addition, these output signals $\Delta T1L$, $\Delta T2L$, $\Delta PL$ and OL are also input to the subtractor portions 59-1, 59-2, 59-3 and 59-4 respectively.

The output signals A1 of the subtractor portion 59-1 are input to the alarm setting portions 69-1, 69-2 and 69-3, and as a result, the ON-OFF output signals a1, a2 and a3 are input to the judgment logic portion 70'. The output signals A2 of the subtractor portion 59-2 are input to the alarm setting portions 69-4, 69-5 and 69-6 and as a result, the ON-OFF output signals b1, b2 and b3 are input to the judgment logic portion 70'. In addition, the output signals A3 of the subtractor portion 59-3 are input to the alarm setting portions 69-7, 69-8, 69-9 and 69-10 and as a result, the ON-OFF output signals c1, c2, c3, c4 are input to the judgment logic portion 70'. The output signals A4 of the subtractor portion 59-4 are input to the alarm setting portions 69-11, 69-12 and as a result, the ON-OFF output signals d1 and d2 are input to the judgment logic portion 70'.

The output signals 11 of the drain level gauge 203 and the feed water heater inlet feed water flow signals from the flow meter 90, that is, the load signals 50 (L) are input to the judgment timing detection portion 204 of the judgment portion 51. In this judgment timing detection portion 204, the judgment start command signals m1 and m2 are calculated and input to the subtractor portions 59-1, 59-2. These subtractor portions 59-1, 592 perform subtraction calculation only, and outputs the results when there is the input of the judgment start command signals m1 and m2, and outputs "0" for all other cases.

In the judgment logic 70' a judgment logic, such as that shown in FIG. 18, makes a judgment for the presence of an abnormality in the feed water heater or whether there is an excessive amount of scale membrane generated in that portion, and those scale membrane generation judgment results 52 are output as the output signals of the judgment portion 51.

The following is a description of the operation of this embodiment.

The pressure in the feed water outlet portion and the feed water inlet portion of the feed water flowing to and from the feed water heater is measured by the feed water inlet pressure measuring portion 41 and the feed water outlet pressure measuring portions 42 disposed at places where there is a small amount of pulsation, and the respective output signals P1, P2 are input to the subtractor 55 that configures the differential pressure calculating portion 43 and the calculation $\Delta P=(P1-P2)$ are performed, and as a result, the output signals $\Delta P$ are input to the subtractor portion 59-3. On the other hand, the feed water flow signals for the feed water that flows to that feed water heater at that time are input to the differential pressure reference value calculation portion 58-3 as the load signals 50 (L) for that power generation plant.

However, even in cases where there is the formation of a thin (normal status) of magnetite scale membrane for all of the inner surface of the steel tubes and the flow distribution devices and when there is no increase or decrease in that amount of generation, then the increase or decrease of the load of the power generation plant, that is, the increase and decrease of the feed water flow into the feed water heater, causes the differential pressure between the feed water inlet portion and outlet portion to increase and decrease.

FIG. 5 shows the relationship between the feed water amount flowing into the feed water heater and the differential pressure $\Delta PL$ between the feed water inlet portion and the outlet portion of the feed water heater for when there is the generation of a normal status for the magnetite scale membrane, (the case for the feed water heater closed to the boiler of a power generation plant of the 600 MW scale, and this is known beforehand for each of the feed water heaters. This relationship equation is stored in the differential pressure reference value calculation portion 58-3 and the input of the load signals 50 (L) to this enables the differential pressure rated value $\Delta PL$ for that feed water amount to be obtained. This differential pressure rated value $\Delta PL$ is also input to the subtractor 59-3.

In this subtractor 59-3, the difference $A3=(\Delta P-\Delta PL)$ that is, between the differential pressure (rated value) that should be present for the normal status, and the actually measured value for the differential pressure between the pressure of the feed water outlet portion and inlet portion for a certain feed water flow value and a certain time, is calculated for the time that the judgment start command signal m2 is being input, and those output signals A3 are input to the alarm setting portions 69-7, 69-8 and 69-9.

Moreover, one method of monitoring the heat exchange performance of the feed water heater is to monitor both the "difference between the feed water outlet temperature and the saturation temperature of the internal pressure of the feed water heater at the extraction steam inlet" and the "difference between the drain outlet temperature and the feed water inlet temperature," and to determine a heat exchange performance when this value drops is above a rated value. However, in the case of this method, it is not necessary to have a drain inlet process measurement portion 48 (FIG. 1). This method is used in the present embodiment.

More specifically, the "difference between the drain outlet temperature and the feed water inlet temperature" has the output signals P3 of the extracted steam inlet feed water heater internal pressure detector portion 46-2 input to the saturation temperature (t1) calculation portion 56 that configures the performance calculation portion 49. The process liquid that is used in power generation plants is water in many cases and in this case, the relationship between the steam pressure is as shown in FIG. 6, and this relationship equation is stored in the saturation temperature (t1) calculation portion 56. The internal pressure P3 of the extraction steam inlet feed water heater is input and the saturation temperature t1 with respect to this internal pressure P3 is calculated. These output signals t1 are input to the subtractor portion 57-1.

In addition, the output signals t2 from the feed water outlet temperature detector portion 45-1 are also input to the subtractor portion 57-1, where the calculation $\Delta T1=(t1-t2)$ is performed. Those output signals $\Delta T1$ are input to the subtractor portion 59-2 that configures the judgment portion 51. On the other hand, the feed water flow value for the feed water that flows to the feed water heater at that time are input to the $\Delta T1L$ reference value calculation portion 58-1 and the $\Delta T2L$ reference value calculation portion 58-2.

In the case where there is accretion of a thin (normal status) of magnetite scale membrane over the entire inner surface of the steel tubes, the "difference between the feed water outlet temperature and the saturation temperature of the internal pressure of the feed water heater at the extraction steam inlet" ($\Delta T1L$) and the "difference between the drain outlet temperature and the feed water inlet temperature" ($\Delta T2L$) change according to increases and decreases in the load (that is, the feed water amount flowing into the feed water heater). In this manner, the relationship between the feed water flow value flowing into the feed water heater and the $\Delta T1L$ and $\Delta T2L$ of the feed water heater for the case when there is the generation of a normal amount of magnetite scale membrane for each of the feed water heaters is known beforehand and so this relationship equation is stored in the $\Delta T1L$ reference calculation portion 58-1 and the $\Delta T2L$ reference value calculation portion 58-2 so that the input of the feed water flow value enables the $\Delta T1L$ and $\Delta T2L$ for that feed water flow to be obtained. This $\Delta T1L$ is input to the subtractor 59-1 and the $\Delta T2L$ is input to the subtractor portion 59-2.

In the subtractor 59-1 and the subtractor portion 59-2, calculations are performed for $A1=(\Delta T1L-\Delta T1)$ and $A2=(\Delta T2-\Delta T2L)$, for the duration when the judgment start signal m2 is being input. A1 and A2 represent the difference between the value that should be present normally, and the actually measured values for the "difference between the drain inlet temperature and the feed water inlet temperature" and the "difference between the feed water outlet temperature and the saturation temperature of the internal pressure of the feed water heater at the extraction steam inlet." Output signals A1 and A2 are input to the alarm setting portions 69-1, 69-2, 69-3 and 69-4, 69-5 and 69-6. In addition, the drain level adjustment valve degree of opening signal 01 measured by the drain level adjustment valve degree of opening gauge 201 mounted to the drain level adjustment valve 117 are input to the subtractor portion 59-4 that configures the judgment portion 51.

In cases when there are no abnormalities and where the load of the power generation plant is constant, the drain flow that flows from the feed water heater is also substantially constant and increases along with an increase in the load of the power generation plant. In addition, in the normal status for the feed water heater, the feed water flow to the feed water heater and the load of the power generation plant are substantially proportional. FIG. 19 shows one example for the case of the feed water heater that is closest to the boiler of a power generation plant of the 600 MW class.

Accordingly, in the normal status when there is no accretion of scale membrane to the drain level adjustment valve that allows this drain to flow, a certain relationship where the feed water flow that flows to the feed water heater and the degree of opening of the drain level adjustment valve are substantially proportional is established (this relationship is established only when feed water heater and the drain level adjustment valve are in the normal status and so the feed water flow, the drain level adjustment valve degree of opening, ΔOL differential pressure, ΔT1L, ΔT2L and other measurement values for the status regarded as normal, are stored as the reference values, which means that it is possible to judge by comparison between these values and these measured values).

In this manner, the relationship between the drain level adjustment valve degree of opening DL and the feed water flow that flows in the normal state when there is no accretion of scale membrane to the drain level adjustment valve is stored in the reference value calculation portion 58-4 (with this relationship not necessarily being calculated by theoretical calculation as the relationship between the feed water flow that flows in the normal state when the feed water heater and the drain level adjustment valve OL are in the normal state can be made by prior measurement when the power generation plant is operating). This relationship can be stored in the AL (drain level adjustment valve degree of opening) reference value calculation portion 58-4 and if the feed water flow value is input to this, it is possible to obtain the drain level adjustment valve degree of opening OL with respect to that feed water flow.

If this drain level adjustment valve degree of opening OL is input to the subtractor portion 59-4, then as will be described later, the calculation A4=(OL-01) is performed for only the duration that the judgment start command signal m1 is being input. These output signals A4 are the difference between the value that there should be (reference value) at normal times and the measured value for the "drain level adjustment valve degree of opening" for a certain feed water flow value at a certain time, and are input to the alarm setting portions 69-11 and 69-12.

The following is a description of the operation of the judgement start command signals m1 and m2 with respect to the subtractor portions 59-1 through 59-4. When the load of a power generation plant changes (or when the feed water flow changes), then the process status values for each portion are such that the pressure value and the like changes relatively quickly but the temperature value changes at a relatively slow rate. In this manner, when the load (or the feed water flow changes), it is not possible to accurately monitor ΔT1 and T2 and the like.

In addition, the drain level adjustment degree of opening is either large or small as has been described earlier when the drain level of the drain cooling zone is a value higher or lower than the objective value, so it is not possible to accurately monitor the drain level when it is stable in the vicinity of the objective value. With respect to this, the timing at which accurate monitoring can be performed is determined and the results of calculation are output from the subtractor portions 59-1 through 59-4 as output signals only at that appropriate timing, with the output signals being "0" for all other timing so that the load signals for the power generation plant (which are the feed water flow in this embodiment but which can also be signals equivalent to the load of the power generation plant, such as for the feed water flow and the like) and the drain level signal 11 which is the output signal of the drain level meter 203 are input when these input signals are a constant value for longer than a certain time, the drain level is regarded as being stable, and the judgment start command signals m1 and m2 output to the subtractor portions 59-1 through 59-4 and monitoring performed.

Figure 20:
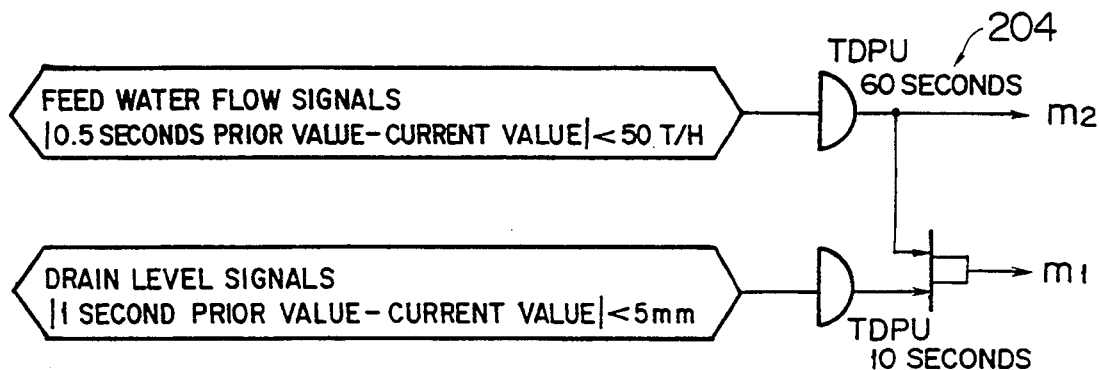
FIG. 20 is a diagram showing the judgment logic in a modification of the embodiment of the second invention.

Moreover, FIG. 20 shows a specific embodiment of the judgment timing detection portion 204 used in this embodiment.

As has been described above, the size of each of the input signals A1, A2, A3, A4 is monitored by each f the alarm setting portions 69-1 through 69-12 and when each of the input signals is greater than each of the set values, the contact signals al, a2, a3, b1, b2, b3, c1, c2, c3, c4, g1 and g2 are output to the judgment logic portion 70'. In this judgment logic portion, the judgment logic of FIG. 18 is used to judge not only whether there is the accretion of a scale membrane to the flow distribution tubes or to the inner and outer surfaces of the heat exchange tubes of the feed water heater, but also the presence of scale accretion to the drain level adjustment valves, "the generation of leaks in the heat exchanger tubes," "water chamber partition plate destruction," "intake of extraction steam to the drain cooling portion or drain short path due to destruction of the feed water heater drain enclosure," and judgments for other abnormalities in the feed water heater, and outputs those results.

According to an apparatus having the configuration described above, it is possible to monitor not only the accretion of a scale membrane to the flow distribution devices or the inner surface and outer surfaces of the feed water heater heat exchange tubes, but it is also possible to discover such while the power generation plant is operating. As a result, it is possible to discover leaks in the heat exchange tubes at an early stage and without disassembling the drain level adjustment valve when the power generation plant is not operating.

Accordingly, it is possible to plug the inlet portion and the outlet portion for the feed water in the leaking tubes so that there are no leaks of feed water (with the feed water outlet and inlet differential pressure and the heat exchange function of the feed water heater changing since there is no feed water flowing in those tubes) and to perform repairs, and also in these cases, it is possible to measure the ΔT1L, ΔT2L, ΔPL and OL with respect to each of the loads when the power generation plant is operating at that time, and to store these as normal values (reference values) so that the apparatus can function more effectively.

In addition, the destruction of the water chamber partition plate for the feed water or the generation of trouble such as the intake of extraction steam to the drain cooling portion or short path due to the destruction and loss of the drain cooling zone enclosing plate can also be detected at an early stage while the power generation plant is operating.

Furthermore, it is also possible to perform this monitoring described above for any load of the power generation plant. Still furthermore, in cases where there are a plural number of feed water heaters disposed in parallel, it is possible to have accurate monitoring even if the feed water flow to each of the feed water heaters is not the same.

The following is a description of several modifications of the second invention.

EXAMPLE 1

In the embodiment described above, as shown in FIG. 16, "AND" is the logical product for the "feed water heat exchange performance <a1" and "feed water heater feed water inlet/outlet differential pressure=normal value" were used but depending upon the structure of the feed water heater, there are instances where the accuracy of judgment is poor with only these two conditions. When there is the destruction of the water chamber partition plate, the feed water outlet temperature of the feed water heater drops suddenly by about several °C. (and although this depends upon the type of destruction, this change is between 3° C. and 10° C. in the case of this embodiment) and so this condition can also be used in the judgment.

Figure 21:
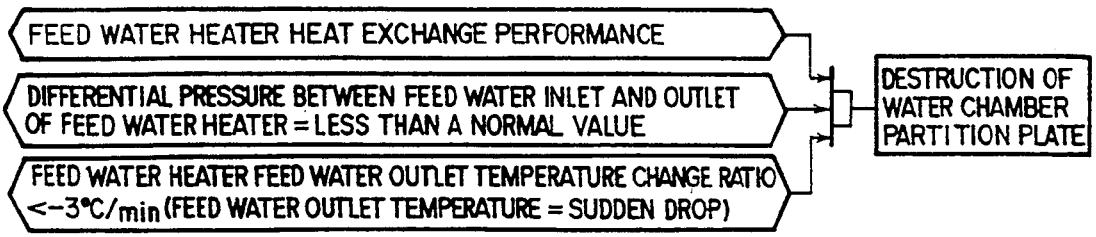
FIG. 21 is a diagram showing the judgment logic in a modification of the embodiment of the second invention.

As one example of this, as shown in FIG. 21, of the three conditions of "feed water heater heat exchange performance$<\alpha 1$," "feed water heater feed water. inlet/outlet differential pressure=less than a normal value" and "feed water heater feed water outlet temperature=sudden drop," the judgment can be made by an AND condition (logical product) between or among two or three of these conditions.

Moreover, the judgment of "feed water heater feed water outlet temperature=sudden drop" has feed water outlet temperature change ratio$< -3°$ C. as the result of tests for the present embodiment, but this value changes according to the structure of the feed water heater shell and the method of detecting the feed water outlet temperature. There is no need for this value to be definite. In addition, in the same manner as for "feed water heat exchange performance$<\alpha 1$", the same value as the value a1 used for judging the scale membrane on the inner surface of the heat exchange tubes was used but this value need not necessarily be the same.

EXAMPLE 2

In the embodiment described above, the logic for the judgment of "the generation of leaks in tubes of heat exchanger" used as shown in FIG. 16, the AND (logical product) of the three conditions of "drain level adjustment valve degree of opening$>$large," "differential pressure between feed water heater inlet and outlet=less than a normal value" and "feed water heater heat exchange performance=theoretically abnormal value" as the conditions but there is no necessity to use all of these three conditions, as only two or even one can be used. In addition, a leak detection method that detects leaks in the heat exchanger tubes by the flow pressure difference between the feed water inlet and outlet of the feed water heater, or through the use of an acoustic detector can also be used to further improve the judgment's accuracy.

In addition, when there is a leak in the tubes, the drain flow increases and so in this embodiment, monitoring of "drain level adjustment valve degree of opening$>$large" was used to detect this, but "drain level adjustment valve degree of opening$>$large" also occurs when there is the "generation of an excessive accretion of scale membrane in the drain level adjustment valve" as well as when there are leaks in the tubes. So, it is difficult to discriminate between these and a judgment error occurs as shown in FIG. 13. In power generation plants where the drain outlet flow is measured, instead of the drain level adjustment valve degree of opening signal 01 of FIG. 17, the drain outlet flow signals are input. On the other hand, the drain outlet flow with respect to the load signals (with the feed water inlet flow being used in this embodiment) for when the power generation plant is operating normally can be input to the OL (drain level adjustment valve degree of opening) reference value calculation portion 58-4 and are stored as reference values and the judgement made.

Figure 22:
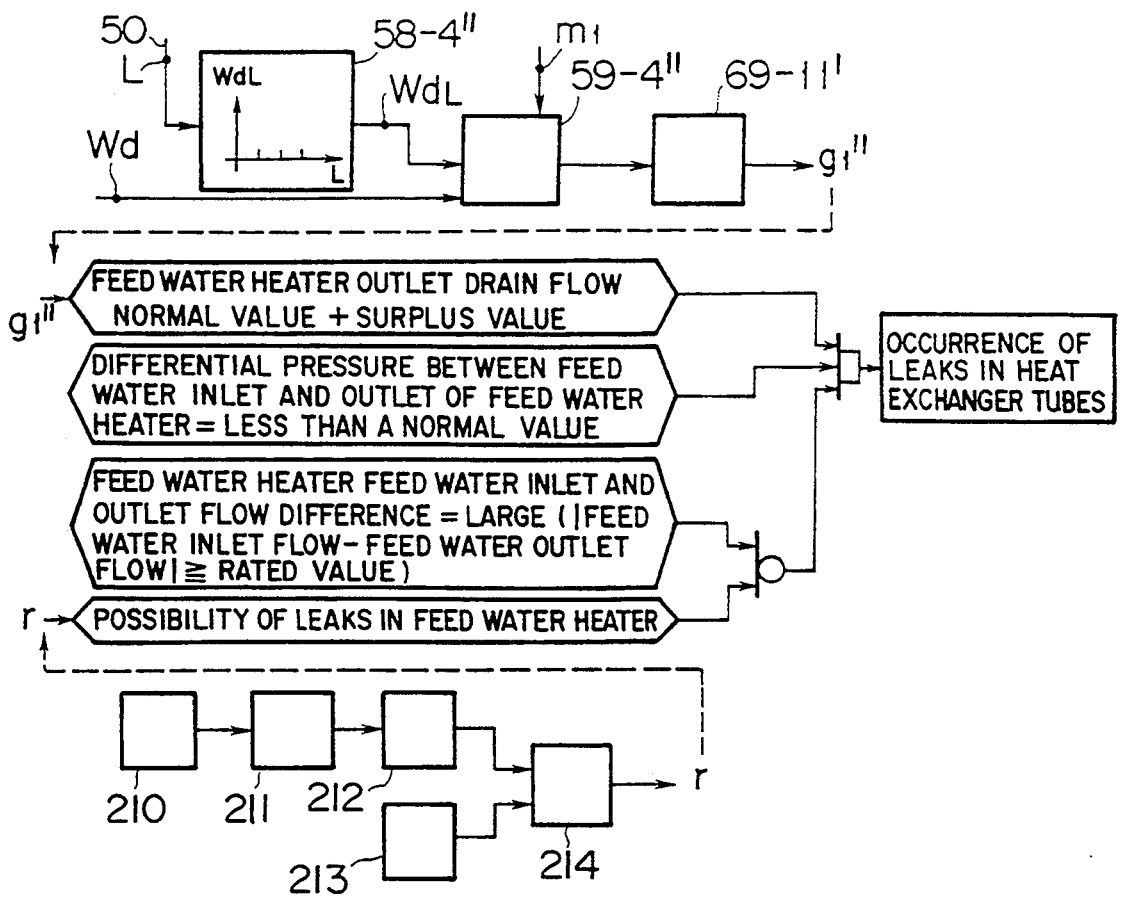
FIG. 22 is a diagram showing the judgment logic in a modification of the embodiment of the second invention.

FIG. 22 shows one example of the judgment block and the configuring blocks. In the same figures, 58-4" is a WdL (drain outlet flow) reference value calculation portion, 59-4" is a subtractor portion, and 69-11" is an alarm setting portion. The output g1" of this alarm setting portion is input to the AND circuit when "feed water heater outlet drain flow$>$normal value+surplus value."

On the other hand, the acoustic detector portion 210 is mounted to the feed water heater shell and detects the sound that is transmitted inside the feed water heater. After there has been signal amplification at the amplifier portion 211, there is frequency analysis at the frequency analyzer portion 212. In addition, the results of frequency analysis of the sounds transmitted inside the feed water heater when there is normal operation for when there are no leaks in the tubes of the heat exchanger of the feed water heater, are stored in the reference pattern storage portion 213 as the reference pattern. The frequency analysis results from the frequency analysis portion 212 are compared in a comparator portion 214 with the pattern that is stored in the reference pattern storage portion 213 and when it is thought from the frequency analysis results that a leak has occurred in the tubes, a signal r for "possibility of leak in feed water heater" are output. This signal is led to the judgment block where "leak occurrence in heat exchanger tubes" is judged.

EXAMPLE 3

As has been described above, in the embodiment shown in FIG. 16, the logic for the judgment of "generation of excessive thickness of scale membrane in drain level adjustment valve" used an AND condition (logical product) of "no occurrence of leaks in heat exchanger tubes," and "drain level adjustment valve degree of opening$>$large" that has been compensated by the drain level adjustment valve degree of opening as the reference value corresponding to the feed water inlet flow of the feed water heater or the load of the power generation plant. This means that when there is accretion of an excessive thickness of scale membrane to the drain level adjustment valve, and a drain outlet flow corresponding to the load of the power generation plant is made to flow, then the required drain outlet flow will not flow even if the drain level adjustment valve is opened to the same 'degree of opening as when there was no accretion of scale membrane is opened, and so the drain level adjustment valve has to be opened further and so this is used for Judgment. However, "drain level adjustment valve degree of opening$>$large" can be thought of as occurring either when as described for Example 2, when there is the "generation of an excessive thickness of scale membrane on drain level adjustment valve" and "occurrence of leak in heat exchanger tubes. So, a comprehensive judgment must be made in consideration of other factors in order to discriminate between the two.

Figure 23:
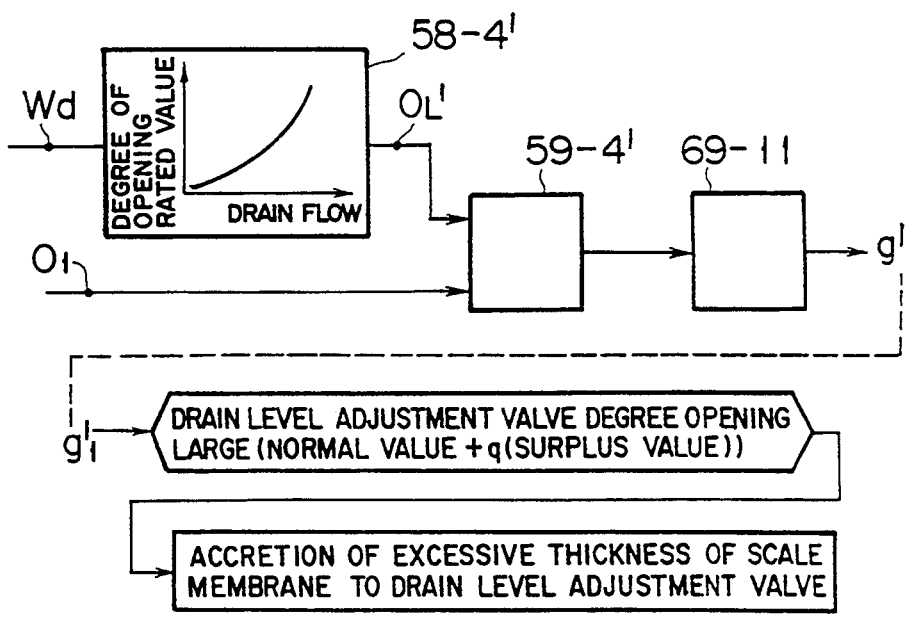
FIG. 23 is a diagram showing the judgment logic in a modification of the embodiment of the second invention.

In this case, as shown in FIG. 13, for example, in the power generation plant where the drain outlet flow is also measured, the judgment logic and the configuring blocks used are shown in FIG. 23. In the same figure, the drain outlet flows for each of the loads when the power generation plant is operating in the normal status, and the relationship with the drain level adjustment valve degree of opening are stored in the OL (drain level adjustment valve degree of opening) reference value calculation portion 58-4. When the drain outlet flow signal Wd for an arbitrary load of the power generation plant is input to the OL reference value calculation portion 58-4, the drain level adjustment valve degree of opening reference value OL' is output so as to correspond to the input. This OL' has the meaning of the degree of opening of the drain level adjustment valve which is necessary to allow the drain outlet flow Wd to flow in the normal status where there is no accretion of scale membrane to the drain level adjustment valve.

This OL' and the degree of opening signals 01 in the status of the drain level adjustment valve for that load, are input to the subtractor portion 59-4 where the calculation (01-OL') is performed and the calculation results input to the alarm setting portion 69-11. Then, when (01-OL')≧q (surplus value), the contact signal g1' is output from the alarm setting portion 69-11'.

This contact signal g1' means that "drain level adjustment valve degree of opening>large (normal value+q (surplus value)" and accordingly, the output of this signal g1 indicates the "generation of an excessive thickness of scale membrane in the drain level adjustment valve."

For the case shown in FIG. 16, the drain level adjustment valve degree of opening with respect to the feed water inlet flow or the load of the power generation plant is made the reference value. The deviation with respect to this is monitored, but with this method, for example, when there is "drain level adjustment valve degree of opening>large" it is not possible to distinguish between "generation of an excessive thickness of scale membrane on the drain level adjustment valve" and the "occurrence of a leak in heat exchanger tube." In order to improve the accuracy of discrimination between these two, a comprehensive judgment can be made by monitoring some other factor, such as the "feed water heater heat exchange performance=-theoretically abnormal value" which is the result of performing calculations using the values for the temperature for each portion where the accuracy of temperature measurement is relatively poor.

On the other hand, the judgement logic portion of FIG. 22 and FIG. 23 uses the measurement results for the "outlet drain flow," the "feed water inlet and outlet differential pressure" and "drain level adjustment valve degree of opening" and the like that have a relative high degree of measurement accuracy, and configures direct judgment logic for "generation of excessive thickness of scale membrane on drain level adjustment valve" when the drain level adjustment valve degree of opening is larger than the value for the normal status drain level adjustment value with respect to that drain outlet flow.

In addition, supposing that the actual drain outlet flow is large when compared to the drain outlet flow (reference value) at a load of the power generation plant that is operating in the normal status, those status values are used as one of the conditions of the judgment logic for "occurrence of leaks in heat exchanger tubes" as in FIG. 22, and without using the judgment logic for the "generation of an excessive thickness of accretion of scale membrane in drain level adjustment valve" of FIG. 23.

EXAMPLE 4

In the embodiment described above, the judgment timing detection portion 204 shown in FIG. 20 uses the flow signals to output the judgment start command signals m2 by detecting that the load is stable, but this can be either the load signals of the power generation plant or the main steam flow signal.

Also, in the embodiment described above, there is a stable load when the difference between the current value and the value 0.5 second before is within 50 T/H and when this continues for 60 seconds or more. But these values differ according to the power generation plant and, according to this method of measurement and so this is not a fixed value. More specifically, the timing for when the load has become stable to the extent that the measurement results for the temperatures and the like of each of the portions of the feed water heater have dropped to normal values (and are not transitional values) can be judged and the judgment start command signal m2 can be output.

In the same manner, in the embodiment described above, outputting the judgment start command signal m1 can have the judgment condition as to when the difference between the current value for the drain level signal and the value one second before is within 5 mm, and when this continues for 10 seconds or more, but these are not necessarily fixed values.

In addition, instead of the drain level signal, the drain level adjustment valve degree of opening signal or the drain level adjustment meter output signal can be used, and instead of the difference between the current value and a value several seconds before, the difference between the objective value for the drain level adjustment and the current value for the drain level signal being within a reference value and having this situation continue for more than a rated time can be used for the judgment.

Furthermore, when there are a comparatively small number of leaks and it is possible for there to be a greater flow from the drain level adjustment valve," the logic for the judgment timing detection portion, as described above, can be used. But when the leak amount increases and there cannot be sufficient flow from the drain level adjustment valve, the drain level adjustment valve is fully opened. When the drain cannot be discharged even when this is done, the drain level signals continue to rise to the limit value. In cases such as these, it is necessary to judge "generation of leaks in heat exchanger tubes" irrespective of the output of judgment start command signals m1.

In addition, the drain level adjustment meter output signals, when the drain level adjustment valve degree of opening signals and the like are used for monitoring the abnormalities described above, these two signals can be monitored and compared so that the status 'drain level adjustment valve sticking" at which the accretion of scale membrane to the drain level adjustment valve become excessive, to the extent that the drain level adjustment valve no longer moves, can be judged. In addition, it is also effective to monitor other "drain level adjustment valve operation abnormalities."

Figure 24:
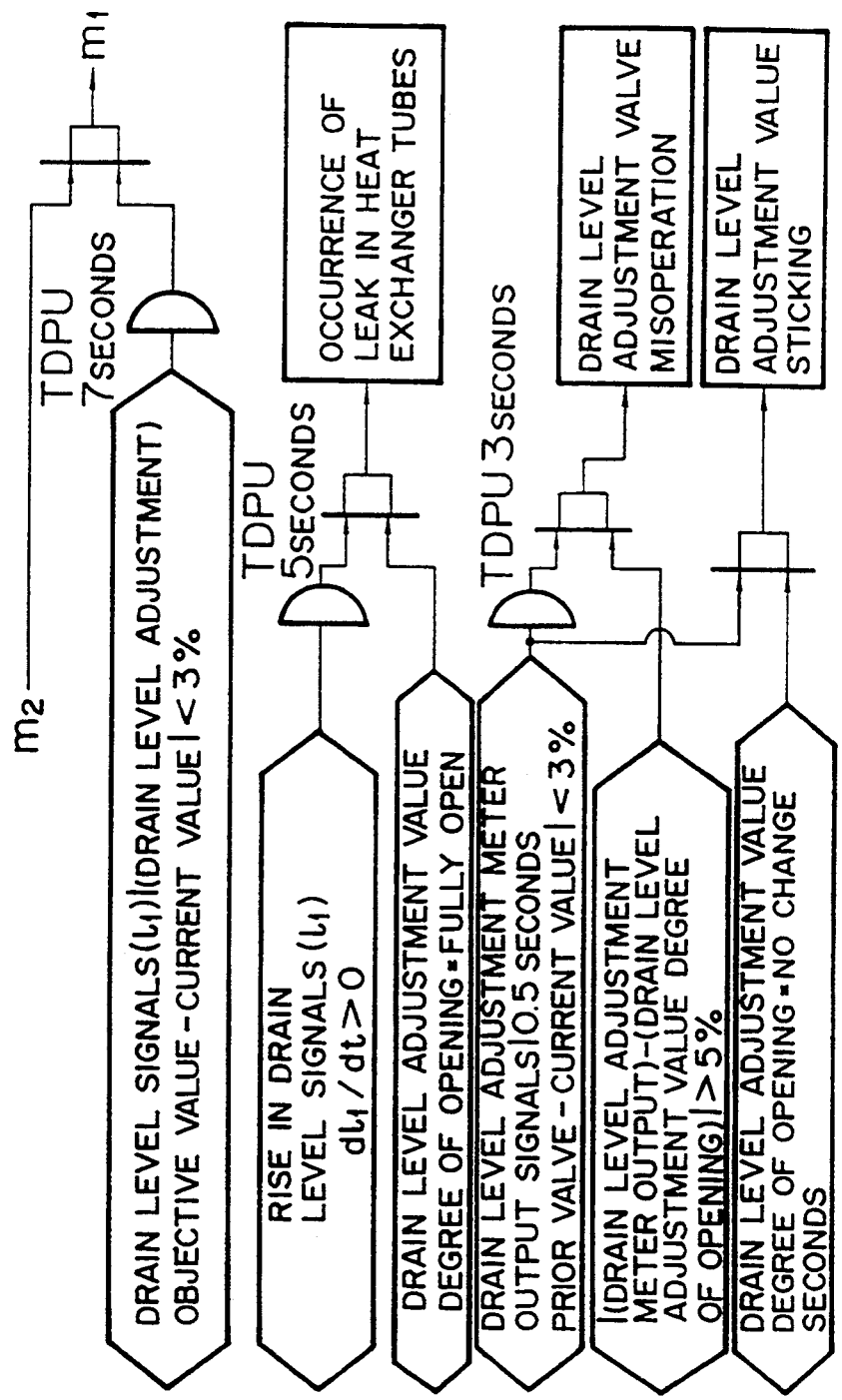
FIG. 24 is a diagram showing the judgment logic in a modification of the embodiment of the second invention.

FIG. 24 shows one example of the judgment logic for the realization of these functions.

EXAMPLE 5

In the embodiment shown in FIG. 17, the measurement values from the flow detector 90 for inlet feed water flow measurement for the feed water heater were used instead of the load signals 50 (L). But the load signals 50 (L) can use the load signals from the power generation plant as they are. These input for calculations at each of the reference value calculation portions and the output signals Wf of the flow detector 90 for inlet feed water flow measurement for the feed water heater input to the subtractor portion 59-5 of FIG. 25 so that this measurement has the intake feed water flow WfL that there should be and corresponding to the load signals for the power generation plant at that time and which are output from the WfL (intake feed water flow) reference value calculation portion 58-5, subtracted from it in the subtractor portion 59-5 and these can then be compared by input them to the alarm setting portion 69-13.

When the intake feed water flow value is monitored in this manner, that value indicates that there is substantial agreement with the intake feed water flow value that they should correspond to the load signals at that time if the power generation plant and the feed water heaters that it includes are in the normal status. When the intake feed water flow value has increased from what it was before, then it is possible that there is either "destruction of the water chamber partition plate" or a "leak in heat exchanger tubes."

Figure 26:
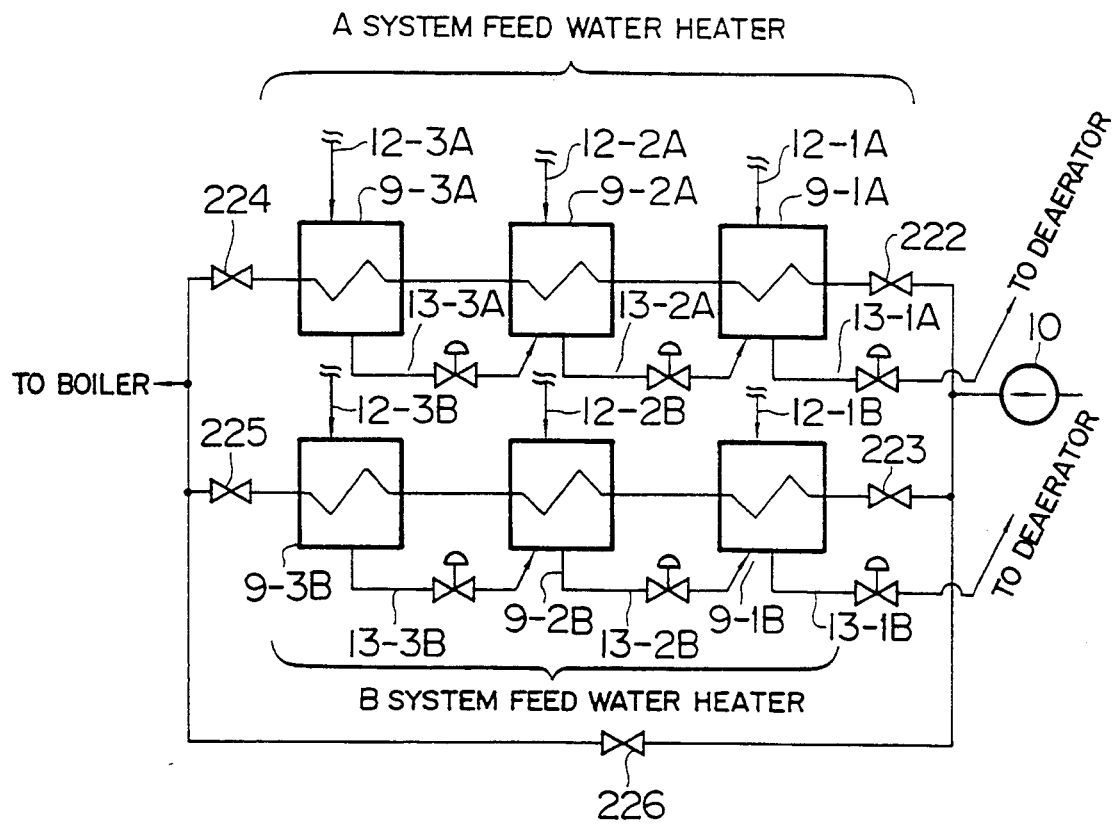
FIG. 26 is a system diagram showing the case for a parallel configuration of a plural number of feed water heaters to which the present invention has been applied.

In addition, as shown in FIG. 26, another possible cause is in cases where approximately half of the feed water that is sent from the feed water pump 10 when the feed water heaters are disposed in parallel in the two systems of an A system and a B system, passes through the feed water heaters 9-1A, 9-2A and 9-3A, and the remaining feed water passes the feed water heaters 9-1B, 9-2B and 9-3B, and mixes after this, and is sent to the boiler, where for example, there is little accretion of the scale membrane to the feed water flow path portion of the feed water heaters of the A system, and where there is an excessive accretion of scale membrane to the feed water path portion of the B system, which consequently has an increase in the flow path resistance. Thus, there is a reduced flow for the inlet feed water flow that flows in it, and that portion is an increase in the inlet feed water flow on the side of the A system. In order to judge this, in cases where there is an increase in the inlet feed water flow on one of the feed water heaters disposed in parallel, it can be thought that there is the possibility of "excessive accretion of scale membrane in the flow distribution devices or the inner surface of the heat exchanger tubes of the feed water heater on the other of the systems."

Accordingly, in the embodiment shown in FIG. 26, in cases when the inlet feed water flow has been measured by the flow detector 90 for inlet feed water flow measurement for the feed water heater and which is mounted to the inlet side of the A system feed water heater, there is an increase in this inlet feed water flow. In these cases, the cause can be thought of as the "occurrence of leaks in the heat exchanger tubes" or "destruction of the water chamber partition plate," or that there is the "excessive accretion of scale membrane in the flow distribution devices or the inner surface of the heat exchanger tubes of a feed water heater in the B system and an increase in the flow path resistance resulting from this (that is, when there is a reduction in the inlet feed water flow on the side of the B system because there is an increase in the differential pressure of the feed water inlet and outlet of a feed water heater on the B system).

Figure 25:
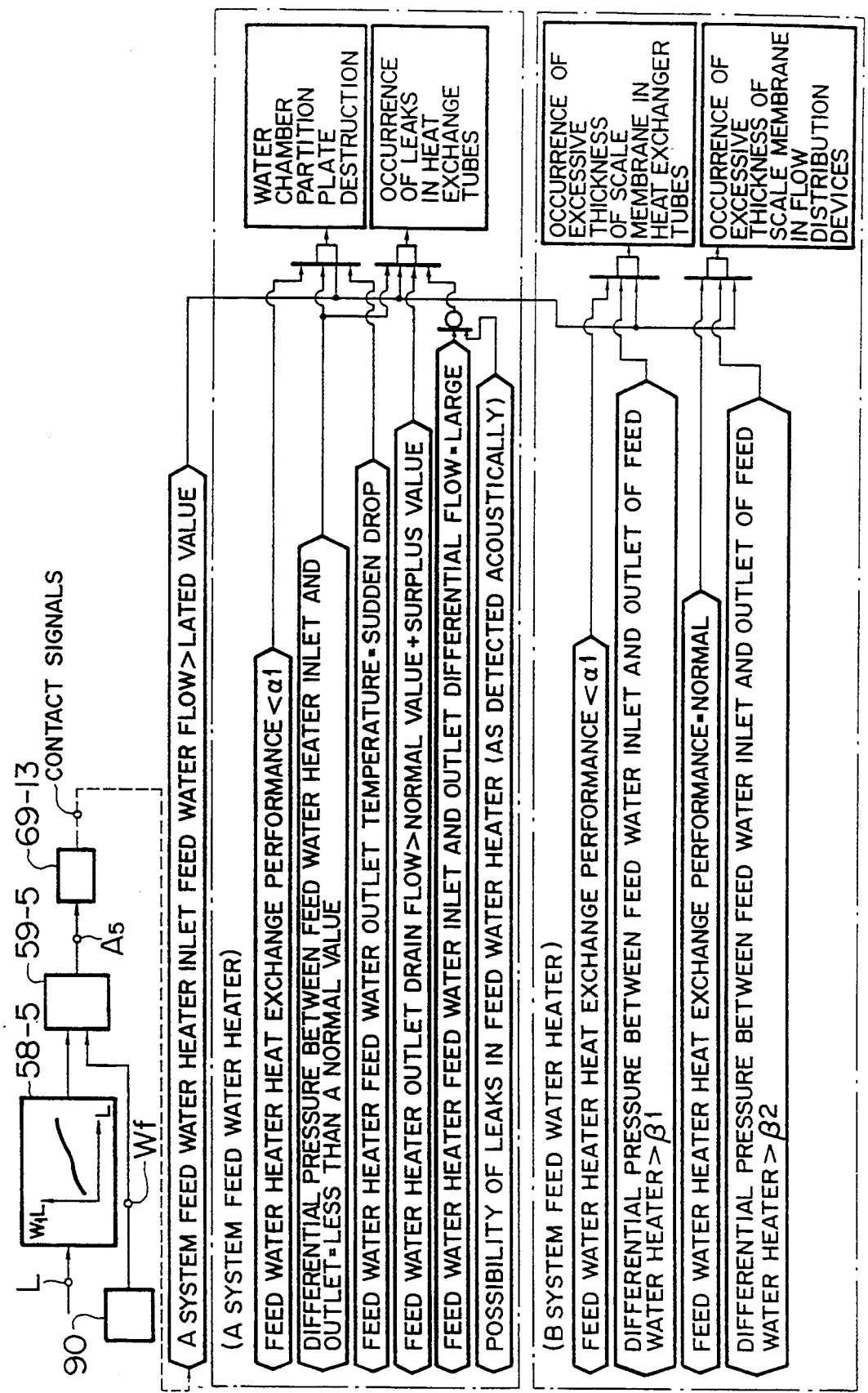
FIG. 25 is a diagram showing the judgment logic in a modification of the embodiment of the second invention.

Because of this, as shown in FIG. 25, when there is a comprehensive judgment of the "A system feed water heater inlet feed water flow > rated value" in addition to the judgment condition of the judgment logic of the B system feed water heater and the A system feed water heater, then there can be discrimination for whether the increase in the inlet feed water flow is due to scale membrane accretion to the feed water flow path portion of other feed water heaters disposed in parallel, whether it is due to "water chamber partition plate destruction" or it occurrence of leaks in heat exchanger tubes" on the side of that feed water heater.

In the same manner, if the judgment condition "A system feed water heater inlet feed water flow > rated value" of FIG. 25 is added (input of AND circuit) to the judgment logic of FIG. 22 or FIG. 21, then the accuracy of judgment is further increased. In addition, it is also possible to raise the accuracy of judgment in the same manner if "A system feed water heater inlet feed water flow > rated value" is added to (input of AND portion) the judgment conditions for judging whether there is the "accretion of excessive thickness of scale membrane to flow distribution devices" or "accretion of excessive thickness of scale membrane to inner surfaces of heat exchanger tubes" relating to the other drain level adjustment valve disposed in parallel with the feed water heater of FIG. 16.

EXAMPLE 6

Moreover, in each of the embodiments shown in FIG. 16, FIG. 21, FIG. 22 and FIG. 25 and the like, the "feed water inlet and outlet differential pressure" $\Delta P$ and "inlet feed water flow" Wf are respectively measured and monitored, but there is a close relationship between these two. More specifically, the following relationship is approximately established:

$$Wf = A \cdot \Delta P^{\frac{1}{2}}$$

Where A is a constant determined by the feed water flow path resistance and the like, and, accordingly, decreases for the greater the accretion of scale membrane to the feed water flow path of the flow distribution devices and the inner surfaces of the heat exchanger tubes.

On the other hand, as described above for Example 5, when despite the fact that the accretion of scale membrane in the feed water flow path portions of the feed water heaters of one system is as it has been (with A being constant in this case), then the accretion of scale membrane to the feed water flow path of the feed water heaters of the other system becomes excessive and the feed water flow is reduced, so that as a result, when there is an increase in the intake feed water flow of the system in question, the differential pressure of the feed water inlet of that feed water heater increases so as to correspond to it, and $Wf/\Delta P1/2$ (=A) is an approximately constant value.

However, those feed water heaters of the other system and for which the accretion of scale membrane has become great have a large increase in the feed water intake/outlet differential pressure and $Wf/\Delta P^{\frac{1}{2}}$ decreases. In addition, when there is "destruction of the water chamber partition plate," the feed water intake/outlet differential pressure reduces and as a result there is an increase in the inlet feed water flow so that $Wf/\Delta P^{\frac{1}{2}}$ increases in this case. On the other hand, when there is "occurrence of leaks in heat exchanger tubes," one portion of the feed water that flows from the intake side of the feed water heater does not reach the outlet and flows to the side of the drain or the extraction steam of the feed water heater and so there is an apparent increase in $Wf/\Delta P^{\frac{1}{2}}$.

Figure 27:
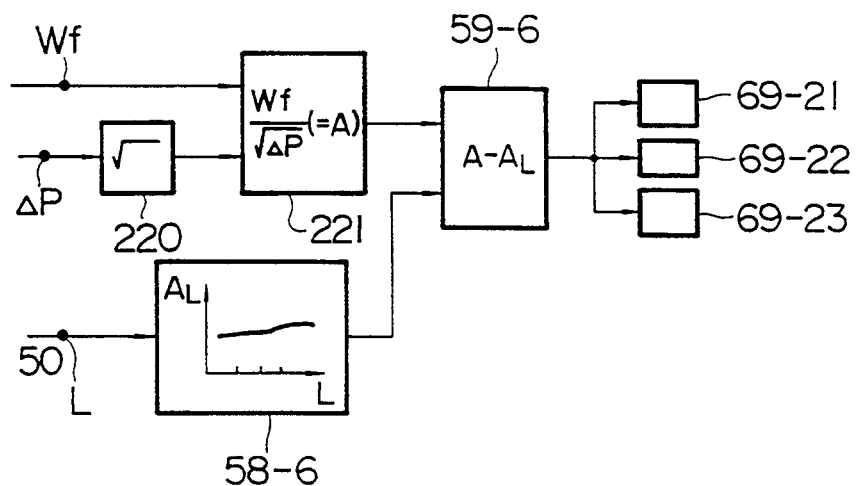
FIG. 27 is a diagram showing the judgment logic in a modification of the embodiment of the second invention.

Accordingly, by monitoring the value for A, that is, by monitoring the change with time of the value for $Wf/\Delta P^{\frac{1}{2}}$, it is possible to accurately judge the cause of "change in the inlet feed water flow of feed water heater." FIG. 27 shows one example of the configuration of a block that realizes this.

In FIG. 27, the "feed water inlet and outlet differential pressure" ΔP has the square root extracted via the square root extraction portion 220 and is then led to the division calculation portion 221 along with the "inlet feed water flow" and division calculation performed. On the other hand, the load signals 50 (L) are input to the AL rated value calculation portion 58-6 and the AL rated value obtained is input to the subtractor portion 59-6 along with the output of the division calculation portion 221. The output of the subtractor portion 59-6 is input to the alarm setting portions 69-21 through 69-23.

In this manner, the Wf/ΔP^½ from the division calculation portion 221 is compared with the AL rated value in the subtractor portion 59-6 and monitoring performed for whether it is substantially constant, increasing or decreasing, and the monitoring results, that is, the contact signals from the alarm setting portions 69-21 through 69-23 are input instead of the "inlet feed water flow" and the "differential pressure of the feed water outlet and inlet" which are the conditions for judgment in FIG. 16, FIG. 21, FIG. 22, FIG. 25 and the like so that it is possible to have the great effect of being able to have more accurate judgment.

Moreover, in the example shown in FIG. 27, the method used involves comparing the Wf/ΔP^½ measured with respect to each load. This is stored in the AL rated value calculation portion 58-6 as a reference value, with the results of calculation of this reference value AL, the measured value Wf and the ΔP for each load but depending upon the power generation plant, there are occasions where Wf/ΔP^½ is substantially constant irrespective of each of the loads when the feed water heaters are in the normal status and so the AL reference value calculation portion 58-6 is not always necessary and can be omitted in some situations. In addition, in the description for Example 6 and in FIG. 27, the following equation $$Wf = A \cdot \Delta P^{\frac{1}{2}}$$

was used as the relationship equation for the inlet feed water flow and the feed water inlet and outlet differential pressure but this is more accurately written as follows.

$$\Delta P \alpha Wf^n$$

EXAMPLE 7

In each of the modifications of the embodiments described above, the inlet feed water flow was measured by the flow detector 90 for inlet feed water flow measurement for the feed water heater.

However, in the case of a single system of feed water heaters such as is shown in FIG. 31, the flow detector can be installed in a place where the inlet feed water flow (which is equivalent to the feed water flow) can be easily measured. However, in the case where there is a plural number of systems of feed water heaters, such as is shown in FIG. 26 (the two systems A and B in FIG. 36), the intake feed water flow must be measured where it flows into each of the feed water heaters. So, the flow detectors 90 for inlet feed water flow measurement for the feed water heaters must be mounted after the feed water pipes have branched. However, with some power generation plants, it is difficult to install these flow detectors because of the structure of the feed water piping.

In cases such as these, as described with respect to FIG. 5 above, instead of installing the flow detectors 90 for inlet feed water flow measurement, to the side of the feed water heater inlet of the respective systems, the detectors can be installed on the side of the feed water heater outlets. In some cases, however, instead of providing the flow detectors 90, the configuration shown in FIG. 28 can be provided. The following is a description of FIG. 26.

In FIG. 26, the feed water heater bypass valve 226 is normally fully closed and of that feed water from the feed water pump 10, that to the A system passes through the A system feed water inlet valve 222 and after it has flown through the inside of each of the feed water heaters 9-1A through 9-3A, it passes through the A system feed water outlet valve 224 and is pressure fed to the boiler. On the other hand, that to the B system passes through the B system feed water outlet valve 224 and after it has flown through the inside of each of the feed water heaters 9-1B through 9-3B of the B system, it passes through the B system feed water outlet valve 225 and after combines with the A system feed water and is pressure fed to the boiler. In the same figure, 12-1A through 12-3A, 12-1B through 12-3B show the extraction steam pipes and 13-1A through 13-3A, and 13-1B through 13-3B show the drain pipes.

In power generation plants, the respective feed water heaters, feed water inlet valves, feed water outlet valves and the like of the A system and the B system, are generally constructed to the same specifications and so when there is the normal status for a power generation plant that includes feed water heaters, the feed water flow that flows into both the A system and the B system is generally to the same value. In a situation such as this, when there is approximately the same degree of scale membrane accretion to the feed water flow paths of the feed water heaters of both the A system and the B system, the respective intake feed water flows are practically the same value.

But when there is an excessive accretion of scale membrane to either the A system or the B system, the flow path resistance of that feed water flow path becomes larger so that there is a reduction in the intake feed water flow that flows into that system, while there is an increase by that portion, in the intake feed water flow that flows into the other system and the feed water flow is held at a total value which is constant. In this case, it is necessary to determine the feed water flow corresponding to the load of the power generation plant and so the flow corresponding to this is pressure fed to the boiler. In addition, the total feed water flow to the boiler must be measured in the power generation plant.

On the other hand, for either of the feed water heaters of the A and B systems, when there is the "destruction of the water chamber partition plate" or the it occurrence of leaks in the heat exchanger tubes," the intake flow amount to that system is greatly increased.

However, in power generation plants, the feed water intake valves 222, 224 of the A system and the B system are normally used in a status where the degree of opening is practically fixed at fully open, and when there is a large failure such as the "occurrence of leaks in the heat exchanger tubes" for either of the feed water heaters, then only in the case where the feed water heaters of that system are isolated (removed from operation) is the feed water heater bypass valve 226 opened to a suitable degree and the feed water heater inlet valve and the feed water outlet valve of that system fully opened. In this manner, the feed water intake valve is used in the status where it is almost fully open, and so there is practically no accretion of scale membrane.

Figure 28:
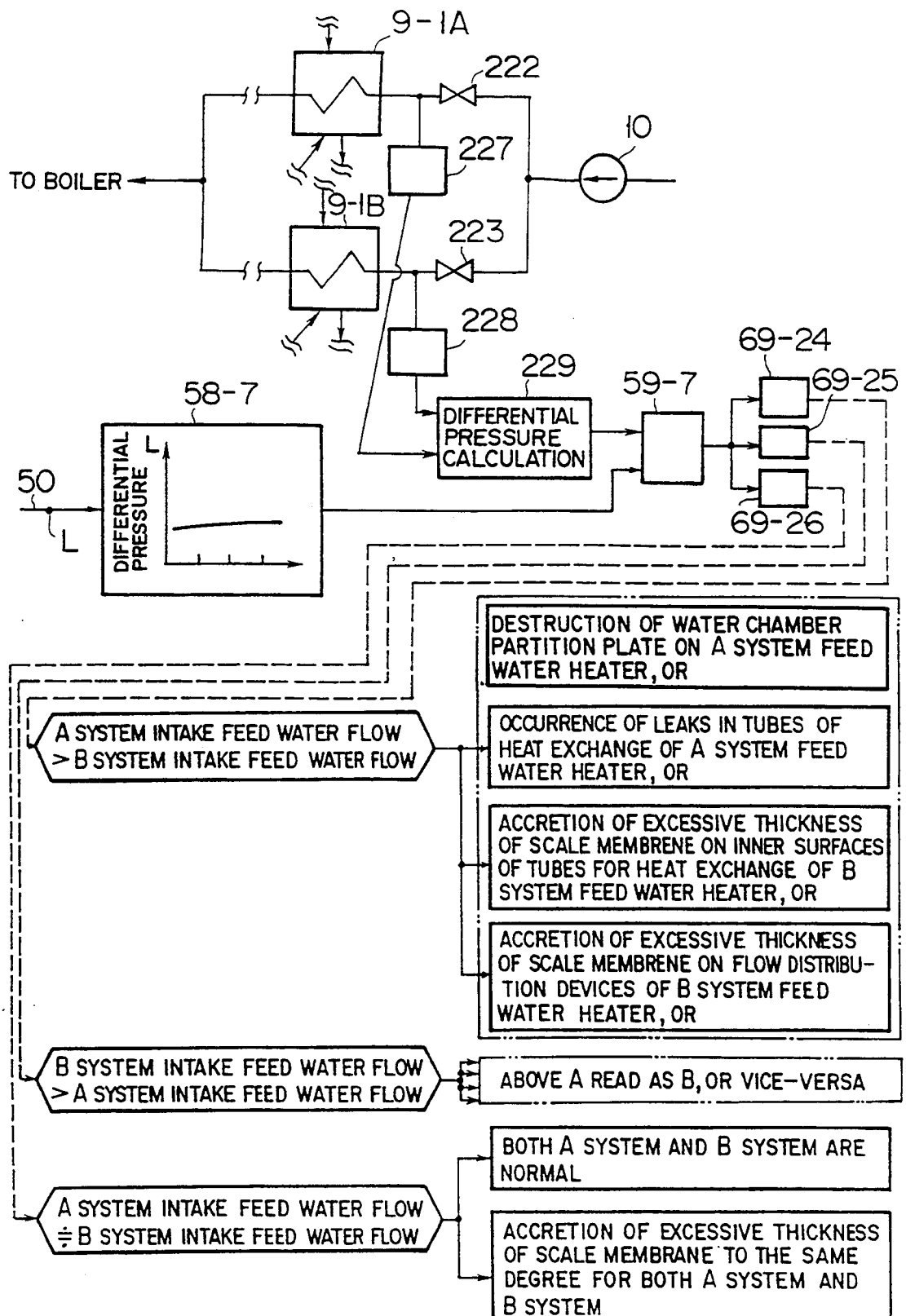
FIG. 28 is a diagram showing the judgment logic in a modification of the embodiment of the second invention.

As shown in FIG. 28, the pressure of the outlet side of the A system feed water inlet valve 222 and the outlet side of the B system feed water inlet valve 223 is detected by the feed water inlet valve outlet pressure detection portions 227,228 and this differential pressure is calculated by the subtractor portion 229 and compared in the subtractor portion 59-7 with the output value from the differential pressure reference value calculation portion 58-7 and any deviation is input to the alarm setting portions 69-24 through 69-26 and the output of these is processed by the judgment logic shown in the lower half of FIG. 28, so that when there is an imbalance in the inlet feed water flows that respectively flow into the A system and the B system, it is possible to judge this as well as the relative amount of balance of the feed water system in which the greater amount of feed water is flowing.

Moreover, in FIG. 28, as shown at the bottom of the right side of the judgment logic, there is the judgment for "accretion of scale membrane to the feed water flow path to the same degree for both the A system and the B system". It is inconceivable that there be the simultaneous occurrence of "destruction of the water chamber partition plate" and the "occurrence of leaks in the heat exchanger tubes."

Figure 29:
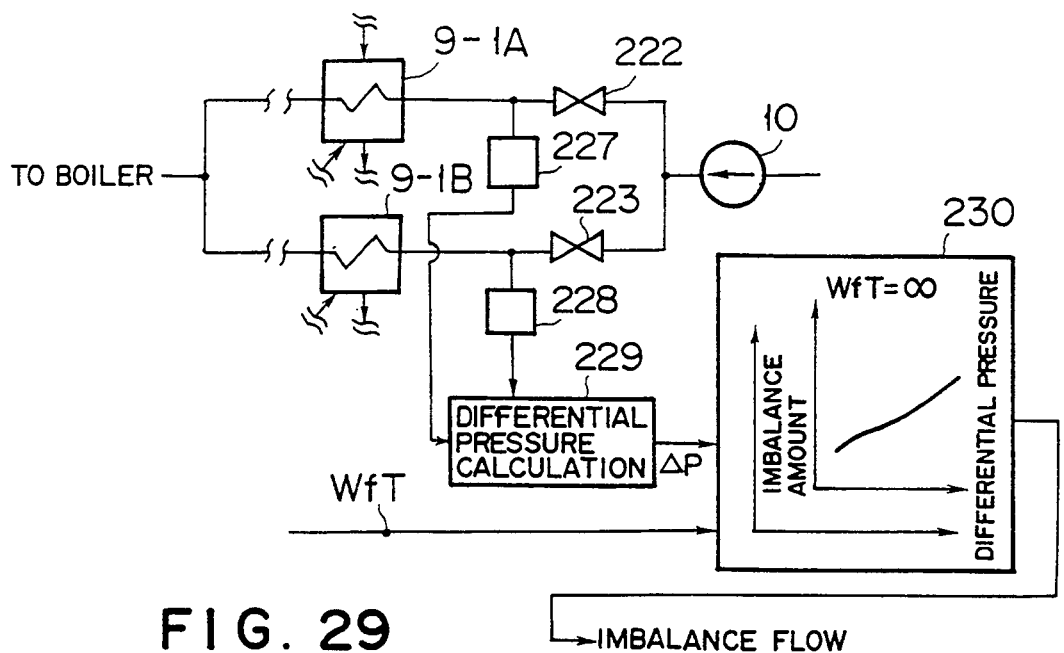
FIG. 29 is a diagram showing the judgment logic in a modification of the embodiment of the second invention.

In addition, as shown in FIG. 29, the inlet side pressures of the A system feed water inlet valve 222 and the B system feed water inlet valve 223 of each of the systems are both the same but the following equation is established between the feed water flow F that flows in each of the feed water inlet valves and the inlet/outlet pressure $\Delta P$ of each of the feed water inlet valves $$F \alpha \Delta P^{\frac{1}{2}}$$

and when the total feed water flow that flows into the boiler is measured, the relationship between the size of the differential pressure between outlet sides of the feed water inlet valves of the A system and the B system, and the amount of the difference of the inlet feed water flow that respectively flows into the feed water inlet valves 222,223 are determined beforehand for each of the total feed water flows and stored in the imbalance flow calculation portion 230 so that it is possible to calculate the absolute value of the amount of imbalance of the intake feed water flow to the A system and the B system.

In this manner, when it is detected that the difference between the inlet feed water flows to the A system and the B system is greater than a rated value, it is possible to have processing by the judgment logic indicated in the lower half of FIG. 28. Accordingly, if there is the addition of an "AND" condition to the judgment logic shown in FIG. 16, FIG. 21, FIG. 22, FIG. 24 and FIG. 25. There is the further effect of being able to raise the judgment accuracy.

In this embodiment, there was the measurement of the differential pressure between outlet sides of the feed water inlet valves of each system but instead of each of the feed water inlet valves, the same effect can be obtained if an orifice plate or a flow nozzle for the measurement of the flow is provided to the feed water inlet portion of each of the systems and the differential pressure between secondary sides (outlet sides) measured.

EXAMPLE 8

With the embodiments described above and the modifications, therefore, there is the judgment of abnormalities in the feed water heater using the inlet feed water flow. But in the status where the power generation plant, including the feed water heater is normal, the correlation relationship between the inlet feed water flow of the feed water heater and the drain outlet flow is constant (FIG. 19). So, it is possible to have the same effect using the drain outlet flow instead of the inlet feed water flow of the feed water heater.

In the embodiment shown in FIG. 26, a plural number of feed water heaters are disposed in series and a plural number of systems of these are disposed in parallel, and for reasons of equipment arrangement, there are power generation plants where it is not possible to measure the drain outlet flow for each of the feed water heaters disposed in series. However, in power generation plants having a configuration such as this, there is generally the possibility of measurement of the drain outlet flow in the drain pipes 13-1A, 13-1B.

Figure 30:
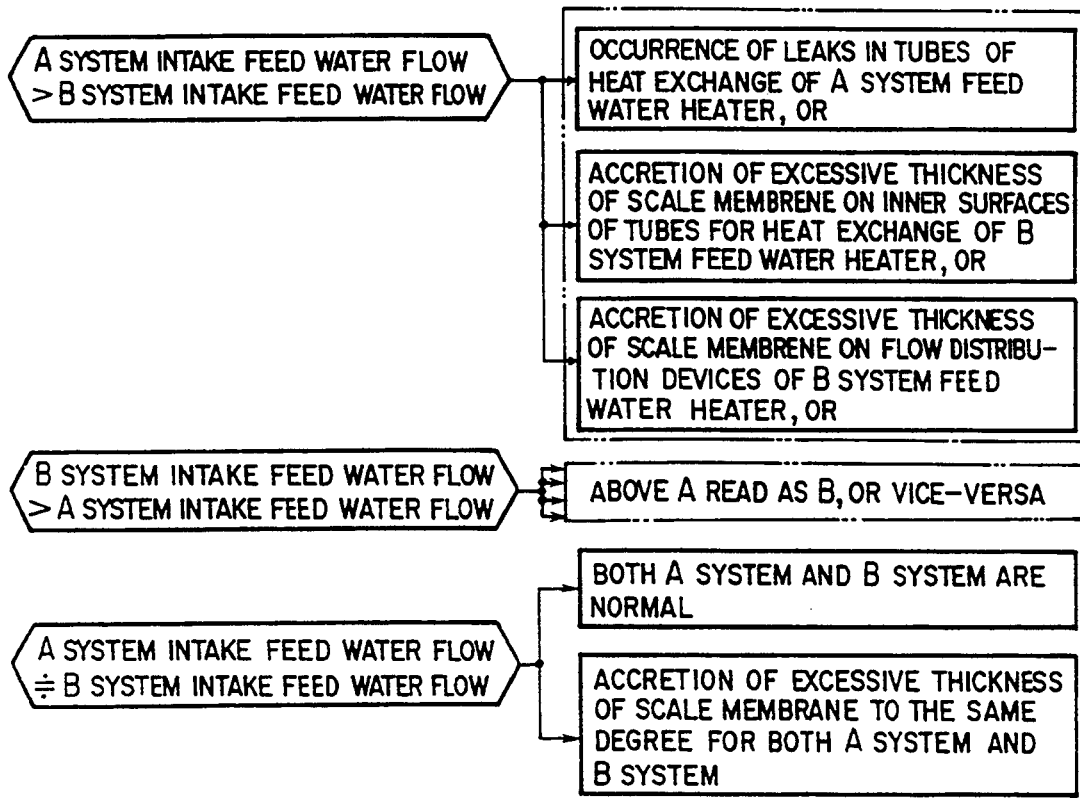
FIG. 30 is a diagram showing the judgment logic in a modification of the embodiment of the second invention.

In the power generation plant, this drain outlet flow is used instead of the inlet feed water flow value to each system, and if the judgment block such as that shown in FIG. 30 has the AND condition of the judgment logic of FIG. 16, FIG. 21, FIG. 22, FIG. 24 and FIG. 25 added to it, it is possible to have the further effect of increasing the judgment accuracy.

The following is a description of the operation of the judgment logic of FIG. 30, with reference to FIG. 26.

In FIG. 26, the extraction steam that is supplied to the FIG. 9-3A via the extraction steam tubes 12-3A is cooled by the feed water, becomes drain and passes through the drain tubes 13-3A, and flows into the feed water heater 9-2A. On the other hand, the extraction steam that is supplied to the feed water heater 9-2A via the extraction steam tubes 12-2A and is cooled by the feed water to become drain, and combines with the drain described above and flows into the feed water heater 9-1A via the drain tubes 13-2A. After this, in the same manner, all of the extraction steam that is supplied to the feed water heaters 9-1A through 9-3A of the A system becomes drain, and flows to the deaerator from the drain pipes 12-1A. This is the same for the feed water heaters 9-1B through 9-3B for the B system.

Also, when there the "accretion of scale membrane to the flow distribution devices and the inner surface of the heat exchanger tubes (the occurrence of scale membrane to the feed water flow path portions to the same degree for both systems)" and the "normal status for the power generation plant including the feed water heaters, for both the A system and the B system," the inlet feed water flow to both of the systems are substantially the same and so the outlet drain flow for the A system outlet drain flow and the B system outlet drain flow are also substantially the same. In addition, when there is the occurrence of leaks in the tubes of the heat exchanger of the A system feed water heater, the there is of course the situation where "A system outlet drain flow > B system outlet drain flow."

In addition, although it is dependent upon the structure of the power generation plant including the feed water heaters, in general, the inlet feed water flow to the B system reduces in cases when there is the "accretion of an excessive thickness of scale membrane" to the flow distribution devices and the feed water flow path or to the inner surface of the tubes of the heat exchanger of the feed water heater of the B system and so in the judgment block that uses the above embodiment, there is the saturation for "A system outlet drain flow>B system outlet drain flow." Moreover, this relationship is established by rewriting the above A and B.

EXAMPLE 9

In the embodiment described above, the method for the calculation of the heat exchange performance of the feed water heater is the method where the "difference between the feed water outlet temperature and the saturation temperature of the internal pressure of the feed water heater in the extractioni steam inlet" and the "difference between the feed water heater inlet temperature and the drain outlet temperature" was used. Instead of this method, it can alternatively be the method that was described in connection with FIG. 9 and FIG. 13. Moreover, in the case of this method, the simple method of evaluating the heat exchange performance using only $\Delta T1$, $\Delta T2$ such as the calculation of the heat exchange performance of the feed water heater, and calculating the heat exchange performance of the feed water heater involves measuring the drain outlet flow Wd or the extraction steam inlet flow Ws, and the feed water inlet flow Wf to each of the feed water heaters and calculating the coefficient of thermal conductivity for each portion of the desuperheating zone, the condensing zone and the drain cooling zone of the feed water heater.

With this method, the method is for the evaluation and evaluation of the heat exchange performance of each portion of the feed water heater and so in addition to the effect of the embodiments described above and the modifications (1) through (8) thereof, the results for whether the heat exchange performance for which portion of the feed water heater is dropping can be used to judge whether the location of a leak in the heat exchanger tubes is for the desuperheating zone, the condensing zone and the drain cooling zone of the feed water heater. In addition, there is also the effect of the short path due to the destruction of the drain cooling zone enclosure or the intake of extraction steam to the drain cooling portion, being able to be judged by the absence of trouble in the feed water heater.

What is claimed is:

1. A system for monitoring abnormalities in a heat exchanger having heat-exchange tubes for heating feed water with an extraction steam, an inlet and an outlet for the feed water, and a drain cooling zone, said monitoring system comprising:
    pressure means for calculating a differential pressure between the feed water pressures at said inlet and outlet;
    calculation means for computing a heat exchange performance of the heat exchanger; and
    judgment means for monitoring said differential pressure and said heat exchange performance, thereby judging the presence or absence of a scale accretion within the heat exchanger and, whenever said scale accretion is present, judging the specific locations of the scale accretion in the inner and outer surfaces of the heat-exchange tubes, fluid flow distribution passageways in said system and devices other than the heat-exchange tubes in said system and wherein a feed water inlet pressure measuring unit and a feed water outlet pressure measuring unit are respectively installed at places where the pulsation of the feed water inlet and the pulsation of the feed water outlet of the heat exchanger are respectively, as small as possible.

2. A system for monitoring abnormalities in a heat exchanger having heat-exchange tubes for heating feed water with an extraction steam, an inlet and an outlet for the feed water, and a drain cooling zone, said monitoring system comprising:
    pressure means for calculating a differential pressure between the feed water pressures at said inlet and outlet;
    calculation means for computing a heat exchange performance of the heat exchanger; and
    judgment means for monitoring said differential pressure and said heat exchange performance, thereby judging the presence or absence of a scale accretion within the heat exchanger and, whenever said scale accretion is present, judging the specific locations of the scale accretion in the inner and outer surfaces of the heat-exchange tubes, fluid flow distribution passageways in said system and devices other than the heat-exchange tubes in said system and wherein the monitoring system monitors both the difference between a feed water outlet temperature and a saturated temperature inside the feed water heater at an extracted steam outlet and the difference between a feed water inlet temperature and a drain outlet temperature.

3. A system for monitoring abnormalities in a heat exchanger having heat-exchange tubes for heating feed water with an extraction steam, an inlet and an outlet for the feed water, and a drain cooling zone, said monitoring system comprising:
    pressure means for calculating a differential pressure between the feed water pressures at said inlet and outlet;
    calculation means for computing a heat exchange performance of the heat exchanger; and
    judgment means for monitoring said differential pressure and said heat exchange performance, thereby judging the presence or absence of a scale accretion within the heat exchanger and, whenever said scale accretion is present, judging the specific locations of the scale accretion in the inner and outer surfaces of the heat-exchange tubes, fluid flow distribution passageways in said system and devices other than the heat-exchange tubes in said system and wherein the calculation means calculates the ratio of thermal conductivity via the heat exchange tubes using the values obtained for the temperature of a drain and the extracted steam, and the feed water that flows into at least portions of a superheating zone, a condensing zone, the drain cooling zone, and uses these results to monitor the heat exchange performance.

4. A system for monitoring abnormalities in a heat exchanger having heat-exchange tubes for heating feed water with an extraction of steam, an inlet and outlet for the feed water, and a drain cooling zone, said monitoring system comprising:
    pressure means for calculating a differential pressure between the feed water pressures at said inlet and outlet;
    calculation means for computing a heat exchange performance of the heat exchanger; and judgment means for monitoring said differential pressure and said heat exchange performance, thereby judging the presence or absence of scale accretion within the heat exchanger and, whenever said scale accretion is present, judging the specific location of the scale accretion on the inner and outer surfaces of the heat-exchange tubes, fluid flow distribution passageways in said system and devices other than the heat-exchange tubes in said system, wherein an inlet feed water flow to the heat exchanger and a drain outlet flow are monitored for determining the intake of the extraction steam in the drain cooling zone and a short path within a drain due to destruction of a heat exchanger drain cooling zone enclosure plate, the destruction of a water chamber partition plate, the presence of leaks in the heat exchange tubes, and the accretion of scale in drain level adjustment valves.

5. A system for monitoring abnormalities in a heat exchanger having heat-exchange tubes for heating feed water with an extraction steam, an inlet and an outlet for the feed water, and a drain cooling zone, said monitoring system comprising:

pressure means for calculating a differential pressure between the feed water pressures at said inlet and said outlet;

calculation means for computing a heat exchange performance of the heat exchanger; and judgment means for monitoring said differential pressure and said heat exchange performance, thereby judging the presence or absence of scale accretion within the heat exchanger and, whenever said scale accretion is present, judging the specific locations of the scale accretion on the inner and outer surfaces of the heat-exchange tubes, fluid flow distribution passageways in said system and devices other than the heat-exchange tubes in said system, wherein the monitoring system monitors the degree of opening of a drain water level adjustment valve for determining operating abnormalities of the drain water level adjustment valve and sticking of the drain water level adjustment valve.

6. A system for monitoring abnormalities in a heat exchanger having heat-exchange tubes for heating feed water with an extraction steam, an inlet and outlet for the feed water, and a drain cooling zone, said monitoring system comprising:

pressure means for calculating a differential pressure between the feed water pressures at said inlet and outlet;

calculation means for computing a heat exchange performance of the heat exchanger; and judgment means for monitoring said differential pressure and said heat exchange performance, thereby judging the presence or absence of a scale accretion within the heat exchanger and, whenever said scale accretion is present, judging the specific locations of the scale accretion on the inner and outer surfaces of the heat-exchange tubes, fluid flow distribution passageways in said system and devices other than the heat-exchange tubes in said system, wherein the monitoring system monitors an imbalance in the inlet feed water flow in a plurality of feed water heaters by a change of the differential pressure obtained by monitoring the differential pressures between pairs of outlet sides of an orifice plate and a plurality of flow nozzles, and feed water inlet valves installed respectively on the feed water inlet.

* * * * *